US009206445B2

(12) United States Patent
Yang et al.

(10) Patent No.: US 9,206,445 B2
(45) Date of Patent: Dec. 8, 2015

(54) BIOCATALYSTS WITH ENHANCED INHIBITOR TOLERANCE

(71) Applicant: Alliance for Sustainable Energy, LLC, Golden, CO (US)

(72) Inventors: Shihui Yang, Lakewood, CO (US); Jeffrey Linger, Denver, CO (US); Mary Ann Franden, Centennial, CO (US); Philip T. Pienkos, Lakewood, CO (US); Min Zhang, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 88 days.

(21) Appl. No.: 14/265,039

(22) Filed: Apr. 29, 2014

(65) Prior Publication Data

US 2014/0342421 A1  Nov. 20, 2014

Related U.S. Application Data

(60) Provisional application No. 61/817,053, filed on Apr. 29, 2013.

(51) Int. Cl.
*C12P 7/16* (2006.01)
*C12P 7/06* (2006.01)
*C07K 14/195* (2006.01)
*C12N 9/12* (2006.01)
*C12P 7/10* (2006.01)

(52) U.S. Cl.
CPC ............... *C12P 7/065* (2013.01); *C07K 14/195* (2013.01); *C12N 9/12* (2013.01); *C12P 7/10* (2013.01); *C12Y 207/13003* (2013.01); *Y02E 50/17* (2013.01)

(58) Field of Classification Search
CPC combination set(s) only.
See application file for complete search history.

(56) References Cited

U.S. PATENT DOCUMENTS

| 4,952,501 | A  | 8/1990  | Jasin et al. |
| 5,514,583 | A  | 5/1996  | Picataggio et al. |
| 5,843,760 | A  | 12/1998 | Zhang et al. |
| 6,566,107 | B1 | 5/2003  | Zhang |
| 7,223,575 | B2 | 5/2007  | Zhang et al. |
| 7,354,755 | B2 | 4/2008  | Zhang et al. |
| 7,803,623 | B2 | 9/2010  | Caimi et al. |
| 7,897,396 | B2 | 3/2011  | Caimi et al. |
| 2010/0311137 | A1 | 12/2010 | Brown et al. |

OTHER PUBLICATIONS

Arfman et al., "Use of the tac promoter and lacIq for the controlled expression of *Zymomonas mobilis* fermentative genes in *Escherichia coli* and *Zymomonas mobilis*", Journal of Bacteriology, Nov. 1992, vol. 174, No. 22, pp. 7370-7378.
Galbe et al., "Pretreatment of Lignocellulosic Materials for Efficient Bioethanol Production", Advances in Biochemical Engineering Biotechnology, 2007, vol. 108, pp. 41-65.
Goeddel, "Systems for Heterologous Gene Expression", Methods in Enzymology, 1990, vol. 185, pp. 3-7.
Kubo et al., "Location of a region of the muscarinic acetylcholine receptor involved in selective effector coupling", FEBS Letters, Dec. 1988, vol. 241, Nos. 1-2, pp. 119-125.
Senthilkumar et al., "Characterization of multiple promoters and transcript stability in the sacB-sacC gene cluster in *Zymomonas mobilis*", Archives of Microbiology, Jun. 2009, vol. 191, No. 6, pp. 529-541.
Yang et al., "Strain Development in Omics Era", 35th SIMB Symposium, Apr. 29, 2013, Portland, Oregon, pp. 1-24.

*Primary Examiner* — Kagnew H Gebreyesus
(74) *Attorney, Agent, or Firm* — John C. Stolpa

(57) ABSTRACT

Disclosed herein are biocatalysts for the production of biofuels, including microorganisms that contain genetic modifications conferring tolerance to growth and fermentation inhibitors found in many cellulosic feedstocks. Methods of converting cellulose-containing materials to fuels and chemicals, as well as methods of fermenting sugars to fuels and chemicals, using these biocatalysts are also disclosed.

18 Claims, 15 Drawing Sheets

Figure 1

A. SEQ ID NO:1

ATGACTTTTCCCCAATCAAGGCTGAGAAAGGACTGCGTTATTAAATTTATCCCTGTCTATCT
ATCCGGATTATCAATCCTGGCTCTATTTATTATTGCCGTCAGTCATGTTTCTGTCGGGTGGC
CGATCTTGTCGCTTATGCTGATTGTTATCCTTTGGGGATGGTGGTTTAAAAATATTTCCGAA
GCGTCTACCCCCTTCCCTGAAAGTAAAAGCGGAAATAGCCTTACGGATCCTGCCTATCCTTT
TTCTCAAGCGACAGCGGCAGATATTATTATAGCTATGGATGAACCAGCTTTACTGGTCAATC
AGGGTCAAGTTGAAGTGGCTAATCGTGCCGCTGAAAATTTGTTAGGGATGCATATCGAAGGA
GGCGACATCAGAATGGCTATTCGCCATCCTGCTGCTATCCGTCTTTTAACCGAGCCGCTTGA
TAATATGACTCCTGTTTTACTTGCCGGATTGGGAGGCGTTAATCGTCGCTGGGAATTATACG
CTTATCCTTTGAACGAAGAACAACGGCTCATTTGTTGCGCGATCAAAGTACGGCTCATTTA
ACGGAACAGGTTAGAATAGACTTTGTTGCGAATACTAGTCACGAATTACGGACACCGCTCGC
GACTTTAAGCGGGTTTATTGAGACATTAGAAGATGATGATGTCATTAAAGAGCGCGATACGC
GTCATCATTTTTTGTCTATTATGGCGCGTGAAGCCAAAAGAATGCAAAATTTGGTTGATGAC
TTGATGTCTCTTTCTCGGATTGAAGCCGGAAAATTTTCATTACCCCATGATATTGTTCATAT
GTCGCCTGTGGTTGAAGAGGTCGTGTCTAATATTCAGGCATCGGGACAGGCAAAAGCCACCC
AAATCACACTCGAAAATCATTTGTCCAGTGATAGCCTACAGGGTGACCGCGCCGAGTTAACG
CAGCTCCTTTATAACATTATCGGCAATGCCTTAAAATATGGTCGTAAAGATGGAATAATTAA
AGTCGCGCTCGATAATACTGACGATCATAGAATAAAATTAGCTATTGCAGATGAAGGCGATG
GTATTCCGTTTCATCATATCCCGCGCCTAACGGAACGCTTCTATCGGGTGGATAACAGCCGT
AGTCGCGCTTTAGGGGGAACAGGATTGGGGCTAGCCATAGTAAAACAAATCGTCGAGCATCA
TCGCGGAGAATTACTGATAGACAGCCTCCCCGGTAAAGGGACGACGGTAACCGTTTTCTTGC
CAACGACCGATTTTTTCCCTGAA

B. SEQ ID NO:2

MTFPQSRLRKDCVIKFIPVYLSGLSILALFIIAVSHVSVGWPILSLMLIVILWGWWFKNISE
ASTPFPESKSGNSLTDPAYPFSQATAADIIIAMDEPALLVNQGQVEVANRAAENLLGMHIEG
GDIRMAIRHPAAIRLLTEPLDNMTPVLLAGLGGVNRRWELYAYPLNEEQRLILLRDQSTAHL
TEQVRIDFVANTSHELRTPLATLSGFIETLEDDDVIKERDTRHHFLSIMAREAKRMQNLVDD
LMSLSRIEAGKFSLPHDIVHMSPVVEEVVSNIQASGQAKATQITLENHLSSDSLQGDRAELT
QLLYNIIGNALKYGRKDGIIKVALDNTDDHRIKLAIADEGDGIPFHHIPRLTERFYRVDNSR
SRALGGTGLGLAIVKQIVEHHRGELLIDSLPGKGTTVTVFLPTTDFFPE

Figure 2

A.  SEQ ID NO:3

ATGGATATCCGTATTTCCGGCCATCAGATTGATACAGGCGCGGCTTTAAGAGAATATGTCAA
TGACCATCTTAGCCAGATCGTCAGCAAATATTTCCCCAAATGCCTAAGCGCCTCTGTCACTT
TCGGTAATCGTCGCCACGCTATTATTTCCTGCGATATTATTATCCATGCCATGCGGGATATT
ATTCTGAAAGCAGGCGGCATAGACAAAGACGCCCATGCCGCTTTCGATCAGGCCGCCGCCAA
GATTGAAAAACAATTACGGCGACATCACCGACGTTTACAGACCCGCGTCCAGCAAAATACGC
CTTCTATTGATGAAGCCGCTATCGCCCTTACGGAGGCAACAGCCAAGGCGGATCAGGATAAC
GCGCATTATACGGTCTTTGACATTGAAGAGGATGAAAAAGAGCAAGGCGATCATCCTCCCGT
CATTGCCGAAATGCAGGTTGATATTCCAACAGCCAGCGTTTCCGATGCTGTTTTGATGCTCG
ATCTTCGCAACACGACGGCTTTGCTCTTCGTGAACAGCAAATCGGGTCATCATAATATGGTT
TATCGTCGGGTAGATGGTACCATCGGTTGGGTTGAGCCGCGA

B.  SEQ ID NO:4

MDIRISGHQIDTGAALREYVNDHLSQIVSKYFPKCLSASVTFGNRRHAIISCDIIIHAMRDI
ILKAGGIDKDAHAAFDQAAAKIEKQLRRHHRRLQTRVQQNTPSIDEAAIALTEATAKADQDN
AHYTVFDIEEDEKEQGDHPPVIAEMQVDIPTASVSDAVLMLDLRNTTALLFVNSKSGHHNMV
YRRVDGTIGWVEPR

Figure 3

A. SEQ ID NO:5

ATGCCTAATGCAGAGTTTGATTTCAGGCCTATGTTTCCGAATAAAAAGACGCCGTTGTTAGA
CAAGATCAAGACACCGGCAGAATTGCGTCAATTAGATCGCAACAGCCTCCGGCAATTGGCGG
ATGAATTACGGAAAGAGACCATCTCGGCAGTGGGTGTGACCGGCGGACATCTCGGTTCCGGT
CTGGGGGTTATCGAATTAACGGTAGCTCTTCATTATGTTTTCAACACGCCCAAAGACGCTTT
GGTCTGGGATGTTGGGCATCAAACCTATCCTCACAAGATTTTAACAGGTCGCCGTGATCGTA
TTCGGACATTGCGGCAACGTGACGGCTTATCGGGCTTTACGCAGCGCGCGGAGAGCGAATAT
GACGCTTTTGGAGCAGCGCATAGTTCGACTTCTATTTCTGCGGCGCTCGGCTTTGCGATGGC
CAGCAAATTATCCGACAGCGACGACAAAGCGGTTGCGATTATCGGTGATGGCTCGATGACGG
CAGGCATGGCTTATGAAGCCATGAATAACGCCAAGGCGGCGGGTAAGCGCCTGATTGTCATT
TTGAATGACAATGAAATGTCGATTTCACCGCCGGTGGGTGCCTTATCGTCTTATTTGAGCCG
CCTGATTTCCTCACGGCCTTTCATGAATTTGCGCGATATCATGCGCGGTGTTGTCAACCGGA
TGCCAAAAGGCTTGGCAACGGCTGCCCGCAAGGCTGATGAATATGCGCGTGGTATGGCAACC
GGTGGCACCTTCTTTGAAGAGCTGGGCTTTTACTATGTTGGCCCCGTAGATGGTCATAATTT
AGATCAGCTCATTCCGGTTTTGGAAAATGTCCGCGATGCCAAGGACGGCCCCATTTTGGTGC
ATGTCGTCACCCGCAAAGGCCAAGGCTATGCTCCGGCTGAAGCGGCCAAGGACAAATATCAC
GCCGTGCAGCGCTTGGATGTGGTTTCCGGCAAGCAGGCGAAAGCGCCCCAGGGCCTCCCAG
CTATACCTCTGTTTTCTCGGAACAGCTGATCAAGGAAGCTAAGCAAGACGATAAGATTGTGA
CCATTACGGCAGCTATGCCGACTGGCACCGGTCTTGATCGCTTCCAGCAATATTTTCCTGAA
AGAATGTTTGATGTCGGTATTGCCGAACAACATGCCGTAACCTTTGCGGCTGGTTTGGCGGC
TGCCGGTTACAAGCCTTTCTGTTGTCTCTATTCGACCTTCTTGCAGCGCGGCTATGACCAGT
TAGTGCATGATGTCGCTATCCAGAATTTGCCGGTGCGCTTCGCCGTCGATCGTGCGGGTCTT
GTCGGTGCCGATGGGGCAACCCATGCGGGTAGCTTCGACCTCGCCTTTATGGTTAATCTACC
GAATATGGTCGTGATGGCGCCTTCCGATGAACGGGAATTGGCCAATATGGTGCATAGCATGG
CGCATTATGACCAAGGCCCGATCTCGGTGCGTTATCCGCGTGGTAATGGTGTGGGTGTCTCC
TTGGAAGGCGAAAAGGAAATTCTGCCTATCGGGAAAGGTCGCCTGATCCGTCGCGGTAAAAA
GGTTGCTATCCTATCTCTCGGCACTCGATTGGAAGAATCCTTGAAGGCTGCTGATCGGCTTG
ATGCTCAAGGTTTGTCGACATCGGTTGCTGATATGCGTTTTGCTAAGCCCTTGGATGAAGCG
CTGACCCGCCAACTTCTAAAAAGCCATCAGGTCATTATTACCATTGAAGAAGGCGCTTTGGG
TGGTTTTGCAACCCAAGTCCTGACGATGGCTTCGGATGAAGGCCTGATGGATGACGGATTGA
AAATCCGCACCCTGCGTCTGCCGGATCGGTTCCAGCCGCAAGACAAGCAAGAACGGCAATAT
GCCGAAGCTGGTCTTGATGCTGATGGCATCGTTGCTGCCGTAACGGCTGCATTACAACGGAA
CTCAAAGCCTGTCGAAGTCGTTGAGCTGACTACAAAAGTAACAGAAGATATGACTTTATGA

B. SEQ ID NO:6

MPNAEFDFRPMFPNKKTPLLDKIKTPAELRQLDRNSLRQLADELRKETISAVGVTGGHLGSG
LGVIELTVALHYVFNTPKDALVWDVGHQTYPHKILTGRRDRIRTLRQRDGLSGFTQRAESEY
DAFGAAHSSTSISAALGFAMASKLSDSDDKAVAIIGDGSMTAGMAYEAMNNAKAAGKRLIVI
LNDNEMSISPPVGALSSYLSRLISSRPFMNLRDIMRGVVNRMPKGLATAARKADEYARGMAT
GGTFFEELGFYYVGPVDGHNLDQLIPVLENVRDAKDGPILVHVVTRKGQYAPAEAAKDKYH
AVQRLDVVSGKQAKAPPGPPSYTSVFSEQLIKEAKQDDKIVTITAAMPTGTGLDRFQQYFPE
RMFDVGIAEQHAVTFAAGLAAAGYKPFCCLYSTFLQRGYDQLVHDVAIQNLPVRFAVDRAGL
VGADGATHAGSFDLAFMVNLPNMVVMAPSDERELANMVHSMAHYDQGPISVRYPRGNGVGVS
LEGEKEILPIGKGRLIRRGKKVAILSLGTRLEESLKAADRLDAQGLSTSVADMRFAKPLDEA
LTRQLLKSHQVIITIEEGALGGFATQVLTMASDEGLMDDGLKIRTLRLPDRFQPQDKQERQY
AEAGLDADGIVAAVT AALQRNSKPVEVVELTTKVTEDMTL

Figure 4

A. SEQ ID NO:7

ATGTTTCCGAATGACAAGACGCCGCTGTTAGACAAGATCAAGACACCGGCAGAATTGCGTCA
ATTAGATCGCAACAGCCTCCGGCAATTGGCGGATGAATTACGGAAAGAGACCATCTCGGCAG
TGGGTGTGACCGGCGGACATCTCGGTTCCGGTCTGGGGGTTATCGAATTAACGGTAGCCCTT
CACTATGTTTTCAACACGCCCAAAGACGCTTTAGTCTGGGATGTTGGGCATCAAACCTATCC
TCACAAGATTTTAACAGGTCGCCGCGATCGTATTCGGACATTGCGGCAACGTGACGGCTTAT
CGGGCTTTACGCAGCGCGCGGAGAGCGAATATGACGCTTTTGGAGCCGCGCATAGTTCGACT
TCTATTTCTGCGGCGCTCGGCTTTGCGATGGCCAGCAAATTATCCGACAGCGACGACAAAGC
GGTTGCGATTATCGGTGATGGCTCGATGACGGCAGGCATGGCTTATGAAGCCATGAATAACG
CCAAGGCGGCGGGTAAGCGCCTGATTGTCATTTTGAATGACAATGAAATGTCGATTTCACCG
CCGGTGGGTGCCTTATCGTCTTATTTGAGCCGCCTGATTTCCTCACGGCCTTTCATGAATTT
GCGCGATATCATGCGCGGCGTTGTTAACCGGATGCCAAAAGGCTTGGCAACGGCTGCCCGCA
AGGCTGATGAATATGCGCGTGGTATGGCAACCGGTGGCACCTTCTTTGAAGAGCTGGGCTTT
TACTATGTTGGCCCCGTGGATGGTCATAATTTAGATCAGCTCATTCCAGTTTTAGAAAATGT
CCGCGATGCCAAGGACGGCCCCATTTTGGTGCATGTCGTCACTCGCAAAGGCCAAGGCTATG
CTCCGGCTGAAGCGGCCAAGGACAAATATCACGCCGTGCAGCGCTTGGATGTGGTTTCCGGT
AAGCAGGCGAAAGCGCCCCGGGACCTCCCAGCTATACCTCTGTTTTTTCGGAACAGCTGAT
CAAGGAAGCTAAGCAAGACGATAAGATTGTGACCATTACGGCAGCTATGCCGACTGGCACCG
GTCTTGATCGTTTTCAGCAATATTTTCCTGAAAGAATGTTTGATGTCGGTATTGCCGAACAA
CATGCCGTAACCTTTGCGGCTGGTTTGGCGGCTGCCGGTTACAAGCCTTTCTGTTGTCTCTA
TTCGACCTTCTTGCAGCGCGGCTATGACCAGTTGGTGCATGATGTCGCTATCCAGAATTTGC
CGGTGCGCTTCGCCGTCGATCGTGCGGGTCTTGTCGGTGCCGATGGGGCAACCCATGCGGGT
AGCTTCGACCTCGCCTTTATGGTTAATCTCCCGAATATGGTCGTGATGGCGCCTTCCGATGA
ACGGGAATTGGCCAATATGGTGCATAGCATGGCGCATTATGACCAAGGCCCGATCTCGGTGC
GTTATCCGCGTGGTAATGGTGTGGGTGTCTCCTTGGAAGGTGAAAAGGAAATTCTGCCTATC
GGGAAAGGTCGCCTGATCCGTCGCGGTAAAAAGGTTGCTATCCTATCTCTCGGCACTCGATT
GGAAGAATCCTTGAAGGCTGCTGATCGGCTTGATGCTCAAGGTTTGTCGACATCGGTTGCTG
ATATGCGTTTTGCTAAGCCCTTGGATGAAGCGCTGACCCGCCAACTTTTGAAAAGCCATCAG
GTCATTATTACCATTGAAGAAGGCGCTTTGGGTGGTTTTGCAACCCAAGTCCTGACGATGGC
TTCGGATGAAGGCCTGATGGATGACGGATTGAAAATCCGCACCCTGCGTCTGCCGGATCGGT
TCCAGCCGCAAGACAAGCAAGAACGGCAATATGCCGAAGCCGGTCTTGATGCTGATGGCATC
GTTGCTGCGGTTATCTCCGCATTGCATCGTAATTCTAAACCCGTGGAAGTCGTCGAAATGGC
GAATATGGGTAGCATCGCTCGCGCTTAA

B. SEQ ID NO:8

MFPNDKTPLLDKIKTPAELRQLDRNSLRQLADELRKETISAVGVTGGHLGSGLGVIELTVAL
HYVFNTPKDALVWDVGHQTYPHKILTGRRDRIRTLRQRDGLSGFTQRAESEYDAFGAAHSST
SISAALGFAMASKLSDSDDKAVAIIGDGSMTAGMAYEAMNNAKAAGKRLIVILNDNEMSISP
PVGALSSYLSRLISSRPFMNLRDIMRGVVNRMPKGLATAARKADEYARGMATGGTFFEELGF
YYVGPVDGHNLDQLIPVLENVRDAKDGPILVHVVTRKGQGYAPAEAAKDKYHAVQRLDVVSG
KQAKAPPGPPSYTSVFSEQLIKEAKQDDKIVTITAAMPTGTGLDRFQQYFPERMFDVGIAEQ
HAVTFAAGLAAAGYKPFCCLYSTFLQRGYDQLVHDVAIQNLPVRFAVDRAGLVGADGATHAG
SFDLAFMVNLPNMVVMAPSDERELANMVHSMAHYDQGPISVRYPRGNGVGVSLEGEKEILPI
GKGRLIRRGKKVAILSLGTRLEESLKAADRLDAQGLSTSVADMRFAKPLDEALTRQLLKSHQ
VIITIEEGALGGFATQVLTMASDEGLMDDGLKIRTLRLPDRFQPQDKQERQYAEAGLDADGI
VAAVISALHRNSKPV EVVEMANMGSIARA

Figure 5

A.  SEQ ID NO:9

TTGAAACGAAAAATTGCTCCAATATCTGTTTTTGCCGGATCAGTCTTGATGATGCTGACGGC
CTGTCACCATCAATCCCAAGAAGCCGAACCGGCATTGCAAGATGTTAGTTTTGTTACCGTAA
AAACGCAGCCTTTGACCGTTCATAGCACCTTACCCGGTCGCACTTCGGCTTATGAGGTGGCG
GAAGTAAGACCTCAGGTAAATGGGGTCGTTTTGGCGCGCTATTTTAACGAAGGCACGGATGT
CAAAAAAGGGCAGCCGCTATTCCTTATCAATCCGGCTCCTTATCAAGCGACTTATGACGTTA
ATAAAGCGCAATTAGCTCATGCTGAAGCGCAAGAGAAAACGGCTGCTGCTAAATTAGAACGC
TATAAGGCTTTGGCTCCGGCGCAGGCGATTAGTCGTCAGGATTATGATGATGCTTTGGCCAC
CGATCGCGCGGCCAAGGCAGATATTGCCCAAGCCAAAGCGAATATTGAATTATCGGCTGTTA
ATTTGGATACACCCGTGTGACCGCGCCTATTACTGGCCGGATCGGGCGCGTTTTGACAACG
GTCGGTGCCTTGGTAACGTCGGGGCAAAGTTCGAATATGGCGATTGTGACCCGCCTTGACCC
GATTTATGTCGATGTGAATTTGCCAACAGTCGATTTTTTACGGTTGCGGCGCGAGTTAAAAG
CGGGAACTTTGAAACGGAACGGCAATGATGCCGAAGTCTCCCTTATTCTCGATGATAATTCG
ACCTATAATCAAAAGGACGGCTGGCTTTAAGCGAAGTCAGTGCCGACACCCAGACATCGAC
CATTGTTGTTCGTGCGGTTTTCCCAAATCCTGAACATTTGTTGCTGCCCGGAATGTTTGTTT
ATGGTCGGATAGAAGAGGGCGTTGATCCGAACGCCTTGTTGGTTCCGCAAGAATCCGTTTTC
CGAAATAACCACGGTGATCCGATGTTATATGTCGTCAATAAAGACGACGTTATTGAAGCACG
CCCGATAAAAACCGGTGAAGCTATCGGAACGCAATGGGCTGTGACATCCGGTTTGCAAAAAG
GCGAACGCGTTTTGGTCTCTGGTCTTCAAAAAGTGAATATCGGCGACAAAGTTCATCCGACA
GAGGCTTCTCTTACCAAAGATGCCTCGCCAGAAAAGAAGGGCGGCAAGGCGTAA

B.  SEQ ID NO:10

MKRKIAPISVFAGSVLMMLTACHHQSQEAEPALQDVSFVTVKTQPLTVHSTLPGRTSAYEVA
EVRPQVNGVVLARYFNEGTDVKKGQPLFLINPAPYQATYDVNKAQLAHAEAQEKTAAAKLER
YKALAPAQAISRQDYDDALATDRAAKADIAQAKANIELSAVNLGYTRVTAPITGRIGRVLTT
VGALVTSGQSSNMAIVTRLDPIYVDVNLPTVDFLRLRRELKAGTLKRNGNDAEVSLILDDNS
TYNQKGRLALSEVSADTQTSTIVVRAVFPNPEHLLLPGMFVYGRIEEGVDPNALLVPQESVF
RNNHGDPMLYVVNKDDVIEARPIKTGEAIGTQWAVTSGLQKGERVLVSGLQKVNIGDKVHPT
EASLTKDASPEKKGGKA

Figure 6

A.    SEQ ID NO:11

ATGGCTCGCTATTTTATTGACCGCCCTGTTTTTGCTTGGGTTATCGGTCTTATCATCATGTTATTGGGTGCCTTGGCAA
TTGTTAAAATGCCTATTGCCCAATATCCGAATGTTGCCCCTCCGCAGATTGAGATCAGTGTGTCTTATCCGGGGGCGTC
GGCTGAAACGATCAATAATACCGTTGTTCGGCCTATCTTACAGCAGATGCATGGCATCGATAATCTGGAATATATTTCG
GCTTCTTCCTTTGCATCAGGTCAGATGACGATTGATTTGACCTTTGCACAAGGTACCGATGCCGATATCGCACAGGTGC
AAGTCCAGAATAAATTACAATTAGCGCAGCCTCGTTTGCCGTCGGATGTGGTCAATCAGGGTATTACGGTTAACCGTTC
TGCCAAAAGTTTTATGATGATTATGTCCTTCATCTCGACCGATGGCAGTATGTCCTATCAGGACATCAACGATTATGTG
GCATCGAATATTGCTGATCCGTTGAGCCGTGTTTCCGGTGTCGGCGATTACACTCTGTTCGGTTTTGAATATGCAATGC
GGGTCTGGTTAGATCCAGCAAAGCTCTACAAATATAATTTGACTGTAGCGGATGTCCAATCAGCTATTTCTACCCAGAA
TATTCAGCTTTCATCCGGTGAATTGGGCGGATTGCCTGCGGTTCAGGGTATTCGTTTGGATGCGACCATTATTGGCCCG
ACCCGTTTGACCTCGCCTGAAGAATTTAAAAATATTCTGGTCAAGGCTTTGCCGGATGGCGCCCAAATCAAATTGGGTG
ACATCGCTAAAGTAGAGTTGGGCGCGCAAAGCTATAACTTTGACGTGCGCTATAATAACCAGCCGGCTTCGGGTATTGC
GATCAAATTGGCACCGGGGGCGAACCAGCTTCAAACTGAAAAGTTGATCCGTCAGCGTTTGGCCGATTTGGAACCTTTC
TTCCCTCATGGTTTGAAGGTCGAATATCCGGTTGATACCAAGCCATTTGTGACGGCTTCTATCCATGAGGTTATTGAAA
CCTTGGTGGAAGCTATTGCGCTTGTTTTCTTGGTGATGCTGATCTTCTTGCAGAATTTCCGTGCTACCTTGATCCCGAC
GATTGCTGTGCCAGTGGTGTTGTTAGGCACCTTTGGTGTGCTTTCTGTTCTTGGTTTTTCAATCAATACTCTGACGATG
TTGGCAATGGTCTTGGCTGTTGTTGGTCGATGATGCCATCGTCGTTGTTGAAAATGTCGAACGTTTGATGCGAG
ATGAAAAGCTGCCCCCGAAAGAGGCGGCGAAGCGCTCGATGGATGAAATTCTGGTGCTTTGATCGGTATCGTCTTGGT
CTTGTCGGCCGTGTTCTTGCCTATGGCGGCCTTTTCAGGGTCAACGGGCGTTATCTATCGCCAATTCTCGATTACGATT
GTGGTGGCGATGGGGCTGTCTGTCCTTGTGGCGATGATTATGACGCCAGCCCTTTGCGCAACGATGTTAAAGCCGATTG
ACCATGACCAAGCCGATAAAAAGCCGGGTATCTTTGGTCGCTTGGCGAATGGCTTTAACCGTGCTTTTGACCGATTGAA
TAATGGTTATTTGGGTGGTGTGCTTGGTTGTTAGGACGTTCCGTCAAAGGCGGCATTGCCTTTTTGATCATTGTTTTC
GCCGTTGGTTATTTATTCACTCGCTTGCCAACCGGATTTTTGCCGGATGAAGATCAGGGTGAATTTATTGGTCAGGTGA
CCTTACCGCCGGGGGCGACCCAAGAACAAACGTCGGAAGCGGTGCGCAAGGTTAATGATTATCTTCTGTCCGCAGAGAA
AGACAGTGTCATATCTGTGATGACGGTTAGCGGTTTTAACTTTGGTGGTCAGGGACAAAATGCCGGTTCTTCTTCGTT
CGTTTGAAACCTTGGGATCAGCGTCCGAAAGCCTCGCAAAGTGCTTCGGCCTTGGCAATGCGGACGATGATGCATTTTT
GGGGTGATCCGTCATCGATGACTTTTGCCTTTAATATGCCTGCTGTCCGCGACTTGGGTAATGCCACCGGTTTTGACCT
TGAACTGGAAGATCGCGGTCATATCGGTCATGCAAAATTCCTTGAAGCCCGTAACATGTTATTGGCTTTGGCCTCGAAA
GATCCCCGCTTAAGTGGTGTCCGTCCGAATGGTATGGAAGATGCCCCTCAATATCATTTGACCGTTGATTACGGCAAAG
CTGTTATGATGGGATTGACCCCAAATGATGTGAATGTGGCCTTGCAGGGGTCTTTGGGGTCGATTTACGTCAATCAGTT
TATGCGGGATGACCGTGTGAAGCAGGTCTATTTAATGGGGGCACCGGAAGCGCGTATGCTGCCTTCCGATTTTTCCAAA
TGGTATCTGCGGAATAATGTCGGCACGATGGTTCCCTTTAGCGCCTTTATGACAGGAACATGGCAAACGGGCCCTCAGA
AAGTCGAAAATTATAACGGCTATAATTCTTTCGAAATTATGGGCGCGCCTGCACCGGGACATAGTTCGGGTGAAGCCAT
TCAGGCGATGACCGAGATCGTTCATAAATTGCCAGCTGGTGTTGGGCATGAATGGACAGGGTTATCTTTTGAAGAGCAG
GCGGCCGGTTCGTCCACCATGTCTCTTTATGCGATTTCCGCGATTGTGGTTCTGTTCTGTCTTGCCGCACTTTATGAAA
GCTGGGCCGTGCCGTTATCGGTTATTTTGGTTCTGCCTTTGGGTGTCTTGGGTGCCGTTGTAGCAACCTTGATGCGTGG
ATTGTCGAATGACGTCTATTTCCAGATCGGTTTGCTGACGACCGTTGGTTTGACCGTTAAAAACGCTATTTTGATTGTC
GAATTTGCAAAAGCCTTTTTCGATAATGGCGTGCCACTTTTGCAATCGGTGGTTCAAGCAGGCCGTGAGCGGTTACGGC
CTATTTTGATGACCTCTATTGCTTTTGTGTTGGGGGTTATTCCATTGAGCATCGCAACAGGGGCTTCTTCGGCAGCACG
TATCGCTATCGGAACGGCCGTTGTCGGCGGATGGTGACGGCTACCTTGTTGACGATTTTCTTTGTGCCTCTTTTCTTT
GTGGTGGTTTTGAAGCTGTTTCGGGTGAAACCGAACAAGCTGAATGCGGAGGAAGCAGCCTGA

B.    SEQ ID NO:12

MARYFIDRPVFAWVIGLIIMLLGALAIVKMPIAQYPNVAPPQIEISVSYPGASAETINNTVVRPILQQMHGIDNLEYIS
ASSFASGQMTIDLTFAQGTDADIAQVQVQNKLQLAQPRLPSDVVNQGITVNRSAKSFMMIMSFISTDGSMSYQDINDYV
ASNIADPLSRVSGVGDYTLFGFEYAMRVWLDPAKLYKYNLTVADVQSAISTQNIQLSSGELGGLPAVQGIRLDATIIGP
TRLTSPEEFKNILVKALPDGAQIKLGDIAKVELGAQSYNFDVRYNNQPASGIAIKLAPGANQLQTEKLIRQRLADLEPF
FPHGLKVEYPVDTKPFVTASIHEVIETLVEAIALVFLVMLIFLQNFRATLIPTIAVPVVLLGTFGVLSVLGFSINTLTM
LAMVLAVGLLVDDAIVVVENVERLMRDEKLPPKEAAKRSMDEISGALIGIVLVLSAVFLPMAAFSGSTGVIYRQFSITI
VVAMGLSVLVAMIMTPALCATMLKPIDHDQADKKPGIFGRLANGFNRAFDRLNNGYLGGVSWLLGRSVKGGIAFLIIVF
AVGYLFTRLPTGFLPDEDQGEFIGQVTLPPGATQEQTSEAVRKVNDYLLSAEKDSVISVMTVSGFNFGGQGQNAGSFFV
RLKPWDQRPKASQSASALAMRTMMHFWGDPSSMTFAFNMPAVRDLGNATGFDLELEDRGHIGHAKFLEARNMLLALASK
DPRLSGVRPNGMEDAPQYHLTVDYGKAVMMGLTPNDVNVALQGSLGSIYVNQFMRDDRVKQVYLMGAPEARMLPSDFSK
WYLRNNVGTMVPFSAFMTGTWQTGPQKVENYNGYNSFEIMGAPAPGHSSGEAIQAMTEIVHKLPAGVGHEWTGLSFEEQ
AAGSSTMSLYAISAIVVLFCLAALYESWAVPLSVILVLPLGVLGAVVATLMRGLSNDVYFQIGLLTTVGLTVKNAILIV
EFAKAFFDNGVPLLQSVVQAGRERLRPILMTSIAFVLGVIPLSIATGASSAARIAIGTAVVGGMVTATLLTIFFVPLFF
VVVLKLFRVKPNKLNAEEAA

Figure 7

A. SEQ ID NO:13

ATGACTTTATTTTCGGCTTCTTCGGCTCTGATTAAGCGGAGTAAAAAAGGATGGCGTTATCC
TGTAACGCTATTCTTATCGACTAATATTCTGTTGGCTGGATGCACGATGGCACCGAAATATC
ATCGTCCAGCAGCGTCTGTGGCACCGCAATGGCCGAAATCAGCGGCATTGCCTGCCGCTGAT
AACACTTCAATGAAGCCCCATCCTATGGCAGCCGATTTGGGGTGGCAGGATTTTTTCAAAGA
TGCGCGCCTAAAAGCCCTGATTACAATTGCGATCCGCGAAAACCGCGATTTGCGGTCAGCTA
TTCAGGCAATCGGTGAGGCGCAAGCCAGATATCGAGTGCAACGCGCGTCTTTATTGCCCGCA
ATCGGTGGCACTGGCGAAGTGATGTATCAGCAGCCTTCGGGTAAATCCGGTTTGAGTTTTGC
CCCAGGTGTCGGTGAAGATATTCCGCGTTTCCATTATTATTCGATGGGTATCGGTTTTTCTT
CTTATGAAATTGATATTTTTGGCCGCATCCGCAGTTTAAGCAAGGAGGCGGCTGAAAGAGCC
TTGATGCAGGAAGAGACTGCCAGAGGCACCTTGATCACGCTGATTTCGCAGGTGGCAAATAG
CTATATTGCTTGGTTGGCAGATCGAGAAACTTTGAATCTTGCCGAAGAAAGCTATCAGGCTG
CCAAGCGGAATTTGGATTTGACGCAGGCTTTGCTTGACCATGGTGAAGCGAGCCTTTTGACG
GTCAATCAAGCCGAAACCTTGTTCCAGCAAAAAGCAGATTTGCGGGAGCAGGCAAAGCGTCA
GATGGCATGGGAAGAAAATAATCTTGTCTTGCTGATCGGGCAGCCTTTGCCCGATAATTTGC
CGCCGCCTTTGCCCTTTGGTGAGCAAAATATCATCGAAGATTTATCGCCCGGTTTGCCTTCC
GATCTTTTGGAAAACCGGCCTGATATTCGAGCCGCGGAACATGATTTAAAGGCCGCTAATGC
GGATATTGGGGCAGCAAGAGCGGCTTTTTTCCCAAGGTTGTCTTTGACCTCTTCGGTTGGTA
ACTCAAGCCTTAAGCCTTCCCAGATTTTCACTACAGCGGCGAATACATGGGGATTCCAACCG
GAATTGACCGTGCCTATTTTTAACTGGGGGCAAAATCGCGCCAATTTGAGAATTTCCAAGGC
CGAGCGCGATATGAAGATCACGGCCTATCAAAAAGCAATCCAAAGTGCTTTTCGTGATGTGT
CGAATGCTTTAGTCGGACGCGATACTTATCGTCGTGAGGAAGTCGCCTTGACTCAAGCGGCG
GCGAAGGCTGAAAATAACTGGAATTTAGCGCGTTTGCGTCAGACTCAAGGCAGTGATTCCGC
CATCACTATGCTTAATTACGAGCAGACTTATTACCAAGCGGAATATCAGGCGATACAGAACA
GGGTTGCGCGTTATCAAAATTTGGTGACGCTCTATTCCGCTTTGGGCGGTGGGGTGAAAGAA
AAAGCGGTATCTTTGGATAAAACTGATAAAGCCGCCCATTCTGCCCATTGA

B. SEQ ID NO:14

MTLFSASSALIKRSKKGWRYPVTLFLSTNILLAGCTMAPKYHRPAASVAPQWPKSAALPAAD
NTSMKPHPMAADLGWQDFFKDARLKALITIAIRENRDLRSAIQAIGEAQARYRVQRASLLPA
IGGTGEVMYQQPSGKSGLSFAPGVGEDIPRFHYYSMGIGFSSYEIDIFGRIRSLSKEAAERA
LMQEETARGTLITLISQVANSYIAWLADRETLNLAEESYQAAKRNLDLTQALLDHGEASLLT
VNQAETLFQQKADLREQAKRQMAWEENNLVLLIGQPLPDNLPPPLPFGEQNIIEDLSPGLPS
DLLENRPDIRAAEHDLKAANADIGAARAAFFPRLSLTSSVGNSSLKPSQIFTTAANTWGFQP
ELTVPIFNWGQNRANLRISKAERDMKITAYQKAIQSAFRDVSNALVGRDTYRREEVALTQAA
AKAENNWNLARLRQTQGSDSAITMLNYEQTYYQAEYQAIQNRVARYQNLVTLYSALGGGVKE
KAVSLDKTDKAAHSAH

Figure 8

A. SEQ ID NO:15

ATGACACCCGATCAATCCGATAAAAGCGCCTCAAAACGCCATGTAGGGCGGCCTCCACAGCT
TGATGAAAAAAACGCTGTGCTCTTATCTTAAAAGCCGCTGCAACGGTGCTGCAAACGCATG
GCTATGATGGTTCCAGTATGGATCGGGTTGCCAGTCAGGCAGGCATGTCAAAAAAGACGGTG
TATCAAATGTTCCCGTCAAAAAAGATATTATTCACCAAATTACTCGAAGATCGGCTTTTCTC
GATTGAATGGCCAGAAGAAAAATCTGCGAAGACCCCGAAGAACATCTCTACTCTCTATTGA
TCGCCATTGCTCAAACTATTCTAAGGCCGGATCGGGTCTGCCTGCTTCGCATTTTAACCGTC
GAACATAAATCAGAAGAAATGCGGCATATTTTTAGTGATATTTTACAAGGACATACTGAAGA
CAATTTGACGCGCTGGTTCTCCGAACAACAAGACAAAGGTCGCTACCATATATCCGACCCCA
TAAAATATGCGGATATCATTTTTAATATGACCGTAGGCAGCCTGTTGCTCGATCGACTTTTC
GGTTTAGAAAAACGCCCTGTTGAAGACAATTTTCGAGATGCCATTTCAATTTTTTACGGGG
TATCCGTATCAATCCTGAAAATGAATAA

B. SEQ ID NO:16

MTPDQSDKSASKRHVGRPPQLDEKKRCALILKAAATVLQTHGYDGSSMDRVASQAGMSKKTV
YQMFPSKKILFTKLLEDRLFSIEWPEEKICEDPEEHLYSLLIAIAQTILRPDRVCLLRILTV
EHKSEEMRHIFSDILQGHTEDNLTRWFSEQQDKGRYHISDPIKYADIIFNMTVGSLLLDRLF
GLEKRPVEDNFRDAISIFLRGIRINPENE

SEQUENCE LISTING

```
<160> NUMBER OF SEQ ID NOS: 20

<210> SEQ ID NO 1
<211> LENGTH: 1263
<212> TYPE: DNA
<213> ORGANISM: Zymomonas mobilis
<220> FEATURE:
<221> NAME/KEY: CDS
<222> LOCATION: (1)..(1263)

<400> SEQUENCE: 1 atg act ttt ccc caa tca agg ctg aga aag gac tgc gtt att aaa ttt      48
Met Thr Phe Pro Gln Ser Arg Leu Arg Lys Asp Cys Val Ile Lys Phe
1               5                   10                  15 atc cct gtc tat cta tcc gga tta tca atc ctg gct cta ttt att att      96
Ile Pro Val Tyr Leu Ser Gly Leu Ser Ile Leu Ala Leu Phe Ile Ile
            20                  25                  30 gcc gtc agt cat gtt tct gtc ggg tgg ccg atc ttg tcg ctt atg ctg     144
Ala Val Ser His Val Ser Val Gly Trp Pro Ile Leu Ser Leu Met Leu
        35                  40                  45 att gtt atc ctt tgg gga tgg tgg ttt aaa aat att tcc gaa gcg tct     192
Ile Val Ile Leu Trp Gly Trp Trp Phe Lys Asn Ile Ser Glu Ala Ser
    50                  55                  60 acc ccc ttc cct gaa agt aaa agc gga aat agc ctt acg gat cct gcc     240
Thr Pro Phe Pro Glu Ser Lys Ser Gly Asn Ser Leu Thr Asp Pro Ala
65                  70                  75                  80 tat cct ttt tct caa gcg aca gcg gca gat att att ata gct atg gat     288
Tyr Pro Phe Ser Gln Ala Thr Ala Ala Asp Ile Ile Ile Ala Met Asp
```

-continued

```
                      85                  90                  95
gaa cca gct tta ctg gtc aat cag ggt caa gtt gaa gtg gct aat cgt    336
Glu Pro Ala Leu Leu Val Asn Gln Gly Gln Val Glu Val Ala Asn Arg
            100                 105                 110 gcc gct gaa aat ttg tta ggg atg cat atc gaa gga ggc gac atc aga    384
Ala Ala Glu Asn Leu Leu Gly Met His Ile Glu Gly Gly Asp Ile Arg
        115                 120                 125 atg gct att cgc cat cct gct gct atc cgt ctt tta acc gag ccg ctt    432
Met Ala Ile Arg His Pro Ala Ala Ile Arg Leu Leu Thr Glu Pro Leu
130                 135                 140 gat aat atg act cct gtt tta ctt gcc gga ttg gga ggc gtt aat cgt    480
Asp Asn Met Thr Pro Val Leu Leu Ala Gly Leu Gly Gly Val Asn Arg
145                 150                 155                 160 cgc tgg gaa tta tac gct tat cct ttg aac gaa gaa caa cgg ctc att    528
Arg Trp Glu Leu Tyr Ala Tyr Pro Leu Asn Glu Glu Gln Arg Leu Ile
                165                 170                 175 ttg ttg cgc gat caa agt acg gct cat tta acg gaa cag gtt aga ata    576
Leu Leu Arg Asp Gln Ser Thr Ala His Leu Thr Glu Gln Val Arg Ile
            180                 185                 190 gac ttt gtt gcg aat act agt cac gaa tta cgg aca ccg ctc gcg act    624
Asp Phe Val Ala Asn Thr Ser His Glu Leu Arg Thr Pro Leu Ala Thr
        195                 200                 205 tta agc ggg ttt att gag aca tta gaa gat gat gat gtc att aaa gag    672
Leu Ser Gly Phe Ile Glu Thr Leu Glu Asp Asp Asp Val Ile Lys Glu
210                 215                 220 cgc gat acg cgt cat cat ttt ttg tct att atg gcg cgt gaa gcc aaa    720
Arg Asp Thr Arg His His Phe Leu Ser Ile Met Ala Arg Glu Ala Lys
225                 230                 235                 240 aga atg caa aat ttg gtt gat gac ttg atg tct ctt tct cgg att gaa    768
Arg Met Gln Asn Leu Val Asp Asp Leu Met Ser Leu Ser Arg Ile Glu
                245                 250                 255 gcc gga aaa ttt tca tta ccc cat gat att gtt cat atg tcg cct gtg    816
Ala Gly Lys Phe Ser Leu Pro His Asp Ile Val His Met Ser Pro Val
            260                 265                 270 gtt gaa gag gtc gtg tct aat att cag gca tcg gga cag gca aaa gcc    864
Val Glu Glu Val Val Ser Asn Ile Gln Ala Ser Gly Gln Ala Lys Ala
        275                 280                 285 acc caa atc aca ctc gaa aat cat ttg tcc agt gat agc cta cag ggt    912
Thr Gln Ile Thr Leu Glu Asn His Leu Ser Ser Asp Ser Leu Gln Gly
290                 295                 300 gac cgc gcc gag tta acg cag ctc ctt tat aac att atc ggc aat gcc    960
Asp Arg Ala Glu Leu Thr Gln Leu Leu Tyr Asn Ile Ile Gly Asn Ala
305                 310                 315                 320 tta aaa tat ggt cgt aaa gat gga ata att aaa gtc gcg ctc gat aat    1008
Leu Lys Tyr Gly Arg Lys Asp Gly Ile Ile Lys Val Ala Leu Asp Asn
                325                 330                 335 act gac gat cat aga ata aaa tta gct att gca gat gaa ggc gat ggt    1056
Thr Asp Asp His Arg Ile Lys Leu Ala Ile Ala Asp Glu Gly Asp Gly
            340                 345                 350 att ccg ttt cat cat atc ccg cgc cta acg gaa cgc ttc tat cgg gtg    1104
Ile Pro Phe His His Ile Pro Arg Leu Thr Glu Arg Phe Tyr Arg Val
        355                 360                 365 gat aac agc cgt agt cgc gct tta ggg gga aca gga ttg ggc cta gcc    1152
Asp Asn Ser Arg Ser Arg Ala Leu Gly Gly Thr Gly Leu Gly Leu Ala
370                 375                 380 ata gta aaa caa atc gtc gag cat cat cgc gga gaa tta ctg ata gac    1200
Ile Val Lys Gln Ile Val Glu His His Arg Gly Glu Leu Leu Ile Asp
385                 390                 395                 400 agc ctc ccc ggt aaa ggg acg acg gta acc gtt ttc ttg cca acg acc    1248
```

```
Ser Leu Pro Gly Lys Gly Thr Thr Val Thr Val Phe Leu Pro Thr Thr
            405             410             415 gat ttt ttc cct gaa                                              1263
Asp Phe Phe Pro Glu
        420

<210> SEQ ID NO 2
<211> LENGTH: 421
<212> TYPE: PRT
<213> ORGANISM: Zymomonas mobilis

<400> SEQUENCE: 2

Met Thr Phe Pro Gln Ser Arg Leu Arg Lys Asp Cys Val Ile Lys Phe
1               5                   10                  15

Ile Pro Val Tyr Leu Ser Gly Leu Ser Ile Leu Ala Leu Phe Ile Ile
            20                  25                  30

Ala Val Ser His Val Ser Val Gly Trp Pro Ile Leu Ser Leu Met Leu
        35                  40                  45

Ile Val Ile Leu Trp Gly Trp Trp Phe Lys Asn Ile Ser Glu Ala Ser
    50                  55                  60

Thr Pro Phe Pro Glu Ser Lys Ser Gly Asn Ser Leu Thr Asp Pro Ala
65                  70                  75                  80

Tyr Pro Phe Ser Gln Ala Thr Ala Ala Asp Ile Ile Ala Met Asp
                85                  90                  95

Glu Pro Ala Leu Leu Val Asn Gln Gly Gln Val Glu Val Ala Asn Arg
            100                 105                 110

Ala Ala Glu Asn Leu Leu Gly Met His Ile Glu Gly Gly Asp Ile Arg
        115                 120                 125

Met Ala Ile Arg His Pro Ala Ala Ile Arg Leu Leu Thr Glu Pro Leu
    130                 135                 140

Asp Asn Met Thr Pro Val Leu Leu Ala Gly Leu Gly Gly Val Asn Arg
145                 150                 155                 160

Arg Trp Glu Leu Tyr Ala Tyr Pro Leu Asn Glu Glu Gln Arg Leu Ile
                165                 170                 175

Leu Leu Arg Asp Gln Ser Thr Ala His Leu Thr Glu Gln Val Arg Ile
            180                 185                 190

Asp Phe Val Ala Asn Thr Ser His Glu Leu Arg Thr Pro Leu Ala Thr
        195                 200                 205

Leu Ser Gly Phe Ile Glu Thr Leu Glu Asp Asp Val Ile Lys Glu
    210                 215                 220

Arg Asp Thr Arg His His Phe Leu Ser Ile Met Ala Arg Glu Ala Lys
225                 230                 235                 240

Arg Met Gln Asn Leu Val Asp Asp Leu Met Ser Leu Ser Arg Ile Glu
                245                 250                 255

Ala Gly Lys Phe Ser Leu Pro His Asp Ile Val His Met Ser Pro Val
            260                 265                 270

Val Glu Glu Val Val Ser Asn Ile Gln Ala Ser Gly Gln Ala Lys Ala
        275                 280                 285

Thr Gln Ile Thr Leu Glu Asn His Leu Ser Ser Asp Ser Leu Gln Gly
    290                 295                 300

Asp Arg Ala Glu Leu Thr Gln Leu Leu Tyr Asn Ile Ile Gly Asn Ala
305                 310                 315                 320

Leu Lys Tyr Gly Arg Lys Asp Gly Ile Ile Lys Val Ala Leu Asp Asn
                325                 330                 335

Thr Asp Asp His Arg Ile Lys Leu Ala Ile Ala Asp Glu Gly Asp Gly
```

```
                340                 345                 350
Ile Pro Phe His His Ile Pro Arg Leu Thr Glu Arg Phe Tyr Arg Val
            355                 360                 365

Asp Asn Ser Arg Ser Arg Ala Leu Gly Gly Thr Gly Leu Gly Leu Ala
        370                 375                 380

Ile Val Lys Gln Ile Val Glu His His Arg Gly Glu Leu Leu Ile Asp
385                 390                 395                 400

Ser Leu Pro Gly Lys Gly Thr Thr Val Thr Val Phe Leu Pro Thr Thr
                405                 410                 415

Asp Phe Phe Pro Glu
            420

<210> SEQ ID NO 3
<211> LENGTH: 600
<212> TYPE: DNA
<213> ORGANISM: Zymomonas mobilis
<220> FEATURE:
<221> NAME/KEY: CDS
<222> LOCATION: (1)..(600)

<400> SEQUENCE: 3 atg gat atc cgt att tcc ggc cat cag att gat aca ggc gcg gct tta    48
Met Asp Ile Arg Ile Ser Gly His Gln Ile Asp Thr Gly Ala Ala Leu
1               5                   10                  15 aga gaa tat gtc aat gac cat ctt agc cag atc gtc agc aaa tat ttc    96
Arg Glu Tyr Val Asn Asp His Leu Ser Gln Ile Val Ser Lys Tyr Phe
                20                  25                  30 ccc aaa tgc cta agc gcc tct gtc act ttc ggt aat cgt cgc cac gct   144
Pro Lys Cys Leu Ser Ala Ser Val Thr Phe Gly Asn Arg Arg His Ala
            35                  40                  45 att att tcc tgc gat att att atc cat gcc atg cgg gat att att ctg   192
Ile Ile Ser Cys Asp Ile Ile Ile His Ala Met Arg Asp Ile Ile Leu
        50                  55                  60 aaa gca ggc ggc ata gac aaa gac gcc cat gcc gct ttc gat cag gcc   240
Lys Ala Gly Gly Ile Asp Lys Asp Ala His Ala Ala Phe Asp Gln Ala
65                  70                  75                  80 gcc gcc aag att gaa aaa caa tta cgg cga cat cac cga cgt tta cag   288
Ala Ala Lys Ile Glu Lys Gln Leu Arg Arg His His Arg Arg Leu Gln
                85                  90                  95 acc cgc gtc cag caa aat acg cct tct att gat gaa gcc gct atc gcc   336
Thr Arg Val Gln Gln Asn Thr Pro Ser Ile Asp Glu Ala Ala Ile Ala
            100                 105                 110 ctt acg gag gca aca gcc aag gcg gat cag gat aac gcg cat tat acg   384
Leu Thr Glu Ala Thr Ala Lys Ala Asp Gln Asp Asn Ala His Tyr Thr
        115                 120                 125 gtc ttt gac att gaa gag gat gaa aaa gag caa ggc gat cat cct ccc   432
Val Phe Asp Ile Glu Glu Asp Glu Lys Glu Gln Gly Asp His Pro Pro
130                 135                 140 gtc att gcc gaa atg cag gtt gat att cca aca gcc agc gtt tcc gat   480
Val Ile Ala Glu Met Gln Val Asp Ile Pro Thr Ala Ser Val Ser Asp
                145                 150                 155                 160 gct gtt ttg atg ctc gat ctt cgc aac acg acg gct ttg ctc ttc gtg   528
Ala Val Leu Met Leu Asp Leu Arg Asn Thr Thr Ala Leu Leu Phe Val
            165                 170                 175 aac agc aaa tcg ggt cat cat aat atg gtt tat cgt cgg gta gat ggt   576
Asn Ser Lys Ser Gly His His Asn Met Val Tyr Arg Arg Val Asp Gly
        180                 185                 190 acc atc ggt tgg gtt gag ccg cga                                    600
Thr Ile Gly Trp Val Glu Pro Arg
195                 200
```

<210> SEQ ID NO 4
<211> LENGTH: 200
<212> TYPE: PRT
<213> ORGANISM: Zymomonas mobilis

<400> SEQUENCE: 4

```
Met Asp Ile Arg Ile Ser Gly His Gln Ile Asp Thr Gly Ala Ala Leu
1               5                   10                  15

Arg Glu Tyr Val Asn Asp His Leu Ser Gln Ile Val Ser Lys Tyr Phe
            20                  25                  30

Pro Lys Cys Leu Ser Ala Ser Val Thr Phe Gly Asn Arg Arg His Ala
        35                  40                  45

Ile Ile Ser Cys Asp Ile Ile His Ala Met Arg Asp Ile Ile Leu
    50                  55                  60

Lys Ala Gly Gly Ile Asp Lys Asp Ala His Ala Ala Phe Asp Gln Ala
65                  70                  75                  80

Ala Ala Lys Ile Glu Lys Gln Leu Arg Arg His His Arg Arg Leu Gln
                85                  90                  95

Thr Arg Val Gln Gln Asn Thr Pro Ser Ile Asp Glu Ala Ala Ile Ala
            100                 105                 110

Leu Thr Glu Ala Thr Ala Lys Ala Asp Gln Asp Asn Ala His Tyr Thr
        115                 120                 125

Val Phe Asp Ile Glu Glu Asp Glu Lys Glu Gln Gly Asp His Pro Pro
    130                 135                 140

Val Ile Ala Glu Met Gln Val Asp Ile Pro Thr Ala Ser Val Ser Asp
145                 150                 155                 160

Ala Val Leu Met Leu Asp Leu Arg Asn Thr Thr Ala Leu Leu Phe Val
                165                 170                 175

Asn Ser Lys Ser Gly His His Asn Met Val Tyr Arg Arg Val Asp Gly
            180                 185                 190

Thr Ile Gly Trp Val Glu Pro Arg
        195                 200
```

<210> SEQ ID NO 5
<211> LENGTH: 1983
<212> TYPE: DNA
<213> ORGANISM: Zymomonas mobilis
<220> FEATURE:
<221> NAME/KEY: CDS
<222> LOCATION: (1)..(1983)

<400> SEQUENCE: 5

```
atg cct aat gca gag ttt gat ttc agg cct atg ttt ccg aat aaa aag      48
Met Pro Asn Ala Glu Phe Asp Phe Arg Pro Met Phe Pro Asn Lys Lys
1               5                   10                  15 acg ccg ttg tta gac aag atc aag aca ccg gca gaa ttg cgt caa tta      96
Thr Pro Leu Leu Asp Lys Ile Lys Thr Pro Ala Glu Leu Arg Gln Leu
            20                  25                  30 gat cgc aac agc ctc cgg caa ttg gcg gat gaa tta cgg aaa gag acc     144
Asp Arg Asn Ser Leu Arg Gln Leu Ala Asp Glu Leu Arg Lys Glu Thr
        35                  40                  45 atc tcg gca gtg ggt gtg acc ggc gga cat ctc ggt tcc ggt ctg ggg     192
Ile Ser Ala Val Gly Val Thr Gly Gly His Leu Gly Ser Gly Leu Gly
    50                  55                  60 gtt atc gaa tta acg gta gct ctt cat tat gtt ttc aac acg ccc aaa     240
Val Ile Glu Leu Thr Val Ala Leu His Tyr Val Phe Asn Thr Pro Lys
65                  70                  75                  80
```

```
gac gct ttg gtc tgg gat gtt ggg cat caa acc tat cct cac aag att       288
Asp Ala Leu Val Trp Asp Val Gly His Gln Thr Tyr Pro His Lys Ile
                85                  90                  95 tta aca ggt cgc cgt gat cgt att cgg aca ttg cgg caa cgt gac ggc       336
Leu Thr Gly Arg Arg Asp Arg Ile Arg Thr Leu Arg Gln Arg Asp Gly
                100                 105                 110 tta tcg ggc ttt acg cag cgc gcg gag agc gaa tat gac gct ttt gga       384
Leu Ser Gly Phe Thr Gln Arg Ala Glu Ser Glu Tyr Asp Ala Phe Gly
                115                 120                 125 gca gcg cat agt tcg act tct att tct gcg gcg ctc ggc ttt gcg atg       432
Ala Ala His Ser Ser Thr Ser Ile Ser Ala Ala Leu Gly Phe Ala Met
                130                 135                 140 gcc agc aaa tta tcc gac agc gac gac aaa gcg gtt gcg att atc ggt       480
Ala Ser Lys Leu Ser Asp Ser Asp Asp Lys Ala Val Ala Ile Ile Gly
145                 150                 155                 160 gat ggc tcg atg acg gca ggc atg gct tat gaa gcc atg aat aac gcc       528
Asp Gly Ser Met Thr Ala Gly Met Ala Tyr Glu Ala Met Asn Asn Ala
                165                 170                 175 aag gcg gcg ggt aag cgc ctg att gtc att ttg aat gac aat gaa atg       576
Lys Ala Ala Gly Lys Arg Leu Ile Val Ile Leu Asn Asp Asn Glu Met
                180                 185                 190 tcg att tca ccg ccg gtg ggt gcc tta tcg tct tat ttg agc cgc ctg       624
Ser Ile Ser Pro Pro Val Gly Ala Leu Ser Ser Tyr Leu Ser Arg Leu
                195                 200                 205 att tcc tca cgg cct ttc atg aat ttg cgc gat atc atg cgc ggt gtt       672
Ile Ser Ser Arg Pro Phe Met Asn Leu Arg Asp Ile Met Arg Gly Val
210                 215                 220 gtc aac cgg atg cca aaa ggc ttg gca acg gct gcc cgc aag gct gat       720
Val Asn Arg Met Pro Lys Gly Leu Ala Thr Ala Ala Arg Lys Ala Asp
225                 230                 235                 240 gaa tat gcg cgt ggt atg gca acc ggt ggc acc ttc ttt gaa gag ctg       768
Glu Tyr Ala Arg Gly Met Ala Thr Gly Gly Thr Phe Phe Glu Glu Leu
                245                 250                 255 ggc ttt tac tat gtt ggc ccc gta gat ggt cat aat tta gat cag ctc       816
Gly Phe Tyr Tyr Val Gly Pro Val Asp Gly His Asn Leu Asp Gln Leu
                260                 265                 270 att ccg gtt ttg gaa aat gtc cgc gat gcc aag gac ggc ccc att ttg       864
Ile Pro Val Leu Glu Asn Val Arg Asp Ala Lys Asp Gly Pro Ile Leu
                275                 280                 285 gtg cat gtc gtc acc cgc aaa ggc caa ggc tat gct ccg gct gaa gcg       912
Val His Val Val Thr Arg Lys Gly Gln Gly Tyr Ala Pro Ala Glu Ala
                290                 295                 300 gcc aag gac aaa tat cac gcc gtg cag cgc ttg gat gtg gtt tcc ggc       960
Ala Lys Asp Lys Tyr His Ala Val Gln Arg Leu Asp Val Val Ser Gly
305                 310                 315                 320 aag cag gcg aaa gcg ccc cca ggg cct ccc agc tat acc tct gtt ttc      1008
Lys Gln Ala Lys Ala Pro Pro Gly Pro Pro Ser Tyr Thr Ser Val Phe
                325                 330                 335 tcg gaa cag ctg atc aag gaa gct aag caa gac gat aag att gtg acc      1056
Ser Glu Gln Leu Ile Lys Glu Ala Lys Gln Asp Asp Lys Ile Val Thr
                340                 345                 350 att acg gca gct atg ccg act ggc acc ggt ctt gat cgc ttc cag caa      1104
Ile Thr Ala Ala Met Pro Thr Gly Thr Gly Leu Asp Arg Phe Gln Gln
                355                 360                 365 tat ttt cct gaa aga atg ttt gat gtc ggt att gcc gaa caa cat gcc      1152
Tyr Phe Pro Glu Arg Met Phe Asp Val Gly Ile Ala Glu Gln His Ala
370                 375                 380 gta acc ttt gcg gct ggt ttg gcg gct gcc ggt tac aag cct ttc tgt      1200
Val Thr Phe Ala Ala Gly Leu Ala Ala Ala Gly Tyr Lys Pro Phe Cys
385                 390                 395                 400
```

```
tgt ctc tat tcg acc ttc ttg cag cgc ggc tat gac cag tta gtg cat    1248
Cys Leu Tyr Ser Thr Phe Leu Gln Arg Gly Tyr Asp Gln Leu Val His
            405                 410                 415 gat gtc gct atc cag aat ttg ccg gtg cgc ttc gcc gtc gat cgt gcg    1296
Asp Val Ala Ile Gln Asn Leu Pro Val Arg Phe Ala Val Asp Arg Ala
        420                 425                 430 ggt ctt gtc ggt gcc gat ggg gca acc cat gcg ggt agc ttc gac ctc    1344
Gly Leu Val Gly Ala Asp Gly Ala Thr His Ala Gly Ser Phe Asp Leu
    435                 440                 445 gcc ttt atg gtt aat cta ccg aat atg gtc gtg atg gcg cct tcc gat    1392
Ala Phe Met Val Asn Leu Pro Asn Met Val Val Met Ala Pro Ser Asp
450                 455                 460 gaa cgg gaa ttg gcc aat atg gtg cat agc atg gcg cat tat gac caa    1440
Glu Arg Glu Leu Ala Asn Met Val His Ser Met Ala His Tyr Asp Gln
465                 470                 475                 480 ggc ccg atc tcg gtg cgt tat ccg cgt ggt aat ggt gtg ggt gtc tcc    1488
Gly Pro Ile Ser Val Arg Tyr Pro Arg Gly Asn Gly Val Gly Val Ser
            485                 490                 495 ttg gaa ggc gaa aag gaa att ctg cct atc ggg aaa ggt cgc ctg atc    1536
Leu Glu Gly Glu Lys Glu Ile Leu Pro Ile Gly Lys Gly Arg Leu Ile
        500                 505                 510 cgt cgc ggt aaa aag gtt gct atc cta tct ctc ggc act cga ttg gaa    1584
Arg Arg Gly Lys Lys Val Ala Ile Leu Ser Leu Gly Thr Arg Leu Glu
    515                 520                 525 gaa tcc ttg aag gct gct gat cgg ctt gat gct caa ggt ttg tcg aca    1632
Glu Ser Leu Lys Ala Ala Asp Arg Leu Asp Ala Gln Gly Leu Ser Thr
530                 535                 540 tcg gtt gct gat atg cgt ttt gct aag ccc ttg gat gaa gcg ctg acc    1680
Ser Val Ala Asp Met Arg Phe Ala Lys Pro Leu Asp Glu Ala Leu Thr
545                 550                 555                 560 cgc caa ctt cta aaa agc cat cag gtc att att acc att gaa gaa ggc    1728
Arg Gln Leu Leu Lys Ser His Gln Val Ile Ile Thr Ile Glu Glu Gly
            565                 570                 575 gct ttg ggt ggt ttt gca acc caa gtc ctg acg atg gct tcg gat gaa    1776
Ala Leu Gly Gly Phe Ala Thr Gln Val Leu Thr Met Ala Ser Asp Glu
        580                 585                 590 ggc ctg atg gat gac gga ttg aaa atc cgc acc ctg cgt ctg ccg gat    1824
Gly Leu Met Asp Asp Gly Leu Lys Ile Arg Thr Leu Arg Leu Pro Asp
    595                 600                 605 cgg ttc cag ccg caa gac aag caa gaa cgg caa tat gcc gaa gct ggt    1872
Arg Phe Gln Pro Gln Asp Lys Gln Glu Arg Gln Tyr Ala Glu Ala Gly
610                 615                 620 ctt gat gct gat ggc atc gtt gct gcc gta acg gct gca tta caa cgg    1920
Leu Asp Ala Asp Gly Ile Val Ala Ala Val Thr Ala Ala Leu Gln Arg
625                 630                 635                 640 aac tca aag cct gtc gaa gtc gtt gag ctg act aca aaa gta aca gaa    1968
Asn Ser Lys Pro Val Glu Val Val Glu Leu Thr Thr Lys Val Thr Glu
            645                 650                 655 gat atg act tta tga                                                1983
Asp Met Thr Leu
        660

<210> SEQ ID NO 6
<211> LENGTH: 660
<212> TYPE: PRT
<213> ORGANISM: Zymomonas mobilis

<400> SEQUENCE: 6

Met Pro Asn Ala Glu Phe Asp Phe Arg Pro Met Phe Pro Asn Lys Lys
1               5                   10                  15
```

```
Thr Pro Leu Leu Asp Lys Ile Lys Thr Pro Ala Glu Leu Arg Gln Leu
            20                  25                  30

Asp Arg Asn Ser Leu Arg Gln Leu Ala Asp Glu Leu Arg Lys Glu Thr
        35                  40                  45

Ile Ser Ala Val Gly Val Thr Gly Gly His Leu Gly Ser Gly Leu Gly
50                  55                  60

Val Ile Glu Leu Thr Val Ala Leu His Tyr Val Phe Asn Thr Pro Lys
65                  70                  75                  80

Asp Ala Leu Val Trp Asp Val Gly His Gln Thr Tyr Pro His Lys Ile
                85                  90                  95

Leu Thr Gly Arg Arg Asp Arg Ile Arg Thr Leu Arg Gln Arg Asp Gly
            100                 105                 110

Leu Ser Gly Phe Thr Gln Arg Ala Glu Ser Glu Tyr Asp Ala Phe Gly
        115                 120                 125

Ala Ala His Ser Ser Thr Ser Ile Ser Ala Ala Leu Gly Phe Ala Met
130                 135                 140

Ala Ser Lys Leu Ser Asp Ser Asp Lys Ala Val Ala Ile Ile Gly
145                 150                 155                 160

Asp Gly Ser Met Thr Ala Gly Met Ala Tyr Glu Ala Met Asn Asn Ala
                165                 170                 175

Lys Ala Ala Gly Lys Arg Leu Ile Val Ile Leu Asn Asp Asn Glu Met
            180                 185                 190

Ser Ile Ser Pro Pro Val Gly Ala Leu Ser Ser Tyr Leu Ser Arg Leu
        195                 200                 205

Ile Ser Ser Arg Pro Phe Met Asn Leu Arg Asp Ile Met Arg Gly Val
210                 215                 220

Val Asn Arg Met Pro Lys Gly Leu Ala Thr Ala Ala Arg Lys Ala Asp
225                 230                 235                 240

Glu Tyr Ala Arg Gly Met Ala Thr Gly Gly Thr Phe Phe Glu Glu Leu
                245                 250                 255

Gly Phe Tyr Tyr Val Gly Pro Val Asp Gly His Asn Leu Asp Gln Leu
            260                 265                 270

Ile Pro Val Leu Glu Asn Val Arg Asp Ala Lys Asp Gly Pro Ile Leu
        275                 280                 285

Val His Val Val Thr Arg Lys Gly Gln Gly Tyr Ala Pro Ala Glu Ala
290                 295                 300

Ala Lys Asp Lys Tyr His Ala Val Gln Arg Leu Asp Val Val Ser Gly
305                 310                 315                 320

Lys Gln Ala Lys Ala Pro Pro Gly Pro Pro Ser Tyr Thr Ser Val Phe
                325                 330                 335

Ser Glu Gln Leu Ile Lys Glu Ala Lys Gln Asp Asp Lys Ile Val Thr
            340                 345                 350

Ile Thr Ala Ala Met Pro Thr Gly Thr Gly Leu Asp Arg Phe Gln Gln
        355                 360                 365

Tyr Phe Pro Glu Arg Met Phe Asp Val Gly Ile Ala Glu Gln His Ala
370                 375                 380

Val Thr Phe Ala Ala Gly Leu Ala Ala Ala Gly Tyr Lys Pro Phe Cys
385                 390                 395                 400

Cys Leu Tyr Ser Thr Phe Leu Gln Arg Gly Tyr Asp Gln Leu Val His
                405                 410                 415

Asp Val Ala Ile Gln Asn Leu Pro Val Arg Phe Ala Val Asp Arg Ala
            420                 425                 430
```

```
Gly Leu Val Gly Ala Asp Gly Ala Thr His Ala Gly Ser Phe Asp Leu
            435                 440                 445

Ala Phe Met Val Asn Leu Pro Asn Met Val Val Met Ala Pro Ser Asp
450                 455                 460

Glu Arg Glu Leu Ala Asn Met Val His Ser Met Ala His Tyr Asp Gln
465                 470                 475                 480

Gly Pro Ile Ser Val Arg Tyr Pro Arg Gly Asn Gly Val Gly Val Ser
                485                 490                 495

Leu Glu Gly Glu Lys Glu Ile Leu Pro Ile Gly Lys Gly Arg Leu Ile
            500                 505                 510

Arg Arg Gly Lys Lys Val Ala Ile Leu Ser Leu Gly Thr Arg Leu Glu
        515                 520                 525

Glu Ser Leu Lys Ala Ala Asp Arg Leu Asp Ala Gln Gly Leu Ser Thr
    530                 535                 540

Ser Val Ala Asp Met Arg Phe Ala Lys Pro Leu Asp Glu Ala Leu Thr
545                 550                 555                 560

Arg Gln Leu Leu Lys Ser His Gln Val Ile Ile Thr Ile Glu Glu Gly
                565                 570                 575

Ala Leu Gly Gly Phe Ala Thr Gln Val Leu Thr Met Ala Ser Asp Glu
            580                 585                 590

Gly Leu Met Asp Asp Gly Leu Lys Ile Arg Thr Leu Arg Leu Pro Asp
        595                 600                 605

Arg Phe Gln Pro Gln Asp Lys Gln Glu Arg Gln Tyr Ala Glu Ala Gly
    610                 615                 620

Leu Asp Ala Asp Gly Ile Val Ala Ala Val Thr Ala Ala Leu Gln Arg
625                 630                 635                 640

Asn Ser Lys Pro Val Glu Val Val Glu Leu Thr Thr Lys Val Thr Glu
                645                 650                 655

Asp Met Thr Leu
            660

<210> SEQ ID NO 7
<211> LENGTH: 1950
<212> TYPE: DNA
<213> ORGANISM: Zymomonas mobilis
<220> FEATURE:
<221> NAME/KEY: CDS
<222> LOCATION: (1)..(1950)

<400> SEQUENCE: 7 atg ttt ccg aat gac aag acg ccg ctg tta gac aag atc aag aca ccg       48
Met Phe Pro Asn Asp Lys Thr Pro Leu Leu Asp Lys Ile Lys Thr Pro
1               5                   10                  15 gca gaa ttg cgt caa tta gat cgc aac agc ctc cgg caa ttg gcg gat       96
Ala Glu Leu Arg Gln Leu Asp Arg Asn Ser Leu Arg Gln Leu Ala Asp
                20                  25                  30 gaa tta cgg aaa gag acc atc tcg gca gtg ggt gtg acc ggc gga cat      144
Glu Leu Arg Lys Glu Thr Ile Ser Ala Val Gly Val Thr Gly Gly His
            35                  40                  45 ctc ggt tcc ggt ctg ggg gtt atc gaa tta acg gta gcc ctt cac tat      192
Leu Gly Ser Gly Leu Gly Val Ile Glu Leu Thr Val Ala Leu His Tyr
    50                  55                  60 gtt ttc aac acg ccc aaa gac gct tta gtc tgg gat gtt ggg cat caa      240
Val Phe Asn Thr Pro Lys Asp Ala Leu Val Trp Asp Val Gly His Gln
65                  70                  75                  80 acc tat cct cac aag att tta aca ggt cgc cgc gat cgt att cgg aca      288
Thr Tyr Pro His Lys Ile Leu Thr Gly Arg Arg Asp Arg Ile Arg Thr
                85                  90                  95
```

-continued

| | |
|---|---|
| ttg cgg caa cgt gac ggc tta tcg ggc ttt acg cag cgc gcg gag agc<br>Leu Arg Gln Arg Asp Gly Leu Ser Gly Phe Thr Gln Arg Ala Glu Ser<br>100                     105                   110 | 336 |
| gaa tat gac gct ttt gga gcc gcg cat agt tcg act tct att tct gcg<br>Glu Tyr Asp Ala Phe Gly Ala Ala His Ser Ser Thr Ser Ile Ser Ala<br>       115                   120                   125 | 384 |
| gcg ctc ggc ttt gcg atg gcc agc aaa tta tcc gac agc gac gac aaa<br>Ala Leu Gly Phe Ala Met Ala Ser Lys Leu Ser Asp Ser Asp Asp Lys<br>130                     135                   140 | 432 |
| gcg gtt gcg att atc ggt gat ggc tcg atg acg gca ggc atg gct tat<br>Ala Val Ala Ile Ile Gly Asp Gly Ser Met Thr Ala Gly Met Ala Tyr<br>145                     150                   155                   160 | 480 |
| gaa gcc atg aat aac gcc aag gcg gcg ggt aag cgc ctg att gtc att<br>Glu Ala Met Asn Asn Ala Lys Ala Ala Gly Lys Arg Leu Ile Val Ile<br>                165                   170                   175 | 528 |
| ttg aat gac aat gaa atg tcg att tca ccg ccg gtt ggt gcc tta tcg<br>Leu Asn Asp Asn Glu Met Ser Ile Ser Pro Pro Val Gly Ala Leu Ser<br>                180                   185                   190 | 576 |
| tct tat ttg agc cgc ctg att tcc tca cgg cct ttc atg aat ttg cgc<br>Ser Tyr Leu Ser Arg Leu Ile Ser Ser Arg Pro Phe Met Asn Leu Arg<br>                195                   200                   205 | 624 |
| gat atc atg cgc ggc gtt gtt aac cgg atg cca aaa ggc ttg gca acg<br>Asp Ile Met Arg Gly Val Val Asn Arg Met Pro Lys Gly Leu Ala Thr<br>210                     215                   220 | 672 |
| gct gcc cgc aag gct gat gaa tat gcg cgt ggt atg gca acc ggt ggc<br>Ala Ala Arg Lys Ala Asp Glu Tyr Ala Arg Gly Met Ala Thr Gly Gly<br>225                     230                   235                   240 | 720 |
| acc ttc ttt gaa gag ctg ggc ttt tac tat gtt ggc ccc gtg gat ggt<br>Thr Phe Phe Glu Glu Leu Gly Phe Tyr Tyr Val Gly Pro Val Asp Gly<br>                245                   250                   255 | 768 |
| cat aat tta gat cag ctc att cca gtt tta gaa aat gtc cgc gat gcc<br>His Asn Leu Asp Gln Leu Ile Pro Val Leu Glu Asn Val Arg Asp Ala<br>                260                   265                   270 | 816 |
| aag gac ggc ccc att ttg gtg cat gtc gtc act cgc aaa ggc caa ggc<br>Lys Asp Gly Pro Ile Leu Val His Val Val Thr Arg Lys Gly Gln Gly<br>                275                   280                   285 | 864 |
| tat gct ccg gct gaa gcg gcc aag gac aaa tat cac gcc gtg cag cgc<br>Tyr Ala Pro Ala Glu Ala Ala Lys Asp Lys Tyr His Ala Val Gln Arg<br>290                     295                   300 | 912 |
| ttg gat gtg gtt tcc ggt aag cag gcg aaa gcg ccc ccg gga cct ccc<br>Leu Asp Val Val Ser Gly Lys Gln Ala Lys Ala Pro Pro Gly Pro Pro<br>305                     310                   315                   320 | 960 |
| agc tat acc tct gtt ttt tcg gaa cag ctg atc aag gaa gct aag caa<br>Ser Tyr Thr Ser Val Phe Ser Glu Gln Leu Ile Lys Glu Ala Lys Gln<br>                325                   330                   335 | 1008 |
| gac gat aag att gtg acc att acg gca gct atg ccg act ggc acc ggt<br>Asp Asp Lys Ile Val Thr Ile Thr Ala Ala Met Pro Thr Gly Thr Gly<br>                340                   345                   350 | 1056 |
| ctt gat cgt ttt cag caa tat ttt cct gaa aga atg ttt gat gtc ggt<br>Leu Asp Arg Phe Gln Gln Tyr Phe Pro Glu Arg Met Phe Asp Val Gly<br>                355                   360                   365 | 1104 |
| att gcc gaa caa cat gcc gta acc ttt gcg gct ggt ttg gcg gct gcc<br>Ile Ala Glu Gln His Ala Val Thr Phe Ala Ala Gly Leu Ala Ala Ala<br>370                     375                   380 | 1152 |
| ggt tac aag cct ttc tgt tgt ctc tat tcg acc ttc ttg cag cgc ggc<br>Gly Tyr Lys Pro Phe Cys Cys Leu Tyr Ser Thr Phe Leu Gln Arg Gly<br>385                     390                   395                   400 | 1200 |
| tat gac cag ttg gtg cat gat gtc gct atc cag aat ttg ccg gtg cgc<br>Tyr Asp Gln Leu Val His Asp Val Ala Ile Gln Asn Leu Pro Val Arg | 1248 |

```
ttc gcc gtc gat cgt gcg ggt ctt gtc ggt gcc gat ggg gca acc cat    1296
Phe Ala Val Asp Arg Ala Gly Leu Val Gly Ala Asp Gly Ala Thr His
            420                 425                 430 gcg ggt agc ttc gac ctc gcc ttt atg gtt aat ctc ccg aat atg gtc    1344
Ala Gly Ser Phe Asp Leu Ala Phe Met Val Asn Leu Pro Asn Met Val
        435                 440                 445 gtg atg gcg cct tcc gat gaa cgg gaa ttg gcc aat atg gtg cat agc    1392
Val Met Ala Pro Ser Asp Glu Arg Glu Leu Ala Asn Met Val His Ser
450                 455                 460 atg gcg cat tat gac caa ggc ccg atc tcg gtg cgt tat ccg cgt ggt    1440
Met Ala His Tyr Asp Gln Gly Pro Ile Ser Val Arg Tyr Pro Arg Gly
465                 470                 475                 480 aat ggt gtg ggt gtc tcc ttg gaa ggt gaa aag gaa att ctg cct atc    1488
Asn Gly Val Gly Val Ser Leu Glu Gly Glu Lys Glu Ile Leu Pro Ile
                485                 490                 495 ggg aaa ggt cgc ctg atc cgt cgc ggt aaa aag gtt gct atc cta tct    1536
Gly Lys Gly Arg Leu Ile Arg Arg Gly Lys Lys Val Ala Ile Leu Ser
            500                 505                 510 ctc ggc act cga ttg gaa gaa tcc ttg aag gct gct gat cgg ctt gat    1584
Leu Gly Thr Arg Leu Glu Glu Ser Leu Lys Ala Ala Asp Arg Leu Asp
        515                 520                 525 gct caa ggt ttg tcg aca tcg gtt gct gat atg cgt ttt gct aag ccc    1632
Ala Gln Gly Leu Ser Thr Ser Val Ala Asp Met Arg Phe Ala Lys Pro
530                 535                 540 ttg gat gaa gcg ctg acc cgc caa ctt ttg aaa agc cat cag gtc att    1680
Leu Asp Glu Ala Leu Thr Arg Gln Leu Leu Lys Ser His Gln Val Ile
545                 550                 555                 560 att acc att gaa gaa ggc gct ttg ggt ggt ttt gca acc caa gtc ctg    1728
Ile Thr Ile Glu Glu Gly Ala Leu Gly Gly Phe Ala Thr Gln Val Leu
                565                 570                 575 acg atg gct tcg gat gaa ggc ctg atg gat gac gga ttg aaa atc cgc    1776
Thr Met Ala Ser Asp Glu Gly Leu Met Asp Asp Gly Leu Lys Ile Arg
            580                 585                 590 acc ctg cgt ctg ccg gat cgg ttc cag ccg caa gac aag caa gaa cgg    1824
Thr Leu Arg Leu Pro Asp Arg Phe Gln Pro Gln Asp Lys Gln Glu Arg
        595                 600                 605 caa tat gcc gaa gcc ggt ctt gat gct gat ggc atc gtt gct gcg gtt    1872
Gln Tyr Ala Glu Ala Gly Leu Asp Ala Asp Gly Ile Val Ala Ala Val
610                 615                 620 atc tcc gca ttg cat cgt aat tct aaa ccc gtg gaa gtc gtc gaa atg    1920
Ile Ser Ala Leu His Arg Asn Ser Lys Pro Val Glu Val Val Glu Met
625                 630                 635                 640 gcg aat atg ggt agc atc gct cgc gct taa                            1950
Ala Asn Met Gly Ser Ile Ala Arg Ala
                645

<210> SEQ ID NO 8
<211> LENGTH: 649
<212> TYPE: PRT
<213> ORGANISM: Zymomonas mobilis

<400> SEQUENCE: 8

Met Phe Pro Asn Asp Lys Thr Pro Leu Leu Asp Lys Ile Lys Thr Pro
1               5                   10                  15

Ala Glu Leu Arg Gln Leu Asp Arg Asn Ser Leu Arg Gln Leu Ala Asp
            20                  25                  30

Glu Leu Arg Lys Glu Thr Ile Ser Ala Val Gly Val Thr Gly Gly His
        35                  40                  45
```

```
Leu Gly Ser Gly Leu Gly Val Ile Glu Leu Thr Val Ala Leu His Tyr
 50                  55                  60

Val Phe Asn Thr Pro Lys Asp Ala Leu Val Trp Asp Val Gly His Gln
 65                  70                  75                  80

Thr Tyr Pro His Lys Ile Leu Thr Gly Arg Arg Asp Arg Ile Arg Thr
                 85                  90                  95

Leu Arg Gln Arg Asp Gly Leu Ser Gly Phe Thr Gln Arg Ala Glu Ser
                100                 105                 110

Glu Tyr Asp Ala Phe Gly Ala Ala His Ser Ser Thr Ser Ile Ser Ala
            115                 120                 125

Ala Leu Gly Phe Ala Met Ala Ser Lys Leu Ser Asp Ser Asp Asp Lys
        130                 135                 140

Ala Val Ala Ile Ile Gly Asp Gly Ser Met Thr Ala Gly Met Ala Tyr
145                 150                 155                 160

Glu Ala Met Asn Asn Ala Lys Ala Ala Gly Lys Arg Leu Ile Val Ile
                165                 170                 175

Leu Asn Asp Asn Glu Met Ser Ile Ser Pro Pro Val Gly Ala Leu Ser
            180                 185                 190

Ser Tyr Leu Ser Arg Leu Ile Ser Ser Arg Pro Phe Met Asn Leu Arg
        195                 200                 205

Asp Ile Met Arg Gly Val Val Asn Arg Met Pro Lys Gly Leu Ala Thr
    210                 215                 220

Ala Ala Arg Lys Ala Asp Glu Tyr Ala Arg Gly Met Ala Thr Gly Gly
225                 230                 235                 240

Thr Phe Phe Glu Glu Leu Gly Phe Tyr Tyr Val Gly Pro Val Asp Gly
                245                 250                 255

His Asn Leu Asp Gln Leu Ile Pro Val Leu Glu Asn Val Arg Asp Ala
            260                 265                 270

Lys Asp Gly Pro Ile Leu Val His Val Val Thr Arg Lys Gly Gln Gly
        275                 280                 285

Tyr Ala Pro Ala Glu Ala Ala Lys Asp Lys Tyr His Ala Val Gln Arg
    290                 295                 300

Leu Asp Val Val Ser Gly Lys Gln Ala Lys Ala Pro Gly Pro Pro
305                 310                 315                 320

Ser Tyr Thr Ser Val Phe Ser Glu Gln Leu Ile Lys Glu Ala Lys Gln
                325                 330                 335

Asp Asp Lys Ile Val Thr Ile Thr Ala Ala Met Pro Thr Gly Thr Gly
            340                 345                 350

Leu Asp Arg Phe Gln Gln Tyr Phe Pro Glu Arg Met Phe Asp Val Gly
        355                 360                 365

Ile Ala Glu Gln His Ala Val Thr Phe Ala Ala Gly Leu Ala Ala Ala
    370                 375                 380

Gly Tyr Lys Pro Phe Cys Cys Leu Tyr Ser Thr Phe Leu Gln Arg Gly
385                 390                 395                 400

Tyr Asp Gln Leu Val His Asp Val Ala Ile Gln Asn Leu Pro Val Arg
                405                 410                 415

Phe Ala Val Asp Arg Ala Gly Leu Val Gly Ala Asp Gly Ala Thr His
            420                 425                 430

Ala Gly Ser Phe Asp Leu Ala Phe Met Val Asn Leu Pro Asn Met Val
        435                 440                 445

Val Met Ala Pro Ser Asp Glu Arg Glu Leu Ala Asn Met Val His Ser
450                 455                 460

Met Ala His Tyr Asp Gln Gly Pro Ile Ser Val Arg Tyr Pro Arg Gly
```

```
                465                 470                 475                 480
Asn Gly Val Gly Val Ser Leu Glu Gly Glu Lys Glu Ile Leu Pro Ile
                    485                 490                 495

Gly Lys Gly Arg Leu Ile Arg Arg Gly Lys Lys Val Ala Ile Leu Ser
                500                 505                 510

Leu Gly Thr Arg Leu Glu Glu Ser Leu Lys Ala Ala Asp Arg Leu Asp
            515                 520                 525

Ala Gln Gly Leu Ser Thr Ser Val Ala Asp Met Arg Phe Ala Lys Pro
        530                 535                 540

Leu Asp Glu Ala Leu Thr Arg Gln Leu Leu Lys Ser His Gln Val Ile
545                 550                 555                 560

Ile Thr Ile Glu Glu Gly Ala Leu Gly Gly Phe Ala Thr Gln Val Leu
                565                 570                 575

Thr Met Ala Ser Asp Glu Gly Leu Met Asp Asp Gly Leu Lys Ile Arg
                580                 585                 590

Thr Leu Arg Leu Pro Asp Arg Phe Gln Pro Gln Asp Lys Gln Glu Arg
            595                 600                 605

Gln Tyr Ala Glu Ala Gly Leu Asp Ala Asp Gly Ile Val Ala Ala Val
        610                 615                 620

Ile Ser Ala Leu His Arg Asn Ser Lys Pro Val Glu Val Val Glu Met
625                 630                 635                 640

Ala Asn Met Gly Ser Ile Ala Arg Ala
                645

<210> SEQ ID NO 9
<211> LENGTH: 1170
<212> TYPE: DNA
<213> ORGANISM: Zymomonas mobilis
<220> FEATURE:
<221> NAME/KEY: CDS
<222> LOCATION: (1)..(1170)

<400> SEQUENCE: 9 ttg aaa cga aaa att gct cca ata tct gtt ttt gcc gga tca gtc ttg      48
Leu Lys Arg Lys Ile Ala Pro Ile Ser Val Phe Ala Gly Ser Val Leu
1               5                   10                  15 atg atg ctg acg gcc tgt cac cat caa tcc caa gaa gcc gaa ccg gca      96
Met Met Leu Thr Ala Cys His His Gln Ser Gln Glu Ala Glu Pro Ala
            20                  25                  30 ttg caa gat gtt agt ttt gtt acc gta aaa acg cag cct ttg acc gtt     144
Leu Gln Asp Val Ser Phe Val Thr Val Lys Thr Gln Pro Leu Thr Val
        35                  40                  45 cat agc acc tta ccc ggt cgc act tcg gct tat gag gtg gcg gaa gta     192
His Ser Thr Leu Pro Gly Arg Thr Ser Ala Tyr Glu Val Ala Glu Val
    50                  55                  60 aga cct cag gta aat ggg gtc gtt ttg gcg cgc tat ttt aac gaa ggc     240
Arg Pro Gln Val Asn Gly Val Val Leu Ala Arg Tyr Phe Asn Glu Gly
65                  70                  75                  80 acg gat gtc aaa aaa ggg cag ccg cta ttc ctt atc aat ccg gct cct     288
Thr Asp Val Lys Lys Gly Gln Pro Leu Phe Leu Ile Asn Pro Ala Pro
                85                  90                  95 tat caa gcg act tat gac gtt aat aaa gcg caa tta gct cat gct gaa     336
Tyr Gln Ala Thr Tyr Asp Val Asn Lys Ala Gln Leu Ala His Ala Glu
            100                 105                 110 gcg caa gag aaa acg gct gct gct aaa tta gaa cgc tat aag gct ttg     384
Ala Gln Glu Lys Thr Ala Ala Ala Lys Leu Glu Arg Tyr Lys Ala Leu
        115                 120                 125 gct ccg gcg cag gcg att agt cgt cag gat tat gat gat gct ttg gcc     432
```

| | | | | | | | | | | | | |
|---|---|---|---|---|---|---|---|---|---|---|---|---|
| Ala | Pro | Ala | Gln | Ala | Ile | Ser | Arg | Gln | Asp | Tyr | Asp | Asp | Ala | Leu | Ala |
| | 130 | | | | 135 | | | | 140 | | | | |

| acc | gat | cgc | gcg | gcc | aag | gca | gat | att | gcc | caa | gcc | aaa | gcg | aat | att | 480 |
|---|---|---|---|---|---|---|---|---|---|---|---|---|---|---|---|---|
| Thr | Asp | Arg | Ala | Ala | Lys | Ala | Asp | Ile | Ala | Gln | Ala | Lys | Ala | Asn | Ile | |
| 145 | | | | | 150 | | | | | 155 | | | | | 160 | |

| gaa | tta | tcg | gct | gtt | aat | ttg | gga | tac | acc | cgt | gtg | acc | gcg | cct | att | 528 |
|---|---|---|---|---|---|---|---|---|---|---|---|---|---|---|---|---|
| Glu | Leu | Ser | Ala | Val | Asn | Leu | Gly | Tyr | Thr | Arg | Val | Thr | Ala | Pro | Ile | |
| | | | | 165 | | | | | 170 | | | | | 175 | | |

| act | ggc | cgg | atc | ggg | cgc | gtt | ttg | aca | acg | gtc | ggt | gcc | ttg | gta | acg | 576 |
|---|---|---|---|---|---|---|---|---|---|---|---|---|---|---|---|---|
| Thr | Gly | Arg | Ile | Gly | Arg | Val | Leu | Thr | Thr | Val | Gly | Ala | Leu | Val | Thr | |
| | | 180 | | | | | 185 | | | | | 190 | | | | |

| tcg | ggg | caa | agt | tcg | aat | atg | gcg | att | gtg | acc | cgc | ctt | gac | ccg | att | 624 |
|---|---|---|---|---|---|---|---|---|---|---|---|---|---|---|---|---|
| Ser | Gly | Gln | Ser | Ser | Asn | Met | Ala | Ile | Val | Thr | Arg | Leu | Asp | Pro | Ile | |
| | | | 195 | | | | | 200 | | | | | 205 | | | |

| tat | gtc | gat | gtg | aat | ttg | cca | aca | gtc | gat | ttt | tta | cgg | ttg | cgg | cgc | 672 |
|---|---|---|---|---|---|---|---|---|---|---|---|---|---|---|---|---|
| Tyr | Val | Asp | Val | Asn | Leu | Pro | Thr | Val | Asp | Phe | Leu | Arg | Leu | Arg | Arg | |
| 210 | | | | | 215 | | | | | 220 | | | | | | |

| gag | tta | aaa | gcg | gga | act | ttg | aaa | cgg | aac | ggc | aat | gat | gcc | gaa | gtc | 720 |
|---|---|---|---|---|---|---|---|---|---|---|---|---|---|---|---|---|
| Glu | Leu | Lys | Ala | Gly | Thr | Leu | Lys | Arg | Asn | Gly | Asn | Asp | Ala | Glu | Val | |
| 225 | | | | | 230 | | | | | 235 | | | | | 240 | |

| tcc | ctt | att | ctc | gat | gat | aat | tcg | acc | tat | aat | caa | aaa | gga | cgg | ctg | 768 |
|---|---|---|---|---|---|---|---|---|---|---|---|---|---|---|---|---|
| Ser | Leu | Ile | Leu | Asp | Asp | Asn | Ser | Thr | Tyr | Asn | Gln | Lys | Gly | Arg | Leu | |
| | | | | 245 | | | | | 250 | | | | | 255 | | |

| gct | tta | agc | gaa | gtc | agt | gcc | gac | acc | cag | aca | tcg | acc | att | gtt | gtt | 816 |
|---|---|---|---|---|---|---|---|---|---|---|---|---|---|---|---|---|
| Ala | Leu | Ser | Glu | Val | Ser | Ala | Asp | Thr | Gln | Thr | Ser | Thr | Ile | Val | Val | |
| | | | | 260 | | | | | 265 | | | | | 270 | | |

| cgt | gcg | gtt | ttc | cca | aat | cct | gaa | cat | ttg | ttg | ctg | ccc | gga | atg | ttt | 864 |
|---|---|---|---|---|---|---|---|---|---|---|---|---|---|---|---|---|
| Arg | Ala | Val | Phe | Pro | Asn | Pro | Glu | His | Leu | Leu | Leu | Pro | Gly | Met | Phe | |
| | | 275 | | | | | 280 | | | | | 285 | | | | |

| gtt | tat | ggt | cgg | ata | gaa | gag | ggc | gtt | gat | ccg | aac | gcc | ttg | ttg | gtt | 912 |
|---|---|---|---|---|---|---|---|---|---|---|---|---|---|---|---|---|
| Val | Tyr | Gly | Arg | Ile | Glu | Glu | Gly | Val | Asp | Pro | Asn | Ala | Leu | Leu | Val | |
| | 290 | | | | | 295 | | | | | 300 | | | | | |

| ccg | caa | gaa | tcc | gtt | ttc | cga | aat | aac | cac | ggt | gat | ccg | atg | tta | tat | 960 |
|---|---|---|---|---|---|---|---|---|---|---|---|---|---|---|---|---|
| Pro | Gln | Glu | Ser | Val | Phe | Arg | Asn | Asn | His | Gly | Asp | Pro | Met | Leu | Tyr | |
| 305 | | | | | 310 | | | | | 315 | | | | | 320 | |

| gtc | gtc | aat | aaa | gac | gac | gtt | att | gaa | gca | cgc | ccg | ata | aaa | acc | ggt | 1008 |
|---|---|---|---|---|---|---|---|---|---|---|---|---|---|---|---|---|
| Val | Val | Asn | Lys | Asp | Asp | Val | Ile | Glu | Ala | Arg | Pro | Ile | Lys | Thr | Gly | |
| | | | | 325 | | | | | 330 | | | | | 335 | | |

| gaa | gct | atc | gga | acg | caa | tgg | gct | gtg | aca | tcc | ggt | ttg | caa | aaa | ggc | 1056 |
|---|---|---|---|---|---|---|---|---|---|---|---|---|---|---|---|---|
| Glu | Ala | Ile | Gly | Thr | Gln | Trp | Ala | Val | Thr | Ser | Gly | Leu | Gln | Lys | Gly | |
| | | | | 340 | | | | | 345 | | | | | 350 | | |

| gaa | cgc | gtt | ttg | gtc | tct | ggt | ctt | caa | aaa | gtg | aat | atc | ggc | gac | aaa | 1104 |
|---|---|---|---|---|---|---|---|---|---|---|---|---|---|---|---|---|
| Glu | Arg | Val | Leu | Val | Ser | Gly | Leu | Gln | Lys | Val | Asn | Ile | Gly | Asp | Lys | |
| | | 355 | | | | | 360 | | | | | 365 | | | | |

| gtt | cat | ccg | aca | gag | gct | tct | ctt | acc | aaa | gat | gcc | tcg | cca | gaa | aag | 1152 |
|---|---|---|---|---|---|---|---|---|---|---|---|---|---|---|---|---|
| Val | His | Pro | Thr | Glu | Ala | Ser | Leu | Thr | Lys | Asp | Ala | Ser | Pro | Glu | Lys | |
| | 370 | | | | | 375 | | | | | 380 | | | | | |

| aag | ggc | ggc | aag | gcg | taa | 1170 |
|---|---|---|---|---|---|---|
| Lys | Gly | Gly | Lys | Ala | | |
| 385 | | | | | | |

<210> SEQ ID NO 10
<211> LENGTH: 389
<212> TYPE: PRT
<213> ORGANISM: Zymomonas mobilis

<400> SEQUENCE: 10

| Leu | Lys | Arg | Lys | Ile | Ala | Pro | Ile | Ser | Val | Phe | Ala | Gly | Ser | Val | Leu |
|---|---|---|---|---|---|---|---|---|---|---|---|---|---|---|---|
| 1 | | | | 5 | | | | | 10 | | | | | 15 | |

| Met | Met | Leu | Thr | Ala | Cys | His | His | Gln | Ser | Gln | Glu | Ala | Glu | Pro | Ala |
|---|---|---|---|---|---|---|---|---|---|---|---|---|---|---|---|

```
                20                  25                  30
Leu Gln Asp Val Ser Phe Val Thr Val Lys Thr Gln Pro Leu Thr Val
                35                  40                  45

His Ser Thr Leu Pro Gly Arg Thr Ser Ala Tyr Glu Val Ala Glu Val
 50                  55                  60

Arg Pro Gln Val Asn Gly Val Leu Ala Arg Tyr Phe Asn Glu Gly
 65                  70                  75                  80

Thr Asp Val Lys Lys Gly Gln Pro Leu Phe Leu Ile Asn Pro Ala Pro
                85                  90                  95

Tyr Gln Ala Thr Tyr Asp Val Asn Lys Ala Gln Leu Ala His Ala Glu
                100                 105                 110

Ala Gln Glu Lys Thr Ala Ala Lys Leu Glu Arg Tyr Lys Ala Leu
                115                 120                 125

Ala Pro Ala Gln Ala Ile Ser Arg Gln Asp Tyr Asp Asp Ala Leu Ala
                130                 135                 140

Thr Asp Arg Ala Ala Lys Ala Asp Ile Ala Gln Ala Lys Ala Asn Ile
145                 150                 155                 160

Glu Leu Ser Ala Val Asn Leu Gly Tyr Thr Arg Val Thr Ala Pro Ile
                165                 170                 175

Thr Gly Arg Ile Gly Arg Val Leu Thr Thr Val Gly Ala Leu Val Thr
                180                 185                 190

Ser Gly Gln Ser Ser Asn Met Ala Ile Val Thr Arg Leu Asp Pro Ile
                195                 200                 205

Tyr Val Asp Val Asn Leu Pro Thr Val Asp Phe Leu Arg Leu Arg Arg
                210                 215                 220

Glu Leu Lys Ala Gly Thr Leu Lys Arg Asn Gly Asn Asp Ala Glu Val
225                 230                 235                 240

Ser Leu Ile Leu Asp Asp Asn Ser Thr Tyr Asn Gln Lys Gly Arg Leu
                245                 250                 255

Ala Leu Ser Glu Val Ser Ala Asp Thr Gln Thr Ser Thr Ile Val Val
                260                 265                 270

Arg Ala Val Phe Pro Asn Pro Glu His Leu Leu Pro Gly Met Phe
                275                 280                 285

Val Tyr Gly Arg Ile Glu Glu Gly Val Asp Pro Asn Ala Leu Leu Val
                290                 295                 300

Pro Gln Glu Ser Val Phe Arg Asn Asn His Gly Asp Pro Met Leu Tyr
305                 310                 315                 320

Val Val Asn Lys Asp Asp Val Ile Glu Ala Arg Pro Ile Lys Thr Gly
                325                 330                 335

Glu Ala Ile Gly Thr Gln Trp Ala Val Thr Ser Gly Leu Gln Lys Gly
                340                 345                 350

Glu Arg Val Leu Val Ser Gly Leu Gln Lys Val Asn Ile Gly Asp Lys
                355                 360                 365

Val His Pro Thr Glu Ala Ser Leu Thr Lys Asp Ala Ser Pro Glu Lys
                370                 375                 380

Lys Gly Gly Lys Ala
385

<210> SEQ ID NO 11
<211> LENGTH: 3144
<212> TYPE: DNA
<213> ORGANISM: Zymomonas mobilis
<220> FEATURE:
<221> NAME/KEY: CDS
<222> LOCATION: (1)..(3144)
```

<400> SEQUENCE: 11

```
atg gct cgc tat ttt att gac cgc cct gtt ttt gct tgg gtt atc ggt    48
Met Ala Arg Tyr Phe Ile Asp Arg Pro Val Phe Ala Trp Val Ile Gly
1               5                   10                  15 ctt atc atc atg tta ttg ggt gcc ttg gca att gtt aaa atg cct att    96
Leu Ile Ile Met Leu Leu Gly Ala Leu Ala Ile Val Lys Met Pro Ile
                20                  25                  30 gcc caa tat ccg aat gtt gcc cct ccg cag att gag atc agt gtg tct   144
Ala Gln Tyr Pro Asn Val Ala Pro Pro Gln Ile Glu Ile Ser Val Ser
            35                  40                  45 tat ccg ggg gcg tcg gct gaa acg atc aat aat acc gtt gtt cgg cct   192
Tyr Pro Gly Ala Ser Ala Glu Thr Ile Asn Asn Thr Val Val Arg Pro
    50                  55                  60 atc tta cag cag atg cat ggc atc gat aat ctg gaa tat att tcg gct   240
Ile Leu Gln Gln Met His Gly Ile Asp Asn Leu Glu Tyr Ile Ser Ala
65                  70                  75                  80 tct tcc ttt gca tca ggt cag atg acg att gat ttg acc ttt gca caa   288
Ser Ser Phe Ala Ser Gly Gln Met Thr Ile Asp Leu Thr Phe Ala Gln
                85                  90                  95 ggt acc gat gcc gat atc gca cag gtg caa gtc cag aat aaa tta caa   336
Gly Thr Asp Ala Asp Ile Ala Gln Val Gln Val Gln Asn Lys Leu Gln
            100                 105                 110 tta gcg cag cct cgt ttg ccg tcg gat gtg gtc aat cag ggt att acg   384
Leu Ala Gln Pro Arg Leu Pro Ser Asp Val Val Asn Gln Gly Ile Thr
        115                 120                 125 gtt aac cgt tct gcc aaa agt ttt atg atg att atg tcc ttc atc tcg   432
Val Asn Arg Ser Ala Lys Ser Phe Met Met Ile Met Ser Phe Ile Ser
    130                 135                 140 acc gat ggc agt atg tcc tat cag gac atc aac gat tat gtg gca tcg   480
Thr Asp Gly Ser Met Ser Tyr Gln Asp Ile Asn Asp Tyr Val Ala Ser
145                 150                 155                 160 aat att gct gat ccg ttg agc cgt gtt tcc ggt gtc ggc gat tac act   528
Asn Ile Ala Asp Pro Leu Ser Arg Val Ser Gly Val Gly Asp Tyr Thr
                165                 170                 175 ctg ttc ggt ttt gaa tat gca atg cgg gtc tgg tta gat cca gca aag   576
Leu Phe Gly Phe Glu Tyr Ala Met Arg Val Trp Leu Asp Pro Ala Lys
            180                 185                 190 ctc tac aaa tat aat ttg act gta gcg gat gtc caa tca gct att tct   624
Leu Tyr Lys Tyr Asn Leu Thr Val Ala Asp Val Gln Ser Ala Ile Ser
        195                 200                 205 acc cag aat att cag ctt tca tcc ggt gaa ttg ggc gga ttg cct gcg   672
Thr Gln Asn Ile Gln Leu Ser Ser Gly Glu Leu Gly Gly Leu Pro Ala
    210                 215                 220 gtt cag ggt att cgt ttg gat gcg acc att att ggc ccg acc cgt ttg   720
Val Gln Gly Ile Arg Leu Asp Ala Thr Ile Ile Gly Pro Thr Arg Leu
225                 230                 235                 240 acc tcg cct gaa gaa ttt aaa aat att ctg gtc aag gct ttg ccg gat   768
Thr Ser Pro Glu Glu Phe Lys Asn Ile Leu Val Lys Ala Leu Pro Asp
                245                 250                 255 ggc gcc caa atc aaa ttg ggt gac atc gct aaa gta gag ttg ggc gcg   816
Gly Ala Gln Ile Lys Leu Gly Asp Ile Ala Lys Val Glu Leu Gly Ala
            260                 265                 270 caa agc tat aac ttt gac gtg cgc tat aat aac cag ccg gct tcg ggt   864
Gln Ser Tyr Asn Phe Asp Val Arg Tyr Asn Asn Gln Pro Ala Ser Gly
        275                 280                 285 att gcg atc aaa ttg gca ccg ggg gcg aac cag ctt caa act gaa aag   912
Ile Ala Ile Lys Leu Ala Pro Gly Ala Asn Gln Leu Gln Thr Glu Lys
    290                 295                 300
```

```
ttg atc cgt cag cgt ttg gcc gat ttg gaa cct ttc ttc cct cat ggt    960
Leu Ile Arg Gln Arg Leu Ala Asp Leu Glu Pro Phe Phe Pro His Gly
305             310                 315                 320 ttg aag gtc gaa tat ccg gtt gat acc aag cca ttt gtg acg gct tct   1008
Leu Lys Val Glu Tyr Pro Val Asp Thr Lys Pro Phe Val Thr Ala Ser
                325                 330                 335 atc cat gag gtt att gaa acc ttg gtg gaa gct att gcg ctt gtt ttc   1056
Ile His Glu Val Ile Glu Thr Leu Val Glu Ala Ile Ala Leu Val Phe
            340                 345                 350 ttg gtg atg ctg atc ttc ttg cag aat ttc cgt gct acc ttg atc ccg   1104
Leu Val Met Leu Ile Phe Leu Gln Asn Phe Arg Ala Thr Leu Ile Pro
        355                 360                 365 acg att gct gtg cca gtg gtg ttg tta ggc acc ttt ggt gtg ctt tct   1152
Thr Ile Ala Val Pro Val Val Leu Leu Gly Thr Phe Gly Val Leu Ser
    370                 375                 380 gtt ctt ggt ttt tca atc aat act ctg acg atg ttg gca atg gtc ttg   1200
Val Leu Gly Phe Ser Ile Asn Thr Leu Thr Met Leu Ala Met Val Leu
385                 390                 395                 400 gct gtt ggc ttg ttg gtc gat gat gcc atc gtc gtt gtt gaa aat gtc   1248
Ala Val Gly Leu Leu Val Asp Asp Ala Ile Val Val Val Glu Asn Val
                405                 410                 415 gaa cgt ttg atg cga gat gaa aag ctg ccc ccg aaa gag gcg gcg aag   1296
Glu Arg Leu Met Arg Asp Glu Lys Leu Pro Pro Lys Glu Ala Ala Lys
                420                 425                 430 cgc tcg atg gat gaa att tct ggt gct ttg atc ggt atc gtc ttg gtc   1344
Arg Ser Met Asp Glu Ile Ser Gly Ala Leu Ile Gly Ile Val Leu Val
            435                 440                 445 ttg tcg gcc gtg ttc ttg cct atg gcg gcc ttt tca ggg tca acg ggc   1392
Leu Ser Ala Val Phe Leu Pro Met Ala Ala Phe Ser Gly Ser Thr Gly
        450                 455                 460 gtt atc tat cgc caa ttc tcg att acg att gtg gtg gcg atg ggg ctg   1440
Val Ile Tyr Arg Gln Phe Ser Ile Thr Ile Val Val Ala Met Gly Leu
465                 470                 475                 480 tct gtc ctt gtg gcg atg att atg acg cca gcc ctt tgc gca acg atg   1488
Ser Val Leu Val Ala Met Ile Met Thr Pro Ala Leu Cys Ala Thr Met
                485                 490                 495 tta aag ccg att gac cat gac caa gcc gat aaa aag ccg ggt atc ttt   1536
Leu Lys Pro Ile Asp His Asp Gln Ala Asp Lys Lys Pro Gly Ile Phe
                500                 505                 510 ggt cgc ttg gcg aat ggc ttt aac cgt gct ttt gac cga ttg aat aat   1584
Gly Arg Leu Ala Asn Gly Phe Asn Arg Ala Phe Asp Arg Leu Asn Asn
            515                 520                 525 ggt tat ttg ggt ggt gtg tct tgg ttg tta gga cgt tcc gtc aaa ggc   1632
Gly Tyr Leu Gly Gly Val Ser Trp Leu Leu Gly Arg Ser Val Lys Gly
        530                 535                 540 ggc att gcc ttt ttg atc att gtt ttc gcc gtt ggt tat tta ttc act   1680
Gly Ile Ala Phe Leu Ile Ile Val Phe Ala Val Gly Tyr Leu Phe Thr
545                 550                 555                 560 cgc ttg cca acc gga ttt ttg ccg gat gaa gat cag ggt gaa ttt att   1728
Arg Leu Pro Thr Gly Phe Leu Pro Asp Glu Asp Gln Gly Glu Phe Ile
                565                 570                 575 ggt cag gtg acc tta ccg ccg ggg gcg acc caa gaa caa acg tcg gaa   1776
Gly Gln Val Thr Leu Pro Pro Gly Ala Thr Gln Glu Gln Thr Ser Glu
                580                 585                 590 gcg gtg cgc aag gtt aat gat tat ctt ctg tcc gca gag aaa gac agt   1824
Ala Val Arg Lys Val Asn Asp Tyr Leu Leu Ser Ala Glu Lys Asp Ser
            595                 600                 605 gtc ata tct gtg atg acg gtt agc ggt ttt aac ttt ggt ggt cag gga   1872
Val Ile Ser Val Met Thr Val Ser Gly Phe Asn Phe Gly Gly Gln Gly
        610                 615                 620
```

-continued

```
caa aat gcc ggt tct ttc ttc gtt cgt ttg aaa cct tgg gat cag cgt      1920
Gln Asn Ala Gly Ser Phe Phe Val Arg Leu Lys Pro Trp Asp Gln Arg
625             630                 635                 640 ccg aaa gcc tcg caa agt gct tcg gcc ttg gca atg cgg acg atg atg      1968
Pro Lys Ala Ser Gln Ser Ala Ser Ala Leu Ala Met Arg Thr Met Met
            645                 650                 655 cat ttt tgg ggt gat ccg tca tcg atg act ttt gcc ttt aat atg cct      2016
His Phe Trp Gly Asp Pro Ser Ser Met Thr Phe Ala Phe Asn Met Pro
        660                 665                 670 gct gtc cgc gac ttg ggt aat gcc acc ggt ttt gac ttg gaa ctg gaa      2064
Ala Val Arg Asp Leu Gly Asn Ala Thr Gly Phe Asp Leu Glu Leu Glu
    675                 680                 685 gat cgc ggt cat atc ggt cat gca aaa ttc ctt gaa gcc cgt aac atg      2112
Asp Arg Gly His Ile Gly His Ala Lys Phe Leu Glu Ala Arg Asn Met
690                 695                 700 tta ttg gct ttg gcc tcg aaa gat ccc cgc tta agt ggt gtc cgt ccg      2160
Leu Leu Ala Leu Ala Ser Lys Asp Pro Arg Leu Ser Gly Val Arg Pro
705                 710                 715                 720 aat ggt atg gaa gat gcc cct caa tat cat ttg acc gtt gat tac ggc      2208
Asn Gly Met Glu Asp Ala Pro Gln Tyr His Leu Thr Val Asp Tyr Gly
                725                 730                 735 aaa gct gtt atg atg gga ttg acc cca aat gat gtg aat gtg gcc ttg      2256
Lys Ala Val Met Met Gly Leu Thr Pro Asn Asp Val Asn Val Ala Leu
            740                 745                 750 cag ggg tct ttg ggg tcg att tac gtc aat cag ttt atg cgg gat gac      2304
Gln Gly Ser Leu Gly Ser Ile Tyr Val Asn Gln Phe Met Arg Asp Asp
        755                 760                 765 cgt gtg aag cag gtc tat tta atg ggg gca ccg gaa gcg cgt atg ctg      2352
Arg Val Lys Gln Val Tyr Leu Met Gly Ala Pro Glu Ala Arg Met Leu
    770                 775                 780 cct tcc gat ttt tcc aaa tgg tat ctg cgg aat aat gtc ggc acg atg      2400
Pro Ser Asp Phe Ser Lys Trp Tyr Leu Arg Asn Asn Val Gly Thr Met
785                 790                 795                 800 gtt ccc ttt agc gcc ttt atg aca gga aca tgg caa acg ggc cct cag      2448
Val Pro Phe Ser Ala Phe Met Thr Gly Thr Trp Gln Thr Gly Pro Gln
                805                 810                 815 aaa gtc gaa aat tat aac ggc tat aat tct ttc gaa att atg ggc gcg      2496
Lys Val Glu Asn Tyr Asn Gly Tyr Asn Ser Phe Glu Ile Met Gly Ala
            820                 825                 830 cct gca ccg gga cat agt tcg ggt gaa gcc att cag gcg atg acc gag      2544
Pro Ala Pro Gly His Ser Ser Gly Glu Ala Ile Gln Ala Met Thr Glu
        835                 840                 845 atc gtt cat aaa ttg cca gct ggt gtt ggg cat gaa tgg aca ggg tta      2592
Ile Val His Lys Leu Pro Ala Gly Val Gly His Glu Trp Thr Gly Leu
    850                 855                 860 tct ttt gaa gag cag gcg gcc ggt tcg tcc acc atg tct ctt tat gcg      2640
Ser Phe Glu Glu Gln Ala Ala Gly Ser Ser Thr Met Ser Leu Tyr Ala
865                 870                 875                 880 att tcc gcg att gtg gtt ctg ttc tgt ctt gcc gca ctt tat gaa agc      2688
Ile Ser Ala Ile Val Val Leu Phe Cys Leu Ala Ala Leu Tyr Glu Ser
                885                 890                 895 tgg gcc gtg ccg tta tcg gtt att ttg gtt ctg cct ttg ggt gtc ttg      2736
Trp Ala Val Pro Leu Ser Val Ile Leu Val Leu Pro Leu Gly Val Leu
            900                 905                 910 ggt gcc gtt gta gca acc ttg atg cgt gga ttg tcg aat gac gtc tat      2784
Gly Ala Val Val Ala Thr Leu Met Arg Gly Leu Ser Asn Asp Val Tyr
        915                 920                 925 ttc cag atc ggt ttg ctg acg acc gtt ggt ttg acc gtt aaa aac gct      2832
Phe Gln Ile Gly Leu Leu Thr Thr Val Gly Leu Thr Val Lys Asn Ala
```

```
                    930                935                940
att ttg att gtc gaa ttt gca aaa gcc ttt ttc gat aat ggc gtg cca      2880
Ile Leu Ile Val Glu Phe Ala Lys Ala Phe Phe Asp Asn Gly Val Pro
945                 950                 955                960 ctt ttg caa tcg gtg gtt caa gca ggc cgt gag cgg tta cgg cct att      2928
Leu Leu Gln Ser Val Val Gln Ala Gly Arg Glu Arg Leu Arg Pro Ile
                965                 970                 975 ttg atg acc tct att gct ttt gtg ttg ggg gtt att cca ttg agc atc      2976
Leu Met Thr Ser Ile Ala Phe Val Leu Gly Val Ile Pro Leu Ser Ile
            980                 985                 990 gca aca ggg gct tct tcg gca gca cgt atc gct atc gga acg gcc gtt      3024
Ala Thr Gly Ala Ser Ser Ala Ala Arg Ile Ala Ile Gly Thr Ala Val
        995                 1000                1005 gtc ggc ggg atg gtg acg gct acc ttg ttg acg att ttc ttt gtg          3069
Val Gly Gly Met Val Thr Ala Thr Leu Leu Thr Ile Phe Phe Val
    1010                1015                1020 cct ctt ttc ttt gtg gtg gtt ttg aag ctg ttt cgg gtg aaa ccg          3114
Pro Leu Phe Phe Val Val Val Leu Lys Leu Phe Arg Val Lys Pro
1025                1030                1035 aac aag ctg aat gcg gag gaa gca gcc tga                              3144
Asn Lys Leu Asn Ala Glu Glu Ala Ala
1040                1045

<210> SEQ ID NO 12
<211> LENGTH: 1047
<212> TYPE: PRT
<213> ORGANISM: Zymomonas mobilis

<400> SEQUENCE: 12

Met Ala Arg Tyr Phe Ile Asp Arg Pro Val Phe Ala Trp Val Ile Gly
1               5                   10                  15

Leu Ile Ile Met Leu Leu Gly Ala Leu Ala Ile Val Lys Met Pro Ile
            20                  25                  30

Ala Gln Tyr Pro Asn Val Ala Pro Pro Gln Ile Glu Ile Ser Val Ser
        35                  40                  45

Tyr Pro Gly Ala Ser Ala Glu Thr Ile Asn Asn Thr Val Val Arg Pro
    50                  55                  60

Ile Leu Gln Gln Met His Gly Ile Asp Asn Leu Glu Tyr Ile Ser Ala
65                  70                  75                  80

Ser Ser Phe Ala Ser Gly Gln Met Thr Ile Asp Leu Thr Phe Ala Gln
                85                  90                  95

Gly Thr Asp Ala Asp Ile Ala Gln Val Gln Val Gln Asn Lys Leu Gln
            100                 105                 110

Leu Ala Gln Pro Arg Leu Pro Ser Asp Val Val Asn Gln Gly Ile Thr
        115                 120                 125

Val Asn Arg Ser Ala Lys Ser Phe Met Met Ile Met Ser Phe Ile Ser
    130                 135                 140

Thr Asp Gly Ser Met Ser Tyr Gln Asp Ile Asn Asp Tyr Val Ala Ser
145                 150                 155                 160

Asn Ile Ala Asp Pro Leu Ser Arg Val Ser Gly Val Gly Asp Tyr Thr
                165                 170                 175

Leu Phe Gly Phe Glu Tyr Ala Met Arg Val Trp Leu Asp Pro Ala Lys
            180                 185                 190

Leu Tyr Lys Tyr Asn Leu Thr Val Ala Asp Val Gln Ser Ala Ile Ser
        195                 200                 205

Thr Gln Asn Ile Gln Leu Ser Ser Gly Glu Leu Gly Gly Leu Pro Ala
    210                 215                 220
```

```
Val Gln Gly Ile Arg Leu Asp Ala Thr Ile Ile Gly Pro Thr Arg Leu
225                 230                 235                 240

Thr Ser Pro Glu Glu Phe Lys Asn Ile Leu Val Lys Ala Leu Pro Asp
                245                 250                 255

Gly Ala Gln Ile Lys Leu Gly Asp Ile Ala Lys Val Glu Leu Gly Ala
            260                 265                 270

Gln Ser Tyr Asn Phe Asp Val Arg Tyr Asn Asn Gln Pro Ala Ser Gly
        275                 280                 285

Ile Ala Ile Lys Leu Ala Pro Gly Ala Asn Gln Leu Gln Thr Glu Lys
    290                 295                 300

Leu Ile Arg Gln Arg Leu Ala Asp Leu Glu Pro Phe Phe Pro His Gly
305                 310                 315                 320

Leu Lys Val Glu Tyr Pro Val Asp Thr Lys Pro Phe Val Thr Ala Ser
                325                 330                 335

Ile His Glu Val Ile Glu Thr Leu Val Glu Ala Ile Ala Leu Val Phe
            340                 345                 350

Leu Val Met Leu Ile Phe Leu Gln Asn Phe Arg Ala Thr Leu Ile Pro
        355                 360                 365

Thr Ile Ala Val Pro Val Val Leu Leu Gly Thr Phe Gly Val Leu Ser
    370                 375                 380

Val Leu Gly Phe Ser Ile Asn Thr Leu Thr Met Leu Ala Met Val Leu
385                 390                 395                 400

Ala Val Gly Leu Leu Val Asp Asp Ala Ile Val Val Glu Asn Val
                405                 410                 415

Glu Arg Leu Met Arg Asp Glu Lys Leu Pro Pro Lys Glu Ala Ala Lys
            420                 425                 430

Arg Ser Met Asp Glu Ile Ser Gly Ala Leu Ile Gly Ile Val Leu Val
        435                 440                 445

Leu Ser Ala Val Phe Leu Pro Met Ala Ala Phe Ser Gly Ser Thr Gly
    450                 455                 460

Val Ile Tyr Arg Gln Phe Ser Ile Thr Ile Val Val Ala Met Gly Leu
465                 470                 475                 480

Ser Val Leu Val Ala Met Ile Met Thr Pro Ala Leu Cys Ala Thr Met
                485                 490                 495

Leu Lys Pro Ile Asp His Asp Gln Ala Asp Lys Lys Pro Gly Ile Phe
            500                 505                 510

Gly Arg Leu Ala Asn Gly Phe Asn Arg Ala Phe Asp Arg Leu Asn Asn
        515                 520                 525

Gly Tyr Leu Gly Gly Val Ser Trp Leu Leu Gly Arg Ser Val Lys Gly
    530                 535                 540

Gly Ile Ala Phe Leu Ile Ile Val Phe Ala Val Gly Tyr Leu Phe Thr
545                 550                 555                 560

Arg Leu Pro Thr Gly Phe Leu Pro Asp Glu Asp Gln Gly Glu Phe Ile
                565                 570                 575

Gly Gln Val Thr Leu Pro Pro Gly Ala Thr Gln Glu Gln Thr Ser Glu
            580                 585                 590

Ala Val Arg Lys Val Asn Asp Tyr Leu Leu Ser Ala Glu Lys Asp Ser
        595                 600                 605

Val Ile Ser Val Met Thr Val Ser Gly Phe Asn Phe Gly Gly Gln Gly
    610                 615                 620

Gln Asn Ala Gly Ser Phe Phe Val Arg Leu Lys Pro Trp Asp Gln Arg
625                 630                 635                 640
```

```
Pro Lys Ala Ser Gln Ser Ala Ser Ala Leu Ala Met Arg Thr Met Met
            645                 650                 655

His Phe Trp Gly Asp Pro Ser Ser Met Thr Phe Ala Phe Asn Met Pro
        660                 665                 670

Ala Val Arg Asp Leu Gly Asn Ala Thr Gly Phe Asp Leu Glu Leu Glu
    675                 680                 685

Asp Arg Gly His Ile Gly His Ala Lys Phe Leu Glu Ala Arg Asn Met
690                 695                 700

Leu Leu Ala Leu Ala Ser Lys Asp Pro Arg Leu Ser Gly Val Arg Pro
705                 710                 715                 720

Asn Gly Met Glu Asp Ala Pro Gln Tyr His Leu Thr Val Asp Tyr Gly
            725                 730                 735

Lys Ala Val Met Met Gly Leu Thr Pro Asn Asp Val Asn Val Ala Leu
        740                 745                 750

Gln Gly Ser Leu Gly Ser Ile Tyr Val Asn Gln Phe Met Arg Asp Asp
    755                 760                 765

Arg Val Lys Gln Val Tyr Leu Met Gly Ala Pro Glu Ala Arg Met Leu
770                 775                 780

Pro Ser Asp Phe Ser Lys Trp Tyr Leu Arg Asn Asn Val Gly Thr Met
785                 790                 795                 800

Val Pro Phe Ser Ala Phe Met Thr Gly Thr Trp Gln Thr Gly Pro Gln
            805                 810                 815

Lys Val Glu Asn Tyr Asn Gly Tyr Asn Ser Phe Glu Ile Met Gly Ala
        820                 825                 830

Pro Ala Pro Gly His Ser Ser Gly Glu Ala Ile Gln Ala Met Thr Glu
    835                 840                 845

Ile Val His Lys Leu Pro Ala Gly Val Gly His Glu Trp Thr Gly Leu
850                 855                 860

Ser Phe Glu Glu Gln Ala Ala Gly Ser Ser Thr Met Ser Leu Tyr Ala
865                 870                 875                 880

Ile Ser Ala Ile Val Val Leu Phe Cys Leu Ala Ala Leu Tyr Glu Ser
            885                 890                 895

Trp Ala Val Pro Leu Ser Val Ile Leu Val Leu Pro Leu Gly Val Leu
        900                 905                 910

Gly Ala Val Val Ala Thr Leu Met Arg Gly Leu Ser Asn Asp Val Tyr
    915                 920                 925

Phe Gln Ile Gly Leu Leu Thr Thr Val Gly Leu Thr Val Lys Asn Ala
930                 935                 940

Ile Leu Ile Val Glu Phe Ala Lys Ala Phe Phe Asp Asn Gly Val Pro
945                 950                 955                 960

Leu Leu Gln Ser Val Val Gln Ala Gly Arg Glu Arg Leu Arg Pro Ile
            965                 970                 975

Leu Met Thr Ser Ile Ala Phe Val Leu Gly Val Ile Pro Leu Ser Ile
        980                 985                 990

Ala Thr Gly Ala Ser Ser Ala Ala  Arg Ile Ala Ile Gly  Thr Ala Val
    995                 1000                1005

Val Gly  Gly Met Val Thr Ala  Thr Leu Leu Thr Ile  Phe Phe Val
    1010                1015                1020

Pro Leu  Phe Phe Val Val Val  Leu Lys Leu Phe Arg  Val Lys Pro
    1025                1030                1035

Asn Lys  Leu Asn Ala Glu Glu  Ala Ala
    1040                1045
```

<210> SEQ ID NO 13
<211> LENGTH: 1539
<212> TYPE: DNA
<213> ORGANISM: Zymomonas mobilis
<220> FEATURE:
<221> NAME/KEY: CDS
<222> LOCATION: (1)..(1539)

<400> SEQUENCE: 13

| | | | | | | | | | | | | | | | | |
|---|---|---|---|---|---|---|---|---|---|---|---|---|---|---|---|---|
| atg | act | tta | ttt | tcg | gct | tct | tcg | gct | ctg | att | aag | cgg | agt | aaa | aaa | 48 |
| Met | Thr | Leu | Phe | Ser | Ala | Ser | Ser | Ala | Leu | Ile | Lys | Arg | Ser | Lys | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gga | tgg | cgt | tat | cct | gta | acg | cta | ttc | tta | tcg | act | aat | att | ctg | ttg | 96 |
| Gly | Trp | Arg | Tyr | Pro | Val | Thr | Leu | Phe | Leu | Ser | Thr | Asn | Ile | Leu | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| gct | gga | tgc | acg | atg | gca | ccg | aaa | tat | cat | cgt | cca | gca | gcg | tct | gtg | 144 |
| Ala | Gly | Cys | Thr | Met | Ala | Pro | Lys | Tyr | His | Arg | Pro | Ala | Ala | Ser | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gca | ccg | caa | tgg | ccg | aaa | tca | gcg | gca | ttg | cct | gcc | gct | gat | aac | act | 192 |
| Ala | Pro | Gln | Trp | Pro | Lys | Ser | Ala | Ala | Leu | Pro | Ala | Ala | Asp | Asn | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| tca | atg | aag | ccc | cat | cct | atg | gca | gcc | gat | ttg | ggg | tgg | cag | gat | ttt | 240 |
| Ser | Met | Lys | Pro | His | Pro | Met | Ala | Ala | Asp | Leu | Gly | Trp | Gln | Asp | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | aaa | gat | gcg | cgc | cta | aaa | gcc | ctg | att | aca | att | gcg | atc | cgc | gaa | 288 |
| Phe | Lys | Asp | Ala | Arg | Leu | Lys | Ala | Leu | Ile | Thr | Ile | Ala | Ile | Arg | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aac | cgc | gat | ttg | cgg | tca | gct | att | cag | gca | atc | ggt | gag | gcg | caa | gcc | 336 |
| Asn | Arg | Asp | Leu | Arg | Ser | Ala | Ile | Gln | Ala | Ile | Gly | Glu | Ala | Gln | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| aga | tat | cga | gtg | caa | cgc | gcg | tct | tta | ttg | ccc | gca | atc | ggt | ggc | act | 384 |
| Arg | Tyr | Arg | Val | Gln | Arg | Ala | Ser | Leu | Leu | Pro | Ala | Ile | Gly | Gly | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | gaa | gtg | atg | tat | cag | cag | cct | tcg | ggt | aaa | tcc | ggt | ttg | agt | ttt | 432 |
| Gly | Glu | Val | Met | Tyr | Gln | Gln | Pro | Ser | Gly | Lys | Ser | Gly | Leu | Ser | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| gcc | cca | ggt | gtc | ggt | gaa | gat | att | ccg | cgt | ttc | cat | tat | tat | tcg | atg | 480 |
| Ala | Pro | Gly | Val | Gly | Glu | Asp | Ile | Pro | Arg | Phe | His | Tyr | Tyr | Ser | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggt | atc | ggt | ttt | tct | tct | tat | gaa | att | gat | att | ttt | ggc | cgc | atc | cgc | 528 |
| Gly | Ile | Gly | Phe | Ser | Ser | Tyr | Glu | Ile | Asp | Ile | Phe | Gly | Arg | Ile | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| agt | tta | agc | aag | gag | gcg | gct | gaa | aga | gcc | ttg | atg | cag | gaa | gag | act | 576 |
| Ser | Leu | Ser | Lys | Glu | Ala | Ala | Glu | Arg | Ala | Leu | Met | Gln | Glu | Glu | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gcc | aga | ggc | acc | ttg | atc | acg | ctg | att | tcg | cag | gtg | gca | aat | agc | tat | 624 |
| Ala | Arg | Gly | Thr | Leu | Ile | Thr | Leu | Ile | Ser | Gln | Val | Ala | Asn | Ser | Tyr | |
| | | 195 | | | | | 200 | | | | | 205 | | | | |

| | | | | | | | | | | | | | | | | |
|---|---|---|---|---|---|---|---|---|---|---|---|---|---|---|---|---|
| att | gct | tgg | ttg | gca | gat | cga | gaa | act | ttg | aat | ctt | gcc | gaa | gaa | agc | 672 |
| Ile | Ala | Trp | Leu | Ala | Asp | Arg | Glu | Thr | Leu | Asn | Leu | Ala | Glu | Glu | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | cag | gct | gcc | aag | cgg | aat | ttg | gat | ttg | acg | cag | gct | ttg | ctt | gac | 720 |
| Tyr | Gln | Ala | Ala | Lys | Arg | Asn | Leu | Asp | Leu | Thr | Gln | Ala | Leu | Leu | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cat | ggt | gaa | gcg | agc | ctt | ttg | acg | gtc | aat | caa | gcc | gaa | acc | ttg | ttc | 768 |
| His | Gly | Glu | Ala | Ser | Leu | Leu | Thr | Val | Asn | Gln | Ala | Glu | Thr | Leu | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | caa | aaa | gca | gat | ttg | cgg | gag | cag | gca | aag | cgt | cag | atg | gca | tgg | 816 |
| Gln | Gln | Lys | Ala | Asp | Leu | Arg | Glu | Gln | Ala | Lys | Arg | Gln | Met | Ala | Trp | |
| | | | 260 | | | | | 265 | | | | | 270 | | | |

| | | | | | | | | | | | | | | | | |
|---|---|---|---|---|---|---|---|---|---|---|---|---|---|---|---|---|
| gaa | gaa | aat | aat | ctt | gtc | ttg | ctg | atc | ggg | cag | cct | ttg | ccc | gat | aat | 864 |

-continued

```
                Glu Glu Asn Asn Leu Val Leu Leu Ile Gly Gln Pro Leu Pro Asp Asn
                        275                 280                 285 ttg ccg ccg cct ttg ccc ttt ggt gag caa aat atc atc gaa gat tta          912
Leu Pro Pro Leu Pro Phe Gly Glu Gln Asn Ile Ile Glu Asp Leu
290                 295                 300 tcg ccc ggt ttg cct tcc gat ctt ttg gaa aac cgg cct gat att cga          960
Ser Pro Gly Leu Pro Ser Asp Leu Leu Glu Asn Arg Pro Asp Ile Arg
305                 310                 315                 320 gcc gcg gaa cat gat tta aag gcc gct aat gcg gat att ggg gca gca         1008
Ala Ala Glu His Asp Leu Lys Ala Ala Asn Ala Asp Ile Gly Ala Ala
                325                 330                 335 aga gcg gct ttt ttc cca agg ttg tct ttg acc tct tcg gtt ggt aac         1056
Arg Ala Ala Phe Phe Pro Arg Leu Ser Leu Thr Ser Ser Val Gly Asn
                340                 345                 350 tca agc ctt aag cct tcc cag att ttc act aca gcg gcg aat aca tgg         1104
Ser Ser Leu Lys Pro Ser Gln Ile Phe Thr Thr Ala Ala Asn Thr Trp
                355                 360                 365 gga ttc caa ccg gaa ttg acc gtg cct att ttt aac tgg ggg caa aat         1152
Gly Phe Gln Pro Glu Leu Thr Val Pro Ile Phe Asn Trp Gly Gln Asn
370                 375                 380 cgc gcc aat ttg aga att tcc aag gcc gag cgc gat atg aag atc acg         1200
Arg Ala Asn Leu Arg Ile Ser Lys Ala Glu Arg Asp Met Lys Ile Thr
385                 390                 395                 400 gcc tat caa aaa gca atc caa agt gct ttt cgt gat gtg tcg aat gct         1248
Ala Tyr Gln Lys Ala Ile Gln Ser Ala Phe Arg Asp Val Ser Asn Ala
                405                 410                 415 tta gtc gga cgc gat act tat cgt cgt gag gaa gtc gcc ttg act caa         1296
Leu Val Gly Arg Asp Thr Tyr Arg Arg Glu Glu Val Ala Leu Thr Gln
                420                 425                 430 gcg gcg gcg aag gct gaa aat aac tgg aat tta gcg cgt ttg cgt cag         1344
Ala Ala Ala Lys Ala Glu Asn Asn Trp Asn Leu Ala Arg Leu Arg Gln
                435                 440                 445 act caa ggc agt gat tcc gcc atc act atg ctt aat tac gag cag act         1392
Thr Gln Gly Ser Asp Ser Ala Ile Thr Met Leu Asn Tyr Glu Gln Thr
450                 455                 460 tat tac caa gcg gaa tat cag gcg ata cag aac agg gtt gcg cgt tat         1440
Tyr Tyr Gln Ala Glu Tyr Gln Ala Ile Gln Asn Arg Val Ala Arg Tyr
465                 470                 475                 480 caa aat ttg gtg acg ctc tat tcc gct ttg ggc ggt ggg gtg aaa gaa         1488
Gln Asn Leu Val Thr Leu Tyr Ser Ala Leu Gly Gly Gly Val Lys Glu
                485                 490                 495 aaa gcg gta tct ttg gat aaa act gat aaa gcc gcc cat tct gcc cat         1536
Lys Ala Val Ser Leu Asp Lys Thr Asp Lys Ala Ala His Ser Ala His
                500                 505                 510 tga                                                                      1539

<210> SEQ ID NO 14
<211> LENGTH: 512
<212> TYPE: PRT
<213> ORGANISM: Zymomonas mobilis

<400> SEQUENCE: 14

Met Thr Leu Phe Ser Ala Ser Ser Ala Leu Ile Lys Arg Ser Lys Lys
1               5                   10                  15

Gly Trp Arg Tyr Pro Val Thr Leu Phe Leu Ser Thr Asn Ile Leu Leu
                20                  25                  30

Ala Gly Cys Thr Met Ala Pro Lys Tyr His Arg Pro Ala Ala Ser Val
            35                  40                  45

Ala Pro Gln Trp Pro Lys Ser Ala Ala Leu Pro Ala Ala Asp Asn Thr
```

```
            50                  55                  60
Ser Met Lys Pro His Pro Met Ala Ala Asp Leu Gly Trp Gln Asp Phe
 65                  70                  75                  80

Phe Lys Asp Ala Arg Leu Lys Ala Leu Ile Thr Ile Ala Ile Arg Glu
                 85                  90                  95

Asn Arg Asp Leu Arg Ser Ala Ile Gln Ala Ile Gly Glu Ala Gln Ala
            100                 105                 110

Arg Tyr Arg Val Gln Arg Ala Ser Leu Leu Pro Ala Ile Gly Gly Thr
            115                 120                 125

Gly Glu Val Met Tyr Gln Gln Pro Ser Gly Lys Ser Gly Leu Ser Phe
130                 135                 140

Ala Pro Gly Val Gly Glu Asp Ile Pro Arg Phe His Tyr Tyr Ser Met
145                 150                 155                 160

Gly Ile Gly Phe Ser Ser Tyr Glu Ile Asp Ile Phe Gly Arg Ile Arg
                165                 170                 175

Ser Leu Ser Lys Glu Ala Ala Glu Arg Ala Leu Met Gln Glu Glu Thr
            180                 185                 190

Ala Arg Gly Thr Leu Ile Thr Leu Ile Ser Gln Val Ala Asn Ser Tyr
            195                 200                 205

Ile Ala Trp Leu Ala Asp Arg Glu Thr Leu Asn Leu Ala Glu Glu Ser
210                 215                 220

Tyr Gln Ala Ala Lys Arg Asn Leu Asp Leu Thr Gln Ala Leu Leu Asp
225                 230                 235                 240

His Gly Glu Ala Ser Leu Leu Thr Val Asn Gln Ala Glu Thr Leu Phe
                245                 250                 255

Gln Gln Lys Ala Asp Leu Arg Glu Gln Ala Lys Arg Gln Met Ala Trp
            260                 265                 270

Glu Glu Asn Asn Leu Val Leu Leu Ile Gly Gln Pro Leu Pro Asp Asn
            275                 280                 285

Leu Pro Pro Pro Leu Pro Phe Gly Glu Gln Asn Ile Ile Glu Asp Leu
290                 295                 300

Ser Pro Gly Leu Pro Ser Asp Leu Leu Glu Asn Arg Pro Asp Ile Arg
305                 310                 315                 320

Ala Ala Glu His Asp Leu Lys Ala Ala Asn Ala Asp Ile Gly Ala Ala
                325                 330                 335

Arg Ala Ala Phe Phe Pro Arg Leu Ser Leu Thr Ser Ser Val Gly Asn
            340                 345                 350

Ser Ser Leu Lys Pro Ser Gln Ile Phe Thr Thr Ala Ala Asn Thr Trp
            355                 360                 365

Gly Phe Gln Pro Glu Leu Thr Val Pro Ile Phe Asn Trp Gly Gln Asn
370                 375                 380

Arg Ala Asn Leu Arg Ile Ser Lys Ala Glu Arg Asp Met Lys Ile Thr
385                 390                 395                 400

Ala Tyr Gln Lys Ala Ile Gln Ser Ala Phe Arg Asp Val Ser Asn Ala
                405                 410                 415

Leu Val Gly Arg Asp Thr Tyr Arg Arg Glu Val Ala Leu Thr Gln
            420                 425                 430

Ala Ala Ala Lys Ala Glu Asn Asn Trp Asn Leu Ala Arg Leu Arg Gln
            435                 440                 445

Thr Gln Gly Ser Asp Ser Ala Ile Thr Met Leu Asn Tyr Glu Gln Thr
450                 455                 460

Tyr Tyr Gln Ala Glu Tyr Gln Ala Ile Gln Asn Arg Val Ala Arg Tyr
465                 470                 475                 480
```

```
Gln Asn Leu Val Thr Leu Tyr Ser Ala Leu Gly Gly Val Lys Glu
                485                 490                 495
Lys Ala Val Ser Leu Asp Lys Thr Asp Lys Ala Ala His Ser Ala His
            500                 505                 510

<210> SEQ ID NO 15
<211> LENGTH: 648
<212> TYPE: DNA
<213> ORGANISM: Zymomonas mobilis
<220> FEATURE:
<221> NAME/KEY: CDS
<222> LOCATION: (1)..(648)

<400> SEQUENCE: 15 atg aca ccc gat caa tcc gat aaa agc gcc tca aaa cgc cat gta ggg       48
Met Thr Pro Asp Gln Ser Asp Lys Ser Ala Ser Lys Arg His Val Gly
1               5                   10                  15 cgg cct cca cag ctt gat gaa aaa aaa cgc tgt gct ctt atc tta aaa       96
Arg Pro Pro Gln Leu Asp Glu Lys Lys Arg Cys Ala Leu Ile Leu Lys
                20                  25                  30 gcc gct gca acg gtg ctg caa acg cat ggc tat gat ggt tcc agt atg      144
Ala Ala Ala Thr Val Leu Gln Thr His Gly Tyr Asp Gly Ser Ser Met
            35                  40                  45 gat cgg gtt gcc agt cag gca ggc atg tca aaa aag acg gtg tat caa      192
Asp Arg Val Ala Ser Gln Ala Gly Met Ser Lys Lys Thr Val Tyr Gln
        50                  55                  60 atg ttc ccg tca aaa aag ata tta ttc acc aaa tta ctc gaa gat cgg      240
Met Phe Pro Ser Lys Lys Ile Leu Phe Thr Lys Leu Leu Glu Asp Arg
65                  70                  75                  80 ctt ttc tcg att gaa tgg cca gaa gaa aaa atc tgc gaa gac ccc gaa      288
Leu Phe Ser Ile Glu Trp Pro Glu Glu Lys Ile Cys Glu Asp Pro Glu
                85                  90                  95 gaa cat ctc tac tct cta ttg atc gcc att gct caa act att cta agg      336
Glu His Leu Tyr Ser Leu Leu Ile Ala Ile Ala Gln Thr Ile Leu Arg
                100                 105                 110 ccg gat cgg gtc tgc ctg ctt cgc att tta acc gtc gaa cat aaa tca      384
Pro Asp Arg Val Cys Leu Leu Arg Ile Leu Thr Val Glu His Lys Ser
            115                 120                 125 gaa gaa atg cgg cat att ttt agt gat att tta caa gga cat act gaa      432
Glu Glu Met Arg His Ile Phe Ser Asp Ile Leu Gln Gly His Thr Glu
        130                 135                 140 gac aat ttg acg cgc tgg ttc tcc gaa caa caa gac aaa ggt cgc tac      480
Asp Asn Leu Thr Arg Trp Phe Ser Glu Gln Gln Asp Lys Gly Arg Tyr
145                 150                 155                 160 cat ata tcc gac ccc ata aaa tat gcg gat atc att ttt aat atg acc      528
His Ile Ser Asp Pro Ile Lys Tyr Ala Asp Ile Ile Phe Asn Met Thr
                165                 170                 175 gta ggc agc ctg ttg ctc gat cga ctt ttc ggt tta gaa aaa cgc cct      576
Val Gly Ser Leu Leu Leu Asp Arg Leu Phe Gly Leu Glu Lys Arg Pro
                180                 185                 190 gtt gaa gac aat ttt cga gat gcc att tca att ttt tta cgg ggt atc      624
Val Glu Asp Asn Phe Arg Asp Ala Ile Ser Ile Phe Leu Arg Gly Ile
            195                 200                 205 cgt atc aat cct gaa aat gaa taa                                      648
Arg Ile Asn Pro Glu Asn Glu
        210                 215

<210> SEQ ID NO 16
<211> LENGTH: 215
<212> TYPE: PRT
<213> ORGANISM: Zymomonas mobilis
```

<400> SEQUENCE: 16

```
Met Thr Pro Asp Gln Ser Asp Lys Ser Ala Ser Lys Arg His Val Gly
1               5                   10                  15

Arg Pro Pro Gln Leu Asp Glu Lys Lys Arg Cys Ala Leu Ile Leu Lys
            20                  25                  30

Ala Ala Ala Thr Val Leu Gln Thr His Gly Tyr Asp Gly Ser Ser Met
        35                  40                  45

Asp Arg Val Ala Ser Gln Ala Gly Met Ser Lys Lys Thr Val Tyr Gln
    50                  55                  60

Met Phe Pro Ser Lys Lys Ile Leu Phe Thr Lys Leu Leu Glu Asp Arg
65                  70                  75                  80

Leu Phe Ser Ile Glu Trp Pro Glu Glu Lys Ile Cys Glu Asp Pro Glu
                85                  90                  95

Glu His Leu Tyr Ser Leu Leu Ile Ala Ile Ala Gln Thr Ile Leu Arg
            100                 105                 110

Pro Asp Arg Val Cys Leu Leu Arg Ile Leu Thr Val Glu His Lys Ser
        115                 120                 125

Glu Glu Met Arg His Ile Phe Ser Asp Ile Leu Gln Gly His Thr Glu
    130                 135                 140

Asp Asn Leu Thr Arg Trp Phe Ser Glu Gln Gln Asp Lys Gly Arg Tyr
145                 150                 155                 160

His Ile Ser Asp Pro Ile Lys Tyr Ala Asp Ile Ile Phe Asn Met Thr
                165                 170                 175

Val Gly Ser Leu Leu Leu Asp Arg Leu Phe Gly Leu Glu Lys Arg Pro
            180                 185                 190

Val Glu Asp Asn Phe Arg Asp Ala Ile Ser Ile Phe Leu Arg Gly Ile
        195                 200                 205

Arg Ile Asn Pro Glu Asn Glu
    210                 215
```

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
ccgtccttcc aattcgataa                                                 20

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
ccccaatatg accgaatcac                                                 20

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19

```
atcggcaatc atcaggaaag                                             20

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
ataccatcgc cttcatctgc                                             20
```

BIOCATALYSTS WITH ENHANCED INHIBITOR TOLERANCE

CROSS-REFERENCE TO RELATED APPLICATIONS

This application claims priority to U.S. Provisional Application No. 61/817,053, filed Apr. 29, 2013, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "13-22_ST25.txt," having a size in bytes of 84 kb and created on Aug. 4, 2014. Pursuant to 37 CFR §1.52(e)(5), the information contained in the above electronic file is hereby incorporated by reference in its entirety.

BACKGROUND

Biofuels derived from lignocellulosic biomass represent an alternative to petroleum based transportation fuels that take advantage of an abundant and renewable resource while not utilizing food crops as feedstocks. Cellulose and hemicellulose found in biomass, however, must first be converted to fermentable sugars, which are in turn converted to biofuels such as ethanol by fermentative organisms.

Numerous methods have been developed to convert biomass cellulose and hemicellulose fractions to sugars, including treatment with enzymes or chemicals. Pretreatment of biomass feedstocks with dilute acid is a technique frequently used to hydrolyze hemicellulose and improve the susceptibility of cellulose to enzymatic degradation, but this process can create compounds that inhibit the subsequent fermentation of sugars to biofuels. Methods to detoxify the pretreated feedstocks are often not economical or reduce the amount of sugars available for fermentation.

The existence of multiple inhibitors within feedstocks such as corn stover treated with dilute sulfuric acid restrains the growth of biocatalyst organisms leading to low ethanol yield and/or prolonged fermentation processes. Development of robust biocatalysts with enhanced tolerance to feedstock inhibitor compounds is needed for the economical production of biofuels.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide microorganisms comprising a genetic modification that increases the growth rate or biofuel production rate of the modified microorganism in the presence of a feedstock inhibitor compound relative to the growth rate or biofuel production rate of the unmodified microorganism.

In some embodiments, the genetic modification increases the expression or activity of a histidine kinase such as ZMO1162 relative to the expression or activity level in the unmodified microorganism. In others, the genetic modification decreases the expression or activity of (or abolishes the function of) a functional sigma-54 modulation protein such as ZMO0038 relative to the expression or activity level in the unmodified microorganism.

In certain embodiments, the microorganism is a bacterium, is a strain from the genus *Zymomonas*, or is a strain of *Zymomonas mobilis*.

In some embodiments, the feedstock is corn stover, or corn stover pretreated with a dilute acid.

In various embodiments, the feedstock inhibitor compound comprises furfural and the biofuel is ethanol.

Additional embodiments provide methods for producing a biofuel by culturing a microorganism as disclosed herein with a feedstock under conditions whereby the microorganism ferments the feedstock into a biofuel and isolating the biofuel from the culture.

In certain embodiments, the feedstock is lignocellulosic biomass, lignocellulosic biomass that has been pretreated with acid or enzymes to produce fermentable sugars, or acid pretreated corn stover hydrolysate.

In some embodiments, the feedstock comprises fermentable sugars and at least one inhibitor compound, which may be furfural.

In certain embodiments, the biofuel is ethanol.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleic acid (A) and amino acid (B) sequences for ZMO1162.

FIG. 2 shows the nucleic acid (A) and amino acid (B) sequences for ZMO0038.

FIG. 3 shows the nucleic acid (A) and amino acid (B) sequences for ZMO1598.

FIG. 4 shows the nucleic acid (A) and amino acid (B) sequences for ZMO1234.

FIG. 5 shows the nucleic acid (A) and amino acid (B) sequences for ZMO0282.

FIG. 6 shows the nucleic acid (A) and amino acid (B) sequences for ZMO0283.

FIG. 7 shows the nucleic acid (A) and amino acid (B) sequences for ZMO0285.

FIG. 8 shows the nucleic acid (A) and amino acid (B) sequences for ZMO0281.

DETAILED DESCRIPTION

Figure 9:
FIG. 9 shows the results of a hydrolysate plate assay for *Zymomonas* strains exhibiting enhanced tolerance to hydrolysate (OEL19, OEL22, OEL23, OEL26, OEL31), along with control strains 33C(pJL12), 33C and 8b.

Disclosed herein are biocatalysts for the production of biofuels. The biocatalysts are microorganisms that contain genetic modifications conferring tolerance to growth or fermentation inhibitors found in many cellulosic feedstocks, including those feedstocks that have been pretreated with chemicals such as dilute acids. Methods of converting cellulose-containing materials to fuels and chemicals, as well as methods of fermenting sugars to fuels and chemicals, using these biocatalysts are also disclosed.

Genetic loci have been identified that confer tolerance to inhibitor compounds found in feedstocks used for fermentation into biofuels. Modification of these loci in a microorganism may result in a biocatalyst organism able to grow at an increased rate or grow to a higher concentration in culture relative to the unmodified organism in the presence of inhibitor compounds. Modification of these loci in a microorganism may also result in a biocatalyst organism able to produce a biofuel at a higher rate or to a higher concentration in culture relative to the unmodified organism in the presence of inhibitor compounds. An organism with enhanced tolerance to an inhibitor compound exhibits enhanced growth or biofuel production in the presence of the inhibitor compound in comparison to a less tolerant organism.

As used herein, the term "inhibitor compound" or "inhibitor" refers to a compound that interferes with the overall sugar fermentative capabilities of an organism. Many inhibitor compounds exist that interfere with the growth or fermentation properties of biocatalyst organisms, including those naturally found in biomass feedstocks, generated by pretreatment of the feedstock with chemicals such as dilute acids or bases, or generated via fermentation of a feedstock-derived sugars by an organism. Examples include acetate or furfural compounds commonly found in acid pretreated corn stover. Additional inhibitor compounds include furaldehydes such as hydroxymethylfurfural, weak acids (e.g., acetic acid, levulinic acid or formic acid), syringic acid, p-hydroxybenzoic acid, vanillin, terpenoids, phenolics and aromatics (e.g., benzoate). Inhibitor compounds also include metabolic byproducts (e.g., lactate or acetate) and an increased concentration of the fermentation product being generated (e.g., ethanol).

A genetic modification conferring tolerance may include any modification that results in a gain or loss of function at a particular genetic locus. Such modifications may be within sequences that encode gene products or in noncoding regions that influence gene expression. Modifications may also include the insertion of sequences known to increase or decrease gene expression (e.g., promoters, enhancers and the like). For example, the genetic modification may be an insertion into a gene coding sequence that ablates or attenuates the expression of the polypeptide encoded by the gene. In other embodiments, the genetic modification may be the insertion of a promoter into a noncoding region of a host genome that results in enhanced expression of a gene product. In still other embodiments, the genetic modification may result in a truncated or disrupted gene encoding an altered polypeptide with an augmented or reduced activity relative to the wild type polypeptide.

In certain embodiments, the genetic modification may be a modification of a gene encoding a histidine kinase, such as a PhoR protein or homologs thereof. One exemplary histidine kinase gene from Z. mobilis is designated ZMO1162. The nucleotide sequence for ZMO1162 (SEQ ID NO:1) and the amino acid sequence encoded by ZMO1162 (SEQ ID NO:2) are provided in FIG. 1. However, additional histidine kinases from other bacteria or microorganisms may also be modified. Examples include the PhoR histidine kinase from Escherichia coli or Bacillus subtilis, as well as the SLN1 gene product from yeast such as S. cerevisiae.

The genetic modification may be the overexpression of a histidine kinase gene or a modification of the histidine kinase gene that results in a histidine kinase with increased enzymatic activity. The modification may result in increased expression or activity of an endogenous histidine kinase or the expression of an exogenous histidine kinase (e.g., via introducing an expression vector including a nucleic acid encoding a histidine kinase) in a microorganism to increase overall expression or activity levels. In certain embodiments, the modification may be the insertion of a promoter into the genome of a microorganism near the gene encoding a histidine kinase to increase expression of the histidine kinase. For example, the promoter Pgap may be inserted into the genome of a Zymomonas strain to increase expression of ZMO1162.

In other embodiments, the genetic modification may be a modification of a gene encoding a sigma-54 modulation protein or a homolog thereof. One exemplary sigma-54 modulation protein from Z. mobilis is designated ZMO0038. The nucleotide sequence for ZMO0038 (SEQ ID NO:3) and the amino acid sequence encoded by ZMO0038 (SEQ ID NO:4) are provided in FIG. 2. However, additional sigma-54 modulation proteins from other bacteria or microorganisms may also be modified. Examples include the Hst23 protein (UniProtKB Entry P28368) from Bacillus subtilis and the Ccel 0370 protein from Clostridium cellulolyticum. The N-terminal portion of ZMO0038 contains a conserved domain of Ribosome-associated Inhibitor A (RaiA, also known as Protein Y [PY], YfiA, and SpotY), which is a stress-response protein that binds the ribosomal subunit interface and arrests translation by interfering with aminoacyl-tRNA binding to the ribosomal A site. Suitable sigma-54 modulation proteins also include proteins containing a RaiA domain.

The genetic modification may be an alteration of a gene resulting in the deletion of a functional sigma-54 modulation protein by ablation of the gene or other alteration leading to expression of a nonfunctional sigma-54 modulation protein. The modification may result in decreased expression or activity of an endogenous sigma-54 modulation protein. In certain embodiments, the modification may be the insertion of a nucleotide sequence into the genome of a microorganism within the gene encoding a sigma-54 modulation protein to decrease or ablate the expression of the functional sigma-54 modulation protein. For example, a nucleotide sequence may be inserted into the genome of a *Zymomonas* strain to reduce or ablate expression of ZMO0038.

In certain embodiments, the genetic modification may be a modification of a gene encoding a 1-deoxy-D-xylulose-5-phosphate synthase (Dxs) or a homolog thereof. Two exemplary Dxs enzymes from *Z. mobilis* are designated ZMO1598 and ZMO1234. The nucleotide sequence for ZMO1598 (SEQ ID NO:5) and the amino acid sequence encoded by ZMO1598 (SEQ ID NO:6) are provided in FIG. 3. The nucleotide sequence for ZMO1234 (SEQ ID NO:7) and the amino acid sequence encoded by ZMO1234 (SEQ ID NO:8) are provided in FIG. 4. However, additional Dxs enzymes from other bacteria or microorganisms may also be modified.

The genetic modification may be an alteration of a gene resulting in the deletion of a functional Dxs enzyme by ablation of the gene or other alteration leading to expression of a nonfunctional Dxs enzyme. The modification may result in decreased expression or activity of an endogenous Dxs enzyme. In certain embodiments, the modification may be the insertion of a nucleotide sequence into the genome of a microorganism within the gene encoding a Dxs enzyme to decrease or ablate the expression of the functional Dxs enzyme. For example, a nucleotide sequence may be inserted into the genome of a *Zymomonas* strain to reduce or ablate expression of ZMO1598 or ZMO1234.

In some embodiments, the genetic modification may be a modification of a gene encoding a component of a membrane-bound efflux transport system. For example, the genes from *Z. mobilis* designated ZMO0282, ZMO0283, and ZMO0285 are located on the same operon and exhibit similarity to genes from *E. coli* that function as components of efflux transporter complexes. The nucleotide sequence for ZMO0282 (SEQ ID NO:9) and the amino acid sequence encoded by ZMO0282 (SEQ ID NO:10) are provided in FIG. 5. The nucleotide sequence for ZMO0283 (SEQ ID NO:11) and the amino acid sequence encoded by ZMO0283 (SEQ ID NO:12) are provided in FIG. 6. The nucleotide sequence for ZMO0285 (SEQ ID NO:13) and the amino acid sequence encoded by ZMO0285 (SEQ ID NO:14) are provided in FIG. 7. However, additional membrane-bound efflux transport systems from other bacteria or microorganisms may also be modified.

The genetic modification may be an alteration of a gene resulting in the deletion of a functional efflux transport system protein by ablation of the gene or other alteration leading to expression of a nonfunctional protein. The modification may result in decreased expression or activity of an endogenous efflux transport system protein. In certain embodiments, the modification may be the insertion of a nucleotide sequence into the genome of a microorganism within the gene encoding an efflux transport system protein to decrease or ablate the expression of the functional protein. For example, a nucleotide sequence may be inserted into the genome of a *Zymomonas* strain to reduce or ablate expression of ZMO0282, ZMO0283, or ZMO0285. In certain embodiments, the modification may result in the reduced expression of at least one gene within the operon containing ZMO0282, ZMO0283, and ZMO0285.

The genetic modification may also be to a TetR family repressor, such as ZMO0281. The nucleotide sequence for ZMO0281 (SEQ ID NO:15) and the amino acid sequence encoded by ZMO0281 (SEQ ID NO:16) are provided in FIG. 8. The genetic modification may be the overexpression of a repressor gene that may result in lower expression or activity of an efflux transport system protein. The modification may result in increased expression or activity of the repressor (e.g., via introducing an expression vector including a nucleic acid encoding a repressor) in a microorganism to increase overall expression or activity levels. In certain embodiments, the modification may be the insertion of a promoter into the genome of a microorganism near the gene encoding a TetR family repressor to increase its expression. For example, the promoter Pgap may be inserted into the genome of a *Zymomonas* strain to increase expression of ZMO0281.

Without wishing to be bound to any particular theory, the ZMO0281 gene product may act to repress the expression of ZMO0282, ZMO0283, and ZMO0285. ZMO0281 has similarity to AcrR of *E. coli*, while the genes ZMO0282 and ZMO0283 have structural similarities to AcrA and AcrB. In *E. coli*, AcrAB is part of the RND family of efflux transporters and is implicated in tolerance to organic solvents. Its deletion in *E. coli* results in a hypersensitivity to organic solvents. It is repressed by the AcrR regulator, a DNA binding protein which binds to the operator element for both acrAB and acrR. AcrAB complexes with TolC, an outer membrane protein, which has similarities in function to the ZMO0285 gene product of *Zymomonas*. Unlike *E. coli*, disruption of ZMO0282 and ZMO0283 and overexpression of ZMO0281 do not lead to increased sensitivity to furfural. Instead, the opposite effect is observed in *Z. mobilis*, which indicates that the efflux pump complex involving ZMO0282 and ZMO0283 may play a negative role in furfural resistance.

In exemplary embodiments, the microorganism may be a bacterium such as one from the genus *Zymomonas*, from the species *Zymomonas mobilis*, or a strain of *Z. mobilis* such as *Z. mobilis* strains 33C, 8b, 39676, CP4, or ZM4. *Z. mobilis* has proven to be an extremely valuable organism in the conversion of biomass-derived sugars to ethanol. In addition to its fermentative abilities, *Z. mobilis* cells expressing nucleic acids encoding cellulases and other enzymes may also play a significant role in the degradation of lignocellulosic biomass. Given the proven adeptness of *Z. mobilis* in industrial-scale fermentation, a demonstrated ability to express and secrete high levels of active cellulases, *Z. mobilis* may be particularly suitable as organism for both the degradation of biomass to sugars and the subsequent fermentation of sugars to biofuels. Additional suitable microorganisms include bacteria such as *E. coli* or strains from the genera *Clostridium* (e.g., *C. cellulolyticum* or *C. thermocellum*) or *Bacillus* (e.g., *B. subtilis*) and yeasts such as those from the genus *Saccharomyces* (e.g., *S. cerevisiae* or *S. pombe*) or *Pichia* (e.g., *P. pastoris*).

Suitable *Zymomonas* cells include cells previously transformed with expression vectors containing genes useful in the degradation of biomass or the fermentation of sugars into ethanol and other industrial chemicals. Examples include *Zymomonas* cells capable of utilizing pentose sugars such as xylose or arabinose as a carbon source, as described, for example in U.S. Pat. Nos. 5,514,583; 5,843,760; 6,566,107; and 7,223,575.

Although the production of ethanol from acid pretreated corn stover hydrolysate is exemplified herein, a variety of feedstocks and biofuels are contemplated. Exemplary biofuels include ethanol, propanol, butanol and other alcohols, as well as advanced hydrocarbon biofuel candidates and intermediates. Feedstocks include any capable of supplying fermentable sugars, including sugars generated by subjecting cellulosic materials to heat, enzymes, or chemicals. Typical biofuel production processes involve pretreating biomass to convert cellulose and hemicellulose to oligosaccharides, which are then enzymatically hydrolyzed to simple sugars, which are in turn fermented by microorganisms to biofuels. Suitable feedstocks include any biomass or cellulose-containing materials such as acid pretreated corn stover hydrolysate.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single-and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

A nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function. Nucleic acid molecules may also be used in methods to ablate or attenuate the expression of a gene in a host cell using gene targeting and knock-out techniques. Suitable nucleic acids also include fragments or variants Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, the nucleic acids are identical to the sequences represented as SEQ ID NO:1, SEQ ID NO:3, SEQ ID NO:5, SEQ ID NO:7, SEQ ID NO:9, SEQ ID NO:11, SEQ ID NO:13 or SEQ ID NO:15. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:1, SEQ ID NO:3, SEQ ID NO:5, SEQ ID NO:7, SEQ ID NO:9, SEQ ID NO:11, SEQ ID NO:13 or SEQ ID NO:15. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing a query sequences to sequences in publicly available sequence databases (NCBI) using the BLASTN2 algorithm.

Embodiments of the nucleic acids include those that encode a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:14 and SEQ ID NO:16, or functional equivalents thereof. A functional equivalent includes fragments or variants that exhibit the ability to function as a signal sequence and direct the extracellular secretion of proteins. As a result of the degeneracy of the genetic code, many nucleic acid sequences can encode a polypeptide having the amino acid sequence of SEQ ID NO:2, SEQ ID NO:4, SEQ ID NO:6, SEQ ID NO:8, SEQ ID NO:10, SEQ ID NO:12, SEQ ID NO:14 and SEQ ID NO:16. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect. For example, conditions for nucleic acid hybridizations are explained in F. M. Ausubel et al. (eds), 1995, Current Protocols in Molecular Biology, John Wiley and Sons, Inc., New York, N.Y., the teachings of which are hereby incorporated by reference.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Oligonucleotides that are fragments of the nucleotide sequences disclosed herein and antisense nucleic acids that are complementary, in whole or in part, to the nucleotide sequences disclosed herein are contemplated herein. Oligonucleotides may be used as primers or probes or for any other use known in the art. Antisense nucleic acids may be used, for example, to inhibit gene expression when introduced into a cell or for any other use known in the art. Oligonucleotides and antisense nucleic acids can be produced by standard techniques known in the art.

Also disclosed herein are recombinant vectors, including expression vectors, containing a gene expressing a histidine kinase, sigma-54 modulation protein, Dxs enzyme, component of a membrane-bound efflux transport system, or TetR family repressor (e.g., SEQ ID NO:1, SEQ ID NO:3, SEQ ID NO:5, SEQ ID NO:7, SEQ ID NO:9, SEQ ID NO:11, SEQ ID NO:13 or SEQ ID NO:15 or homologs thereof). A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A recombinant vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Recombinant vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell (see, e.g., D. V. Goeddel, Methods Enzymol. 185:3-7). The expression vectors may contain elements that allow for constitutive expression or inducible expression of the protein or proteins of interest. For example, vectors comprising the Ptac promoter allow for constitutive expression in the absence of the lad gene, but expression may be induced by the addition of isopropyl-β-D-thiogalactopyranoside (IPTG) when the vector also contains the lad gene. Numerous inducible and constitutive expression systems are known in the art.

Several regulatory elements (e.g., promoters and terminators) have been isolated and shown to be effective in the transcription and translation of heterologous proteins in the various hosts. Such regulatory regions, methods of isolation, manner of manipulation, etc. are known in the art. To obtain expression in eukaryotic cells, terminator sequences, polyadenylation sequences, and enhancer sequences that modulate gene expression may be required. Sequences that cause amplification of the gene may also be desirable. Suitable promoters include the Ptac, PBAD, PGAP, PEno or PPdc promoters, among others. Suitable terminators include the T1T2 and T7 terminators, among others.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the nucleic acid sequences described herein for simple cloning or protein expression.

Suitable expression vectors also include pZB188, pFlag-CTC, or p25143 or other vectors comprising the Ptac, PBAD, P GAP, PEno or PPdc promoters. In certain embodiments, an expression vector may include an expression cassette comprising a promoter, gene and terminator sequence.

It will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The nucleic acids, including parts or all of expression vectors, may be isolated directly from cells, or, alternatively, the polymerase chain reaction (PCR) method can be used to produce the nucleic acids. Primers used for PCR can be synthesized using the sequence information provided herein and can further be designed to introduce appropriate new restriction sites, if desirable, to facilitate incorporation into a given vector for recombinant expression. The nucleic acids can be produced in large quantities by replication in a suitable host cell (e.g., prokaryotic or eukaryotic cells such as bacteria, yeast, insect or mammalian cells). The production and purification of nucleic acids are described, for example, in Sambrook et al., 1989; F. M. Ausubel et al., 1992, Current Protocols in Molecular Biology, J. Wiley and Sons, New York, N.Y.

The nucleic acids described herein may be used in methods for production of proteins or polypeptides through incorporation into cells, tissues, or organisms. In some embodiments, a nucleic acid encoding all or part of ZMO1162 (SEQ ID NO:2) or ZMO0038 (SEQ ID NO:4) or any other amino acid sequence disclosed herein, or a functional fragment thereof, may be incorporated into a vector for expression of the encoded polypeptide in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include bacteria, archea, insect, fungi (e.g., yeast), plant, and animal cells (e.g., mammalian). Specific examples include *Zymomonas mobilis, Escherichia coli, Bacillus subtilis*, and *Saccharomyces cerevisiae*. Host cells can be either untransfected cells or cells that are already transfected with at least one other recombinant nucleic acid molecule.

Host cells can be transformed, transfected, or infected as appropriate by any suitable method including electroporation, calcium chloride-, lithium chloride-, lithium acetate/polyethylene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection (see, Kubo et al., FEBS Letts. 241:119). Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Biocatalyst microorganisms may be cultured in an appropriate fermentation medium. An appropriate, or effective, fermentation medium refers to any medium in which a microorganism, when cultured, is capable of expressing polypeptides, catalyzing the production of sugars from lignocellulosic biomass, or fermenting sugars to biofuels. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth and protein production of the particular organism. The fermentor can be aerated in order to supply the oxygen necessary for fermentation and to avoid the excessive accumulation of carbon dioxide produced by fermentation. Culture media and conditions for various host cells are known in the art. Exemplary conditions for the culture of bacteria such as *Z. mobilis* can be found, for example, in Senthilkumar et al., Arch. Microbiol. 191:529-41 and Arfman et al., J. Bacteriol. 174:7370-8.

As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequence of SEQ ID NO:2, SEQ ID NO:4, SEQ ID NO:6, SEQ ID NO:8, SEQ ID NO:10, SEQ ID NO:12, SEQ ID NO:14 and SEQ ID NO:16, or may include up to a certain integer number of amino acid alterations. Such protein or polypeptide variants retain functionality (e.g., as histidine kinases, sigma-54 modulation proteins, Dxs enzymes, components of a membrane-bound efflux transport system, or TetR family repressors), and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:2, SEQ ID NO:4, SEQ ID NO:6, SEQ ID NO:8, SEQ ID NO:10, SEQ ID NO:12, SEQ ID NO:14 and SEQ ID NO:16 and possess one or more functions ascribed to the polypeptide (e.g., histidine kinase, sigma-54 modulation, Dxs enzyme, membrane-bound efflux transport, or TetR family repressor activity). Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Modified polypeptides, including those with post-translational modifications, are also contemplated herein. Isolated polypeptides may be modified by, for example, phosphorylation, methylation, farnesylation, carboxymethylation, geranyl geranylation, glycosylation, acetylation, myristoylation, prenylation, palmitation, amidation, sulfation, acylation, or other protein modifications. They may also be modified with a label capable of providing a detectable signal, either directly or indirectly, including, but not limited to, radioisotopes and fluorescent compounds. The polypeptides may be useful as antigens for preparing antibodies by standard methods. Monoclonal and polyclonal antibodies that specifically recognize the polypeptides disclosed herein are contemplated.

Polypeptides may be retrieved, obtained, or used in "substantially pure" form, a purity that allows for the effective use of the protein in any method described herein or known in the art. For a protein to be useful in any of the methods described herein or in any method utilizing enzymes of the types described herein, it is substantially free of contaminants, other proteins and/or chemicals that might interfere or that would interfere with its use in the method (e.g., that might interfere with enzyme activity), or that at least would be undesirable for inclusion with a protein.

The biocatalyst organisms described herein may be used to ferment simple sugars directly to biofuels. The organisms are contacted with the sugars in a fermentation broth under conditions suitable for fermenting the sugars to biofuels. Fermentation conditions vary with the organism, feedstock or sugar used, or with the desired biofuel product, and can be determined by those skilled in the art. For the fermentation of acid pretreated corn stover hydrolysate to ethanol using a strain of *Zymomonas*, for example, conditions may be those set forth in Example 1 below.

The biocatalyst organisms described herein may also be used as part of an integrated process to derive biofuels from raw biomass or cellulosic materials. Typically, raw cellulosic biomass material is pretreated in order to convert, or partially convert, cellulosic and hemicellulosic components into enzymatically hydrolyzable components (e.g., oligosaccharides). The pretreatment process may also serve to separate the cellulosic and hemicellulosic components from solid lignin components also present in the raw cellulosic material. The pretreatment process typically involves reacting the raw cellulosic biomass material, often as a finely divided mixture or slurry in water, with an acid, such as sulfuric acid. The pretreated biomass may then be treated with a saccharification step in which oligosaccharides are enzymatically hydrolyzed into simple sugars. The free sugars or oligosaccharides produced in the saccharification step are then subjected to fermentation conditions for the production of a biofuel. Fermentation can be accomplished by combining one or more biocatalyst microorganisms with the produced sugars under conditions suitable for fermentation.

Methods for breaking down lignocellulose and lignocellulose-containing biomass are also disclosed herein. Biocatalysts containing the genetic modifications described herein or additional modifications that aid in the breakdown of lignocellulose may be brought into contact with a lignocellulose-containing biomass (for example, by culturing the organism in the presence of the lignocellulose-containing biomass) in the presence of cellulolytic or oligosaccharide degrading enzymes to result in its degradation. Treated biomass is typically degraded into simpler forms of carbohydrates, and in some cases glucose, which may then be used in the formation of ethanol or other industrial chemicals, as is known in the art. Biomass degradation may be achieved by culturing a microorganism in media supplemented with a source of lignocellulose-containing biomass, in addition to media components necessary for growth of the microorganism. In addition to the use of lignocellulose-containing biomass as an energy source for the host, the growth media may need to be supplemented with additional components including, but not limited to, yeast extract. Multiple enzymes may be needed to utilize lignocellulose-containing biomass as a primary source of energy. Such enzymes may be expressed by one or more microorganism, or purified enzymes or mixtures of enzymes may be directly added to the culture. For example, endoglucanase, exoglucanase, and β-glucosidase activities may be required to fully degrade cellulosic materials into fermentable sugars. These enzymatic activities can arise from individual enzymes, or in some cases, multiple types of cellulolytic activity can arise from the same enzyme. Further, there are different enzymatic activities that can substitute for other activities. For instance, processive endoglucanases can have overlapping roles with exoglucanases.

Lignocellulose-containing biomass may be derived from any source known in the art, and may be degraded to oligosaccharides and simple sugars using enzymes or chemicals. Biofuels such as ethanol may be subsequently produced from the fermentation of sugars derived from the cellulosic materials. Examples include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure. Biomass samples may be processed or pretreated using known methods prior to or after degradation. Examples of pretreatment methods can be found, for example, in Galbe et al., Adv Biochem Eng Biotechnol.; 108:41-65.

A lignocellulosic biomass or other cellulosic feedstock may be subjected to pretreatment at an elevated temperature in the presence of water, a dilute acid, concentrated acid or dilute alkali solution for a time sufficient to at least partially hydrolyze the hemicellulose components before subsequent enzymatic treatment or fermentation to biofuels. Additional suitable pretreatment regimens include ammonia fiber expansion (AFEX), treatment with hot water or steam, or lime pretreatment.

The resulting products after cellulose degradation and fermentation may be isolated or purified. After fermentation, for example, a biofuel may be separated from the fermentation broth by any conventional technique known to separate alcohol from aqueous solutions, including evaporation, distillation, solvent extraction and membrane separation. Solids such as microorganisms may be removed before separation to enhance separation efficiency. Fermentation products may also be converted to products other than ethanol. Examples include conversion to higher alcohols, hydrocarbons, or other advanced fuels via biological or chemical pathways, or combination thereof.

EXAMPLES

Example 1

The following materials and methods were used in the Examples that follow:
Construction of the Overexpression Mutant Library A transposon insertion system (Epicentre Biotechnologies, Madison, Wis.) was used to generate transposomes for the transposition. For the construction of "Super Pgap" overexpression mutant library (OEL), the "Super Pgap" promoter was cloned into an integrative plasmid (pMOD2Splox), and the fragment digested with PvuII containing ME-loxP-Pgap-Sp-loxP-ME was gel purified and treated with transposases, in 16-20% glycerol at room temperature for 30 minutes before the electroporation transformation. Transformants were selected on RMG2Sp200 plates, and the colonies were collected.
Enrichment of 33C Overexpression Mutant Library in Selective Media Frozen library vials were thawed and revived before spreading on selective media including RMA2 broth and plate, RMG plate with arabitol, and 40% hydrolysate plates. Colonies with large size were selected for continuous adaptation on the selective conditions.
Overexpression of Genes Related to Inhibitor Tolerance in 33C and 8b Background Overexpression constructs for genes related to pretreatment inhibitor tolerance, which were identified from transcriptomics studies under Hydrolysate Toxicity subtask, were transformed into 33C and 8b.
Inhibitor Tolerance and Non-Native Sugar Utilization Evaluation Strains were revived from overnight culture with $OD_{600nm}$ adjusted to 1.5 using RM-, 10 µL seed culture was added into 300 µL media with an initial $OD_{600nm}$ about 0.05. Bioscreen assay was conducted at 33° C. without shaking.
Sequencing

*Zymomonas* genomic DNA samples were prepared from overnight cultures using Qiagen's DNeasy Blood & tissue Kit. Genomic DNA was extracted and sequenced using primers 126604-F and 126604-R, and the insertional location was identified through sequencing analysis.
Fermentation of Acid Pretreated Corn Stover Rich medium (RM) consisting of 10 g/L yeast extract and 2 g/L $KH_2PO_4$ was added to neutralized saccharified whole slurry, and the fermentation were performed in BioStat-Q Plus fermentors at a 300-mL working volume with an initial inoculum at an $OD_{600 nm}$ value of approximately 1.0 with pH controlled to 5.8 with 4M KOH at 33° C., 300 rpm.
RNA Extraction, cDNA Synthesis, and qRT-PCR Total RNA was extracted from cell pellets growing in RMG5 or RMX5 resuspended in TRIzol reagent (Invitrogen, CA). Each total RNA preparation was treated with RNase-free DNase I (Ambion, TX) to digest residual genomic DNA and subsequently purified using the RNeasy Mini Kit (Qiagen, CA). Total cellular RNA was quantified with a NanoDrop ND-1000 spectrophotometer (NanoDrop Technologies, DE) and RNA quality was assessed with Agilent Bioanalyzer (Agilent, CA). Purified RNA of high quality was used as the template to generate cDNA using Bio-Rad iScript cDNA Synthesis Kit (Bio-Rad, CA). cDNA was then used as template for qRT-PCR using Bio-Rad iQ SYBR Green supermix with a Bio-Rad CFX96 Touch Real-Time PCR Detection System (Bio-Rad, CA).
Chemical Analysis Concentrations of ethanol, HMF, furfural, lactic acid, glycerol and acetic acid present in hydrolyzates were determined from filtered sample supernatants that were analyzed by high performance liquid chromatography (HPLC) Agilent1100 series (Agilent, CA) utilizing a BioRad HPX-87H organic acids column and Cation $H^+$ guard cartridge (Bio-Rad, CA) operating at 55° C. A refractive index detector was used for compound detection. Dilute sulfuric acid (0.01 N) was used as the isocratic mobile phase at a flow rate of 0.6 ml min-1. Analysis of furfural conversion products was performed on a C-18 column starting with 10% acetonitrile as the mobile phase at a flow rate of 0.5 mL/min and ending with 90% acetonitrile over a 35 minute gradient.

Example 2

Selection of Biocatalysts Tolerant to Hydrolysate

A transposon-based overexpression construct was created and used to build a mutant library of *Z. mobilis*. A library of a randomly integrated strong promoters ("Super Pgap") throughout the genome of an arabinose utilizing *Zymomonas* strain (33C; an engineered strain capable of utilizing glucose, xylose, and arabinose) was generated. This library was screened to identify mutants with increased ability to tolerate hydrolysate—about 30,000 mutant isolates were pooled and hydrolysate-tolerant candidates were selected on agar plates containing 40% pretreated corn stover hydrolysate. Five candidates from the over-expression library exhibiting improved growth in the presence of 40% hydrolysate were selected by continuously transferring the single colony onto 40% hydrolysate agar plate eight times to stabilize the phenotype of hydrolysate tolerance. These five candidates are shown in FIG. 9.

Figure 10A:
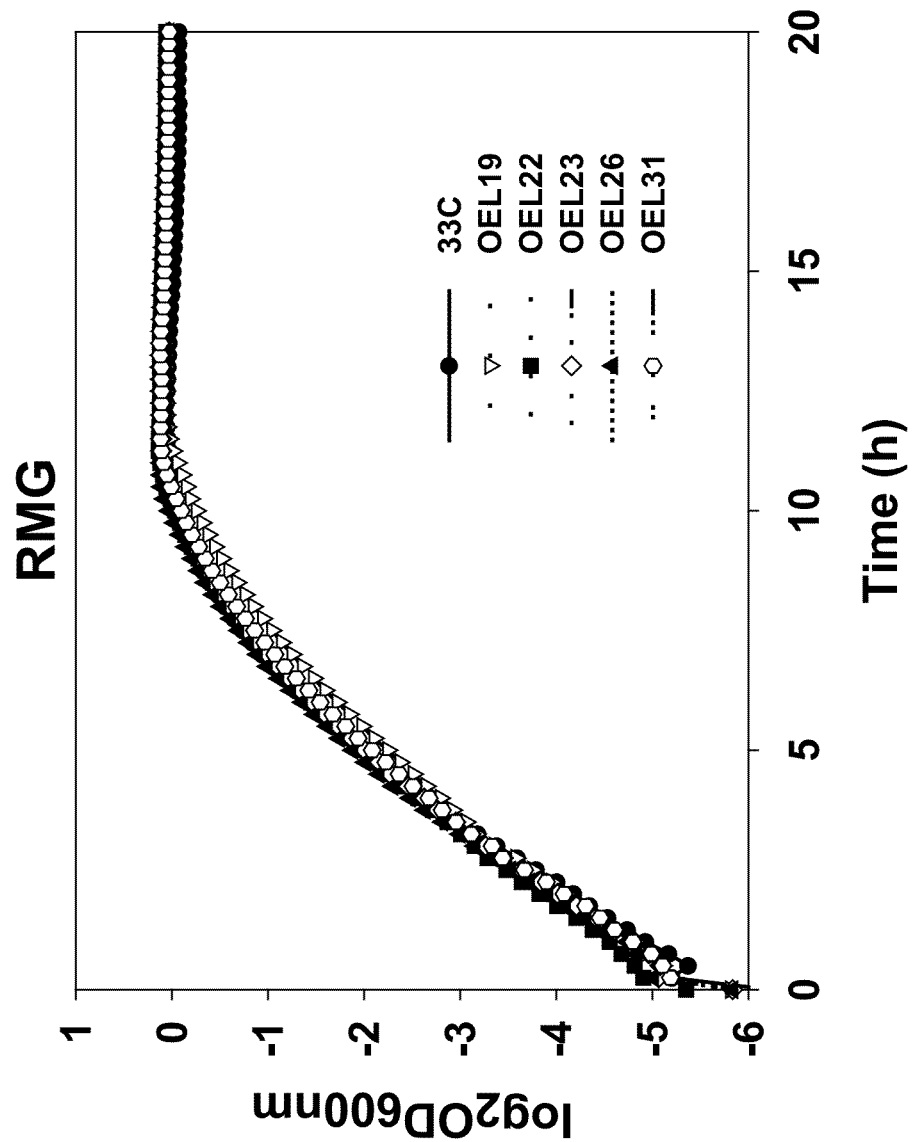
FIG. 10 shows growth assay results for five strains (OEL19, 22, 23, 26, and 31) with enhanced hydrolysate tolerance and the parental strain 33C in media only (A), media supplemented with 2 g/L furfural (B), and media supplemented with of 8% (v/v) ethanol.
Figure 10B:
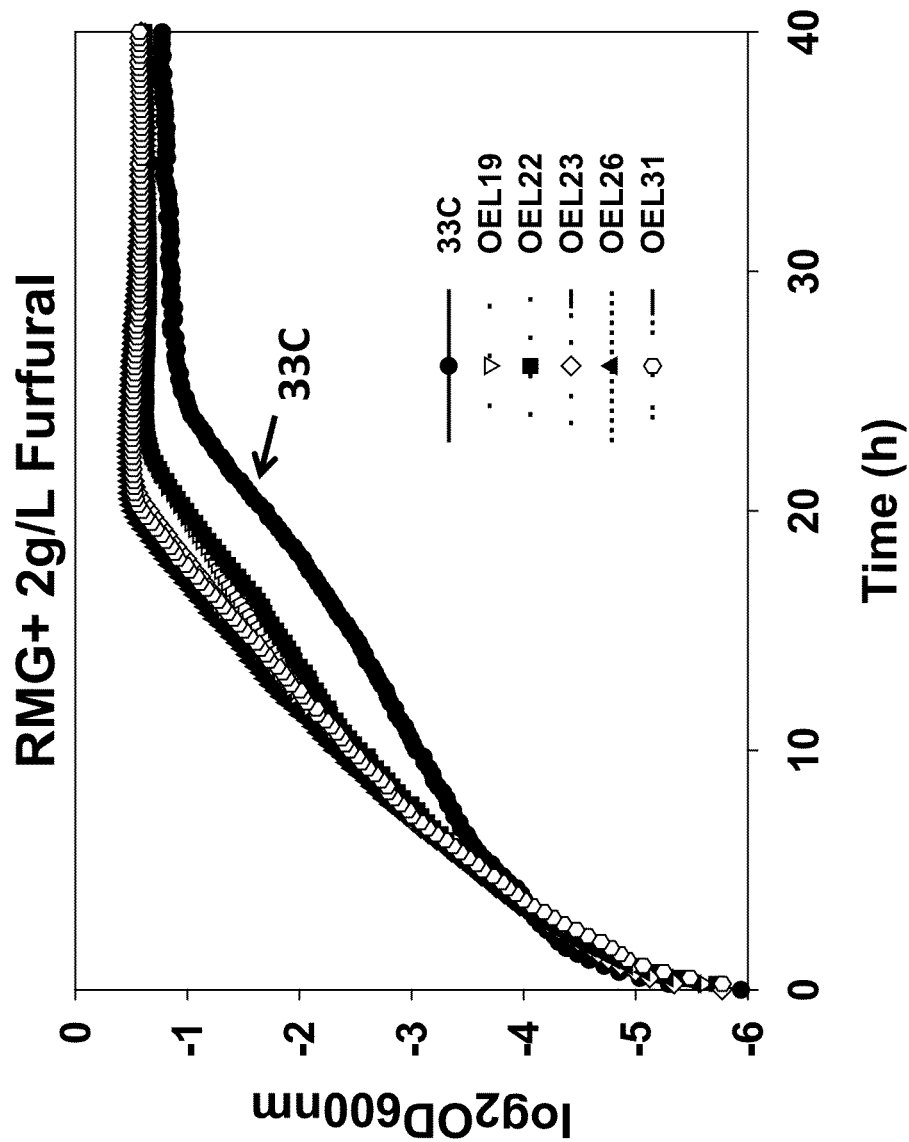
Figure 10C:
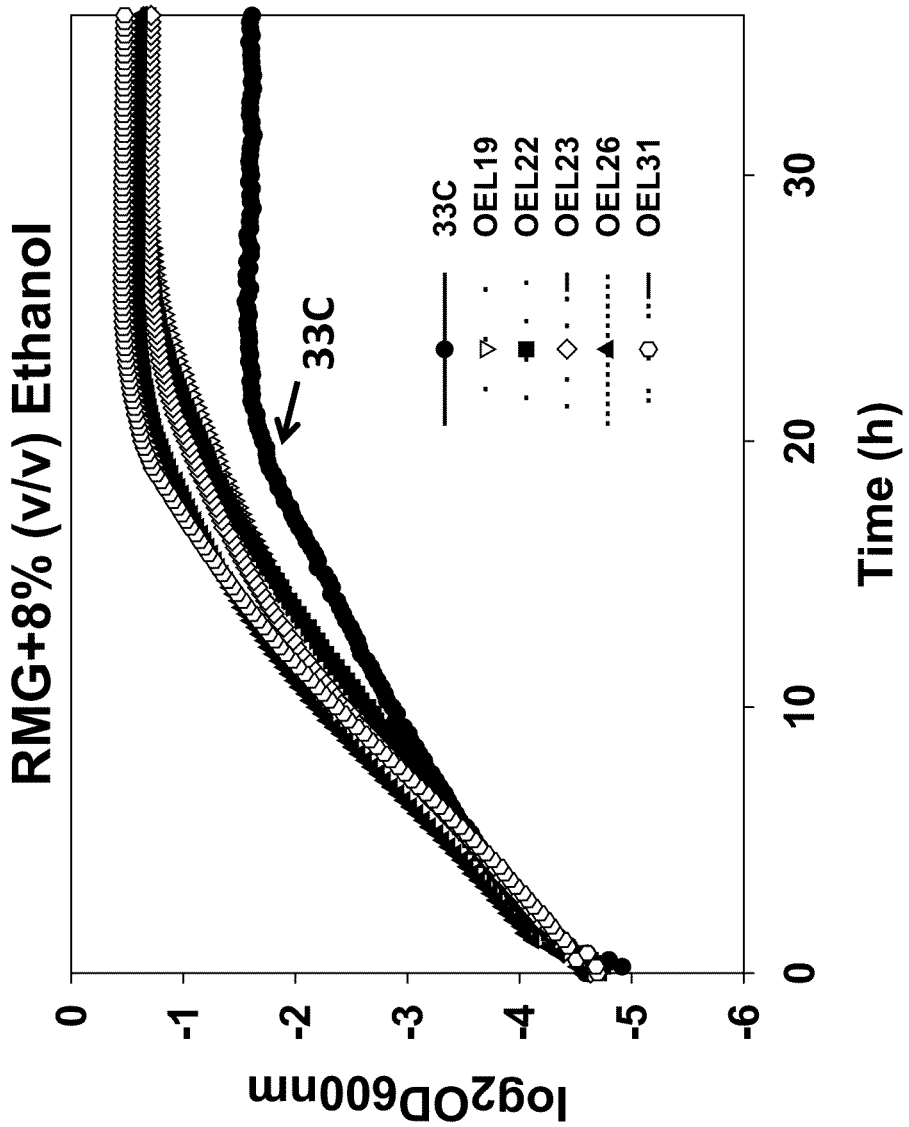

A Bioscreen (Growth Curves USA, Piscataway, N.J.) high-throughput growth assay was used to characterize the phenotypic changes associated with these five mutant strains in the presence of different sugar sources (glucose, xylose or arabinose) with the supplementation of the major hydrolysate inhibitors (acetate, furfural, and the end-product ethanol). The assay results indicated that while the mutant and parent strains grow equally well in the absence of an inhibitor (FIG. 10A), the five mutants had enhanced furfural tolerance and increased ethanol tolerance relative to their parental strain 33C in Rich Media supplemented with 2% (w/v) glucose (RMG2) (FIGS. 10B and C). Therefore, these five candidate strains had improved hydrolysate tolerance from their enhanced ethanol and/or furfural tolerance capabilities compared to parental strain 33C.

Figure 11:
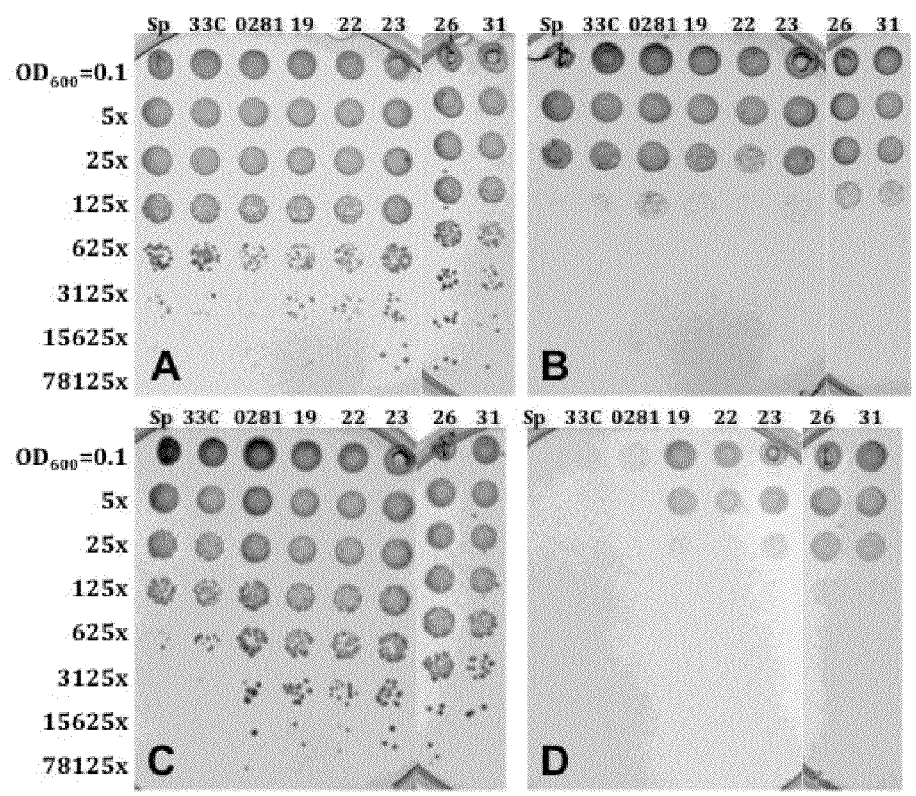
FIG. 11 shows the results of furfural sensitivity assays for Zymomonas strains OEL19 (19), OEL22 (22), OEL23 (23), OEL26 (26), OEL31 (31), and a strain that overexpresses ZMO0281 (0281), each with enhanced hydrolysate tolerance compared to their parental strain 33C as well as a control strain 33C-Sp (Sp). Shown are plates with 0 g/L furfural (A), 2 g/L furfural (B), 3 g/L furfural (C), and 4 g/L furfural (D).

An agar plate assay also indicated that these strains had enhanced furfural tolerance (FIG. 11). In the absence of furfural, the mutant strains had growth characteristics similar to that of the parental 33C strain (FIG. 11A). On the same plates supplemented with furfural, the mutant strains performed much better than 33C (FIG. 11B-D). As shown in FIGS. 11C and 11D, this result is particularly evident at higher furfural concentrations (3-4 g/L).

Example 3

Genetic Modifications in Hydrolysate Tolerant Biocatalysts

Genomic DNA was extracted and subjected to chromosomal sequencing to determine the insertional location of the promoter construct in each mutant and the genes affected by the insertion. Sequencing results indicated that the mutant designated OEL22 inserted into the upstream region of ZMO1162 gene (encoding a histidine kinase, PhoR homolog). The mutants designated OEL19, OEL23, OEL26, and OEL31 each inserted into ZMO0038 gene (encoding a Sigma 54 modulation protein), with OEL 31 inserted 16-bp downstream of the OEL19 insertion site. The insertions of OEL19, 23, 26, and 31 most likely cause the disruption of gene ZMO0038 by insertional deletion, and OEL22 may result in the over-expression ZMO1162/PhoR.

PCR primers were designed to amplify the regions covering the mutated regions of mutants OEL19 and OEL22. Using primer sets of OEL19_F (CCGTCCTTCCAATTCGATAA; SEQ ID NO:17) and OEL19_R (CCCCAATATGAC-CGAATCAC; SEQ ID NO:18) for OEL19 and OEL22_F (ATCGGCAATCATCAGGAAAG; SEQ ID NO:19) and OEL22_R (ATACCATCGCCTTCATCTGC; SEQ ID NO:20) for OEL22, the resulting PCR products (about 4.2 kb) containing portions up- and down-stream of the insertion sites were purified and electroporated into 33C or 8b competent cells to replace wild-type DNA nucleotide sequences with mutant version of OEL19 and OEL33 respectively. Four mutant strains were therefore constructed, designated 8b-OEL19, 8b-OEL22, 33C-OEL19 and 33C-OEL22. The transformants were confirmed by Sanger sequencing.

Figure 12:
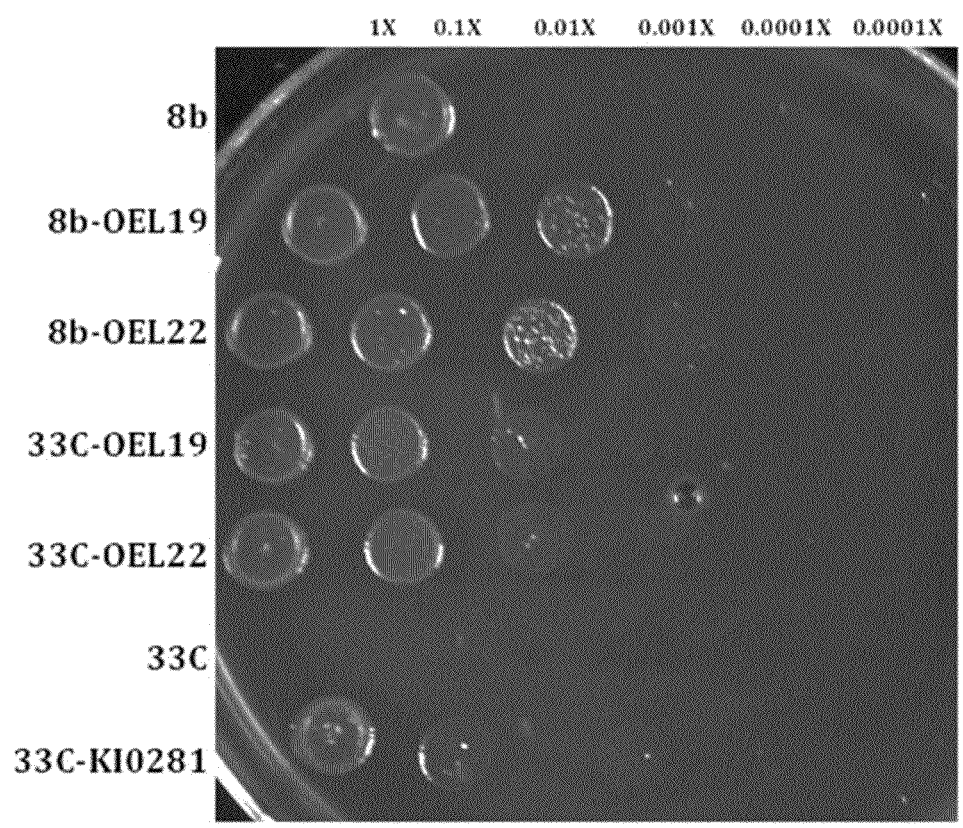
FIG. 12 shows the results of a 40% hydrolysate plate assay for unmodified Zymomonas strains (8b and 33C) and strains with modifications to ZMO0038 (8b-OEL19 and 33C-OEL19) or ZMO1162 (8b-OEL22 and 33C-OEL22).

The resulting strains and the parent strains 33C and 8b were subjected to the hydrolysate plate assay as described in Example 2 and FIG. 9. The results of this assay indicate that the 8b-OEL19, 8b-OEL22, 33C-OEL19 and 33C-OEL22 strains exhibited an enhanced hydrolysate tolerance of about 100- to 1,000-fold relative to the parent stains 33C and 8b (FIG. 12).

Example 4

Z. Mobilis 8b Knockout Library Construction and Screening

A transposition vector containing the spectinomycin resistant gene marker (pMOD2SpLoxP) flanked by loxP sites and transposable mosaic ends was used for the construction of a knockout library in Z. mobilis 8b by randomly inserting the DNA containing spectinomycin marker into the chromosome and/or native plasmid using transposase. The linear fragment from SCS110/pMOD2SpLoxP was prepared by digestion with PvuII followed by gel purification. Multiple transposon reactions containing 200 ng of the linear fragment with 2 uL 80% glycerol and 4 uL transposase was incubated at room temperature for 30 minutes, followed by electroporation into electrocompetent Z. mobilis 8b. Cells were outgrown without antibiotics for 6 hours at 30° C. in MMG (50 g/L glucose, 10 g/L yeast extract, 5 g/L tryptone, 2.5 g/L $(NH_4)_2SO_4$ and 0.2 g/L $K_2HPO_4$) and 100 mM $MgSO_4$, followed by plating on MMG plates containing 200 ng/mL spectinomycin. Thirty-eight plates containing approximately 600 colonies per plate (20,200 colonies total) were scraped from plates and grown in RMGSp200 for several generations prior to being preserved as glycerol stocks.

Both Z. mobilis 8b and 8b knockout library cultures were revived from glycerol stocks in 20 mL MRMG0.75×0.25 (10 g/L yeast extract, 2 g/L $KH_2PO_4$ and 1 g/L $MgSO_4.7H_2O$, 7.5 g/L glucose and 2.5 g/L xylose) and also containing 200 ng/mL spectinomycin for 1.5 hours at 35° C., 125 rpm. Cells were centrifuged and resuspended to a final $OD_{600\,nm}$ of 0.025 in a 100 mL culture, and grown for an additional 3-4 generations at 35° C. in 125 mL Erlenmeyer flasks with foam enclosures, 125 rpm (about 6 hours). Cells were initially screened on MRMGS (5% w/v glucose) plates containing 0, 3, 5, or 7.5 g/L of furfural, equivalent to MICs of 0.75×, 1× or 1.5×. MIC 1× is the minimum (lowest) concentration of inhibitor needed for complete inhibition of growth (RMG2) over a 24-hour period. Approximately 500, 1000 and 2000 colonies were plated in triplicates. Furfural levels were also tested at 0.7, 1.5, 3 or 4 g/L in glucose.

The agar plate dilution method was used to compare furfural tolerance among mutants which involved growing cultures to log phase in RMG2, then preparing 5-fold dilutions in microtiter plates. Using a 48-pin replicator, cells were replica plated onto RMG agar plates containing 0 or 3 g/L furfural and incubated anaerobically in chambers at 33° C. for 1 to 5 days.

Example 5

Growth and Fermentation Assays

For growth assays in sugars and furfural, Z. mobilis 8b was revived from frozen glycerol stocks for about 6-8 hours in 10 mL of RMG2 (2% glucose) at 33° C. Bioscreen C assays were carried out as described above. Cells were inoculated into Bioscreen C wells containing a total volume of 300 μL and incubated without shaking at 33° C. at an initial density of $OD_{600\,nm}$ of 0.05 (approximately 5×$10^6$ cells/mL). Turbidity measurements ($OD_{420-580\,nm}$) were taken every 10 minutes for up to 48 hours.

For pH controlled fermentation of Z. mobilis 8b in furfural, six fermentors (300 mL volume) were inoculated at an optical density $OD_{600\,nm}$=0.1 with Z. mobilis 8b in RMG8 (10 g/L yeast extract, 2 g/L $KH_2PO_4$ and 8% (w/v) glucose) with 0, 1, 2, 3, 4 or 5 g/L furfural, 33° C., pH of 6.0 controlled with 2M KOH. Fermentors were sparged with filter-sterilized nitrogen gas prior to fermentation. Samples were taken periodically to monitor cell densities, sugars, furfural and ethanol concentrations.

Example 6

Analysis of Mutants

From the preliminary screening of the knockout library described in Example 4, 34 colonies were isolated and evaluated for their growth in RMG2 containing 3 g/L furfural using Bioscreen C. Slight improvement in growth was observed (up to 20%) over the original 8b strain. Chromosomal sequencing of the insertion site revealed that two of the isolates had insertion sites within the same gene (ZMO1598) but at two different locations. ZMO1598 encodes for a 1-deoxy-D-xylulose-5-phosphate synthase (Dxs), an enzyme involved in several different pathways. There is also another gene ZMO1234, which also encodes for Dxs that is nearly identical to gene product of ZMO1598 present in Z. mobilis except for the protein amino and carboxyl terminus.

From a larger plate screening on 4 g/L furfural, 39 colonies were isolated, which were further screened on plates using the agar plate dilution method. An additional 51 colonies from the 3 g/L furfural plate screening were also tested. The majority of isolates were more viable at higher dilutions. Selected isolates from 3 and 4 g/L furfural screens were further tested in Bioscreen C growth assays in the presence of furfural; however, slight improvement was only noted (approximately 10-30%) at the 3 g/L furfural level and not at the lower concentrations.

Since two of the previous furfural tolerant spectinomycin (spec) mutants had insertions in dxs, it was possible this gene knockout was present in the remaining furfural isolates. Chromosomal DNA from isolates was tested for spec insertions in ZMO1598 and ZMO1234 by sequencing PCR products using primers homologous to the dxs gene. From 98 isolates, 29 were positive for insertions into ZMO1598 and 2 from ZMO1234. Furthermore, insertions were present in 13 different locations within the gene ZMO1598 and 2 within the gene ZMO1234. The mutations account for approximately 30% of the isolates tolerant to furfural and indicate a high likelihood that knockout of these genes is responsible for the observed phenotype.

Figure 13:
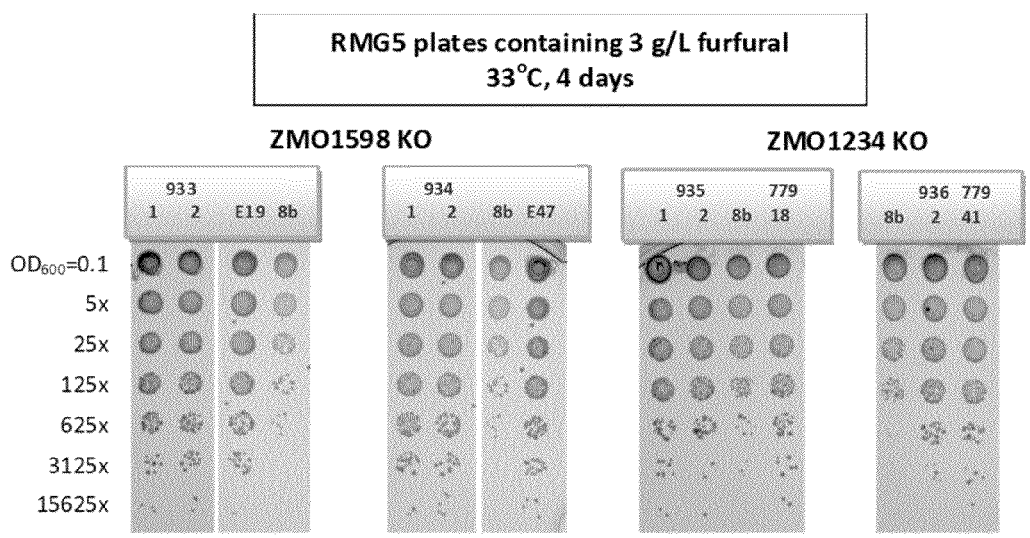
FIG. 13 shows the results of furfural sensitivity assays for Zymomonas strains with knockouts of ZMO1598 (#933 and #934) and ZMO1234 (#935 and #936) compared with control isolates from the knockout library (E19, E47, 779-18, and 779-41) on RMG agar plates containing 3 g/L furfural.

Using homologous recombination with linear DNA obtained by PCR of spec insertion of four isolates into native Z. mobilis 8b, four new mutants were tested and compared with knockout library isolates for furfural tolerance using the plate assay on 3 g/L furfural. As shown in FIG. 13, knockouts within the same genes of ZMO1598 and ZMO1234 in the original 8b strain had similar tolerance to furfural as the original isolate, confirming that the gene knockout, not adaptation, was responsible for the observed phenotype.

Chromosomal DNA from the remaining isolates that were not identified as ZMO1598 and ZMO1234 mutants were sequenced. Out of the 56 isolates sequenced, the majority of knockouts (44), had spectinomycin insertions within the operon containing the genes, ZMO0282, ZMO0283 and ZMO0285. There were 11 isolates with knockouts within the gene ZMO0282 at 6 different insertion sites, 19 within ZMO0283 at 12 unique insertion sites and 14 within ZMO0285 at 3 different insertion sites.

ZMO0282 has similarity to the acrA gene of *E. coli* and is a membrane fusion protein, part of a multi-drug efflux transport system, along with the acrB gene, an inner-membrane associated proton-substrate antiporter. It functions as a part of the AcrAB/TolC multidrug-efflux complex. The purpose of this system is for the extrusion of toxic chemicals. ZMO0285 has homology to the cusC gene of *E. coli*, which is an outer membrane porin, part of a copper/silver efflux transport system. Most likely it acts like TolC as the outer membrane protein, associating with ZMO0282 and ZMO0283. This analysis demonstrates that disrupting ZMO1598 and/or ZMO1234 as well as the operon containing ZMO0282, ZMO0283 and ZMO0285 conferred furfural resistance in *Zymomonas*. The great number of independent insertion events in these locations strongly suggested that these two hot spots for gene disruption create the observed furfural tolerant phenotype on agar plates, which was subsequently confirmed by constructing the knockout phenotypes in a clean 8b background. Also, a TetR family repressor gene ZMO0281 (which may be a potential repressor for the operon containing ZMO0282, ZMO0283 and ZMO0285) was upregulated during furfural challenge. Furthermore, overexpression of ZMO0281 also confirmed the improved furfural resistance in *Zymomonas*. These results demonstrate that either knockout of the expression of ZMO0282, ZMO0283 or ZMO0285 or downregulation of the expression of ZMO0282, ZMO0283 or ZMO0285 through the overexpression of the repressor confers furfural resistance.

We claim:

1. A microorganism of the genus *Zymomonas* comprising a genetic modification that increases the growth rate or biofuel production rate of the modified microorganism in the presence of a feedstock inhibitor compound relative to the growth rate or biofuel production rate of the unmodified microorganism wherein the genetic modification increases the expression or activity of a histidine kinase relative to the expression or activity level in the unmodified microorganism.

2. The microorganism of claim 1, wherein the genetic modification increases the expression or activity of ZMO1162 relative to the expression or activity level in the unmodified microorganism.

3. The microorganism of claim 1, wherein the genetic modification decreases the expression or activity of a functional sigma-54 modulation protein relative to the expression or activity level in the unmodified microorganism.

4. The microorganism of claim 1, wherein the genetic modification decreases the expression or activity of a functional protein encoded by ZMO0038 relative to the expression or activity level in the unmodified microorganism.

5. The microorganism of claim 1, wherein the genetic modification abolishes the function of a protein encoded by ZMO0038.

6. The microorganism of claim 1, wherein the microorganism is a bacterium.

7. The microorganism of claim 1, wherein the bacterium is a strain of *Zymomonas mobilis*.

8. The microorganism of claim 1, wherein the feedstock is corn stover.

9. The microorganism of claim 8, wherein the corn stover is pretreated with a dilute acid.

10. The microorganism of claim 1, wherein the feedstock inhibitor compound comprises furfural.

11. The microorganism of claim 1, wherein the biofuel is ethanol.

12. A method for producing a biofuel, comprising
    a) culturing the microorganism of claim 1 with a feedstock under conditions whereby the microorganism ferments the feedstock into a biofuel; and
    b) isolating the biofuel from the culture.

13. The method of claim 12, wherein the feedstock is lignocellulosic biomass.

14. The method of claim 13, wherein the lignocellulosic biomass has been pretreated with acid or enzymes to produce fermentable sugars.

15. The method of claim 12, wherein the feedstock is acid pretreated corn stover hydrolysate.

16. The method of claim 12, wherein the feedstock comprises fermentable sugars and at least one inhibitor compound.

17. The method of claim 16, wherein the at least one inhibitor compound is furfural.

18. The method of claim 12, wherein the biofuel is ethanol.

* * * * *